(12) United States Patent
Yang et al.

(10) Patent No.: US 11,708,335 B2
(45) Date of Patent: Jul. 25, 2023

(54) PYRIMIDINE COMPOUNDS USEFUL AS TYROSINE KINASE INHIBITORS

(71) Applicant: STERNGREENE, INC., Narberth, PA (US)

(72) Inventors: Lihu Yang, Edison, NJ (US); Guangning Ma, Shanghai (CN); Yingjie Cui, Shanghai (CN)

(73) Assignee: SternGreene, Inc., Narberth, PA (US)

( * ) Notice: Subject to any disclaimer, the term of this patent is extended or adjusted under 35 U.S.C. 154(b) by 0 days.

(21) Appl. No.: 16/954,792

(22) PCT Filed: Dec. 18, 2018

(86) PCT No.: PCT/US2018/066185
§ 371 (c)(1),
(2) Date: Jun. 17, 2020

(87) PCT Pub. No.: WO2019/126136
PCT Pub. Date: Jun. 27, 2019

(65) Prior Publication Data
US 2021/0094923 A1 Apr. 1, 2021

Related U.S. Application Data

(60) Provisional application No. 62/666,382, filed on May 3, 2018, provisional application No. 62/607,068, filed on Dec. 18, 2017.

(51) Int. Cl.
| | | |
|---|---|---|
| *C07D 239/94* | (2006.01) |
| *C07D 401/12* | (2006.01) |
| *C07D 403/04* | (2006.01) |
| *C07D 403/12* | (2006.01) |
| *C07D 405/12* | (2006.01) |
| *C07D 413/12* | (2006.01) |
| *C07D 417/12* | (2006.01) |
| *C07D 417/14* | (2006.01) |

(52) U.S. Cl.
CPC ......... *C07D 239/94* (2013.01); *C07D 401/12* (2013.01); *C07D 403/04* (2013.01); *C07D 403/12* (2013.01); *C07D 405/12* (2013.01); *C07D 413/12* (2013.01); *C07D 417/12* (2013.01); *C07D 417/14* (2013.01)

(58) Field of Classification Search
CPC .. C07D 405/12; C07D 413/12; C07D 417/12; C07D 417/14; C07D 239/94; C07D 401/12; C07D 403/04; C07D 403/12
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,457,105 A | 10/1995 | Barker |
| 5,591,767 A | 1/1997 | Mohr et al. |
| 5,616,582 A | 4/1997 | Barker |
| 5,639,476 A | 6/1997 | Oshlack et al. |
| 5,674,533 A | 10/1997 | Santus et al. |
| 5,698,155 A | 12/1997 | Grosswald et al. |
| 5,733,566 A | 3/1998 | Lewis |
| 5,747,498 A | 5/1998 | Schnur et al. |
| 5,770,599 A | 6/1998 | Gibson |
| 6,284,764 B1 | 9/2001 | Kath et al. |
| 6,391,874 B1 | 5/2002 | Cockerill et al. |
| 6,627,634 B2 | 9/2003 | Himmelsbach et al. |
| 6,713,485 B2 | 3/2004 | Carter et al. |
| 6,727,256 B1 | 4/2004 | Carter et al. |
| 6,828,320 B2 | 12/2004 | Cockerill et al. |
| 6,900,221 B1 | 5/2005 | Norris et al. |
| 6,972,288 B1 | 12/2005 | Himmelsbach et al. |
| 7,087,613 B2 | 8/2006 | Norris et al. |
| 7,157,466 B2 | 1/2007 | McClure et al. |
| 7,223,749 B2 | 5/2007 | Himmelsbach et al. |
| RE41,065 E | 12/2009 | Schnur et al. |

(Continued)

FOREIGN PATENT DOCUMENTS

| | | |
|---|---|---|
| CA | 2432428 | 9/2009 |
| CN | 104774184 | 4/2015 |

(Continued)

OTHER PUBLICATIONS

Chemical Abstracts Registry No. 1349009-29-5, indexed in the Registry File on ACS on STN, Dec. 5, 2011.*
Chemical Abstracts Registry No. 742679-78-3, indexed in the Registry File on ACS on STN, Sep. 12, 2004.*
Cancer and Metastasis Reviews (1998), 17(1), 91-106.*
Science (1999), vol. 286, 531-537.*
International Search Report (PCT/ISA/210) dated Jun. 24, 2019, by the Patent Cooperation Treaty, for International Application No. PCT/US2018/066185.
Written Opinion (PCT/ISA/237) dated Jun. 24, 2019, by the Patent Cooperation Treaty, for International Application No. PCT/US2018/066185.

(Continued)

*Primary Examiner* — Rebecca L Anderson

(57) ABSTRACT

The present disclosure provides pyrimidine compounds useful as tyrosine kinase inhibitors, and particularly epidermal growth factor receptor (EGFR) and human epidermal growth factor receptor 2 (HER2) inhibitors. The disclosed EGFR inhibitors are effective against acquired resistance mutations appearing after treatment of existing EGFR inhibitors. The present disclosure also provides methods of treating cancer using pyrimidine compounds and pharmaceutical compositions comprising pyrimidine compounds. The methods of treating cancer may be directed to cancer with acquired resistance mutations.

6 Claims, 11 Drawing Sheets

(56) References Cited

U.S. PATENT DOCUMENTS

| | | | |
|---|---|---|---|
| 7,863,281 | B2 | 1/2011 | Himmelsbach et al. |
| 8,710,068 | B2 | 4/2014 | Berezov et al. |
| 9,295,676 | B2 | 3/2016 | Berezov et al. |
| 2005/0107358 | A1 | 5/2005 | Himmelsbach et al. |
| 2008/0056990 | A1 | 3/2008 | Mishani et al. |
| 2014/0309246 | A1 | 10/2014 | Greene et al. |

FOREIGN PATENT DOCUMENTS

| | | |
|---|---|---|
| JP | H06-073025 | 3/1994 |
| JP | 2004-516283 | 6/2004 |
| JP | 3751201 | 12/2005 |
| WO | 02/50043 A1 | 6/2002 |
| WO | 2007/029251 A2 | 3/2007 |
| WO | 2011/084796 A2 | 7/2011 |
| WO | 2012/125913 A1 | 9/2012 |

OTHER PUBLICATIONS

Fang et al., "Design, synthesis, and evaluation of substituted 6-amide-4-anilinoquinazoline derivatives as c-Src inhibitors", RSC Adv. (2013), 3, pp. 26230-26240.

Pubmed Compound Summary for CID 70898473, VNZSGSPTMVATQB-UHFFFAOYSA-N, U.S. National Library for Medicine, Mar. 21, 2013, p. 1-13, p. 4 (https://pubchem.ncbi.nlm.nih.gov/compound/70898473.

Anastassiadis et al., "Comprehensive assay of kinase catalytic activity reveals features of kinase inhibitor selectivity", Nature Biotechnology (2011), 29:11, pp. 1039-1046.

Duong-Ly et al., "Kinase Inhibitor Profiling Reveals Unexpected Opportunities to Inhibit Disease-Associated Mutant Kinases", Cell Reports (2016), 14, pp. 772-781.

Hansen et al., "Re-examination and further development of a precise and rapid dye method for measuring cell growth/cell kill", Journal of Immunological Methods (1989); 119, pp. 203-210.

Hidaka et al., "Most T790M mutations are present on the same EGER allele as activating mutations in patients with non-small cell lung cancer", Lung Cancer (2017), 108, pp. 75-82.

Kong et al., "Structural pharmacological studies on EGFR T790M/C797S", Biochemical & Biophysical Research Communications (2017), 488, pp. 266-272.

Langer, "New Methods of Drug Delivery", Science (1990), 249:4976, pp. 1527-1533.

Mitsudomi et al., "Epidermal growth factor receptor in relation to tumor development: EGFR gene and cancer", FEBS Journal (2010), 277, pp. 301-308.

Ou et al., "Emergence of novel and dominant acquired EGFR solvent-front mutations at Gly796 (G796S/R) together with C797S/G and L792F/H mutations in one EGFR (L858R/T790M) NSCLC patient who progressed on osimertinib", Lung Cancer (2017), 108, pp. 228-231.

Ramalingam et al., "Osimertinib as First-Line Treatment of EGFR Mutation-Positive Advanced Non-Small-Cell Lung Cancer", Journal of Clinical Oncology (2018), 36:9, pp. 841-849.

Thress et al., "Acquired EGFR C797S mediates resistance to AZD9291 in advanced non-small cell lung cancer harboring EGFR T790M", Nat. Med. (2015), 21:6, pp. 560.562.

Yosaatmadja et al., "Binding mode of the breakthrough inhibitor AZD9291 to epidermal growth factor receptor revealed", Journal of Structural Biology (2015), 192, pp. 539-544.

Zhang et al., The efficacy and toxicity of afatinib in advanced EGFR-positive non-small-cell lung cancer patients after failure of first-generation tyrosine kinase inhibitors: a systematic review and meta-analysis, Journal of Thoracic Disease (2017), 9:7, pp. 1980-1987.

King, Chapter 89: Tablets, Capsules and Pills, Remington's 16th ed, Pharmaceutical Sciences (1980), pp. 1553-1593.

Radebaugh et al., Chapter 83: Preformulation, Remington's 19th ed, The Science & Pharmacy (1995), pp. 1447-1675.

Treat et al., Liposome Encapsulated Doxorubicin Preliminary Results of Phase I and Phase II Trials, Liposomes in the Therapy of Infectious Dieases and Cancer (1989), pp. 353-365.

Lopez-Berestein, Treatment of Systemic Fungal Infections with Liposomal-Amphotericin B, Liposomes in the Therapy of Infectious Diseases and Cancer (1989), pp. 317-327.

Lieberman et al., Pharmaceutical Dosage Forms: Tablets, 2d edition, vol. 3, (1990), 513 pages (4 parts).

Liu et al., "Recent Developments of Small Molecule EGFR Inhibitors Based on the Quinazoline Core Scaffolds," Anti-Cancer Agents in Medicinal Chemistry, vol. 12, No. 4 (Apr. 2012), pp. 391-406.

Shao et al., "6-Oxooxazolidine-quinazolines as noncovalent inhibitors with the potential to target mutant forms of EGFR," Bioorganic & Medicinal Chemistry, vol. 24, No. 16 (Apr. 2016) pp. 3359-3370.

Zheng et al., "Design, synthesis, and biological evaluation of novel 4-anilinoquinazoline derivatives bearing amino acid moiety as potential EGFR kinase inhibitors," European Journal of Medicinal Chemistry, vol. 130, (Feb. 2017), pp. 393-405.

Kuai et al., "Chemical Genetics Identifies Small-Molecule Modulators of Neuritogenesis Involving Neuregulin-I/ErbB4 Signaling," ACS Chemical Neuroscience (2010), vol. 1(4), pp. 325-342.

Tsou et al., "6-Substituted-4-(3-bromophenylamino)quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity," J. Med. Chem. (2001), vol. 44, pp. 2719-2734.

CAS Registry No. 742679-78-3 (Sep. 2004), 1 page.

* cited by examiner

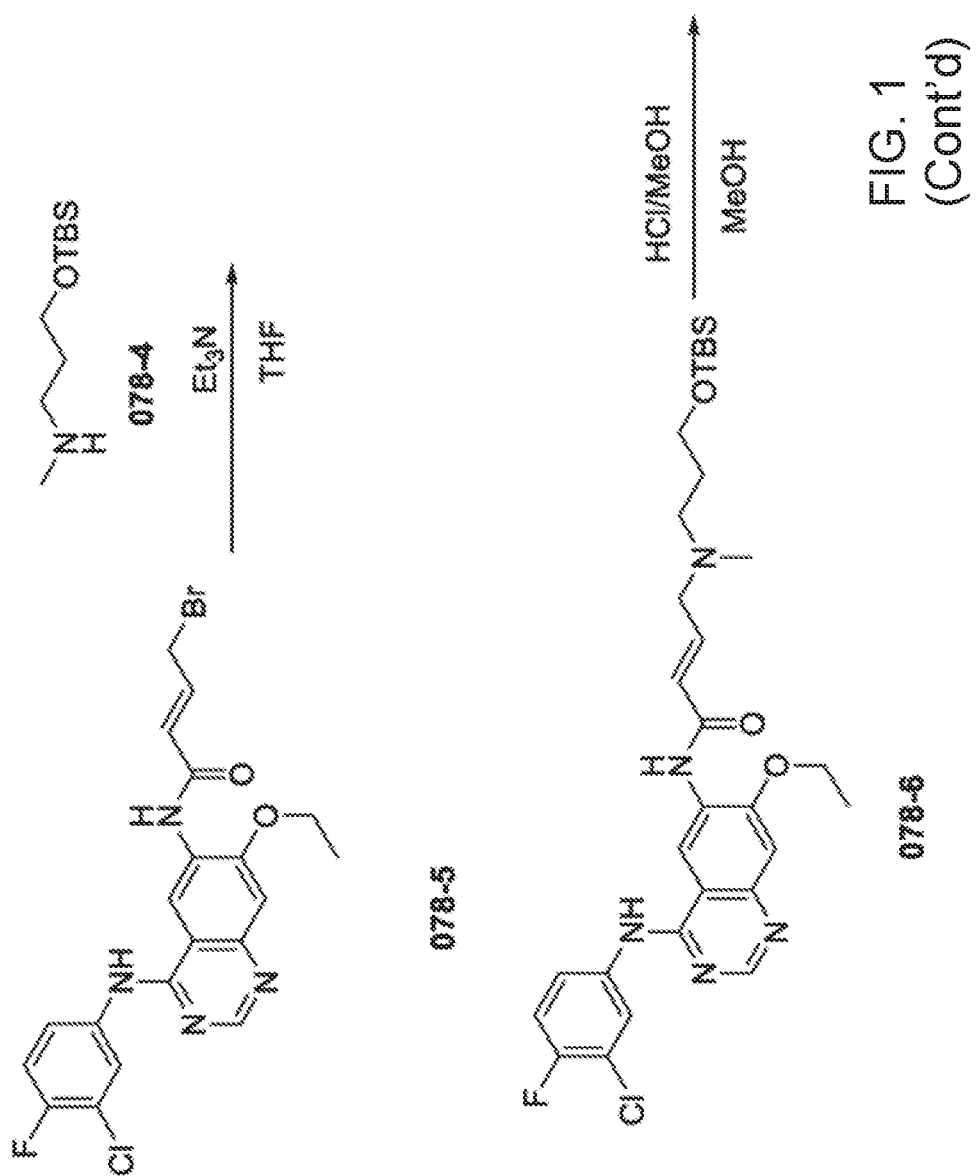

| Kinase: | ATP (uM): | Compound IC50* (M): | | |
|---|---|---|---|---|
| | | SGI-078 | SGI-105 | AZD9291 |
| EGFR | 10 | 1.37E-09 | 1.57E-10 | 1.40E-09 |
| EGFR (C797S) | 10 | 4.48E-10 | 8.33E-11 | > 1.00E-06 |
| EGFR (d746-750/T790M/C797S) | 10 | 6.97E-08 | 7.36E-08 | 2.86E-07 |
| EGFR (L858R) | 10 | 5.70E-09 | 3.27E-10 | 2.16E-09 |
| EGFR (L858R, T790M) | 10 | 6.02E-09 | 3.85E-10 | 1.09E-09 |
| EGFR (L858R/T790M/C797S) | 10 | 6.28E-08 | 1.46E-07 | 1.00E-06 |

FIG. 3

| Compounds | IC50 (nM) @ 72h ||
| --- | --- | --- |
| | A431 | NCI-H1975 |
| AZD-9291 | 3587 | 260 |
| SGI-078 | 8023 | 894 |
| SGI-105 | 2894 | 181 |

FIG. 4

PYRIMIDINE COMPOUNDS USEFUL AS TYROSINE KINASE INHIBITORS

RELATED APPLICATION

This application is a U.S. National Phase application of International Patent Application No. PCT/US2018/066185, filed Dec. 18, 2018, which claims the benefit of U.S. patent application Ser. No. 62/607,068, filed Dec. 18, 2017, and U.S. patent application Ser. No. 62/666,382, filed May 3, 2018.

FIELD

The present disclosure is in the field of medicinal chemistry. In particular, the disclosure is related pyrimidine compounds, pharmaceutical compositions comprising one or more of these compounds, and their use as tyrosine kinase inhibitors and epidermal growth factor receptor inhibitors. The present disclosure also provides methods of treating cancer.

BACKGROUND

Tyrosine kinase inhibitors (TKIs) having specificity for the epidermal growth factor receptor (EGFR) demonstrate clinical activity in individuals with non-small cell lung cancer having an activating mutation of EGFR. See Hidaka et al., "Most T790M mutations are present on the same EGFR allege as activating mutations in subjects with non-small cell lung cancer," *Lung Cancer* 108:76-82 (2017).

Acquired EGFR resistance mutations to osimertinib can be common; mutations in EGFR C797S can abolish the covalent binding of osimertinib to EGFR. See Ou et al., "Emergence of novel and dominant acquired EGFR solvent-front mutations at Gly796 (G796S/R) together with C797S/R and K792F/H mutations in one EGFR (L858R/T790M) NSCLE subject who progressed on osimertinib," *Lung Cancer* 108:228-231 (2017). The C797S mutation does not significantly alter the structure and function of the EGFR kinase, but the mutation increases the local hydrophilicity around residue 797. See Kong et al., "Structural pharmacological studies on EGFR T790M/C797S," *Biochemical and Biophysical Research Communications* 488:266-272 (2017).

Lung cancers having a EGFR mutation can be highly sensitive to EGFR tyrosine kinase inhibitors such as gefitinib and erlotinib. See Mitsudomi et al., "Epidermal growth factor receptor in relation to tumor development: EGFR gene and cancer," *FEBS Journal* 277:301-308 (2010).

Afatanab has been disclosed as a potential therapeutic for advanced EGFR mutated non-small cell lung cancer patients after the failure of first generation TKIs. See Zhang et al., "The efficacy and toxicity of afatinib in advanced EGFR-positive non-small-cell lung cancer patients after failure of first-generation tyrosine kinase inhibitors: a systematic review and meta-analysis," *Journal of Thoracic Disease* 9(7):1980-1987 (2017). Afatanib is structurally different than osimertinib and that they bind differently; afatanib can even bind in unexpected ways. See Ramalingam et al., "Osimertinib As First-Line Treatment of EGFR Mutation-Positive Advanced Non-Small-Cell Lung Cancer," *Journal of Clinical Oncology* (2017); see also Thress et al., "Acquired EGFR C797S mutation mediates resistance to AZD9291 in non-small cell lung cancer harboring EGFR T790M," *Nature Medicine* 21(6):560-564 (2015); Duong-Ly et al., "Kinase inhibitor profiling reveals unexpected opportunities to inhibit disease-associated mutant kinases," *Cell Rep.* 14(4):772-781 (2016); Yosaatmadja et al., "Binding mode of the breakthrough inhibitor AZD9291 to epidermal growth factor receptor revealed," *Journal of Structural Biology* 192:539-544 (2015).

Mutation mimicking compounds that bind to the kinase domain of EGFR and methods of treating cancer or tumors using small molecules having specificity for the Survivin protein has been explored in U.S. Pat. Nos. 8,710,068 and 9,295,676.

SUMMARY

In certain embodiments, the present disclosure provides compounds of the formula (I),

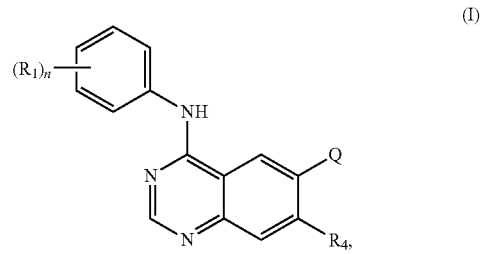

(I)

or a pharmaceutically acceptable salt thereof, wherein the compound of formula (I) is defined herein.

In certain embodiments, the present discourse provides compounds of the formula (II),

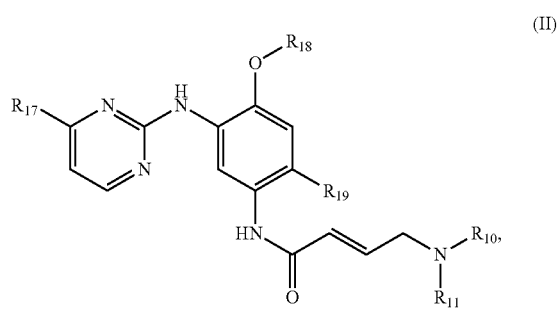

(II)

or a pharmaceutically acceptable salt thereof, wherein the compound of formula (II) is defined herein.

In certain embodiments, the present disclosure provides pharmaceutical compositions comprising the compound of formula (I) or formula (II). In certain embodiments, the present disclosure provides a method of treating cancer, comprising administering to a subject in need thereof a therapeutically effective amount of a compound.

BRIEF DESCRIPTION OF THE FIGURES

FIG. 3 shows the ctivity of different inhibitors against various EGFR mutants in the presence of 10 μM ATP;

FIG. 4 shows in vitro proliferation of A431 and NCI-1975 cells to determine IC50 for EGFR kinase inhibitors.

DETAILED DESCRIPTION

Figure 1:
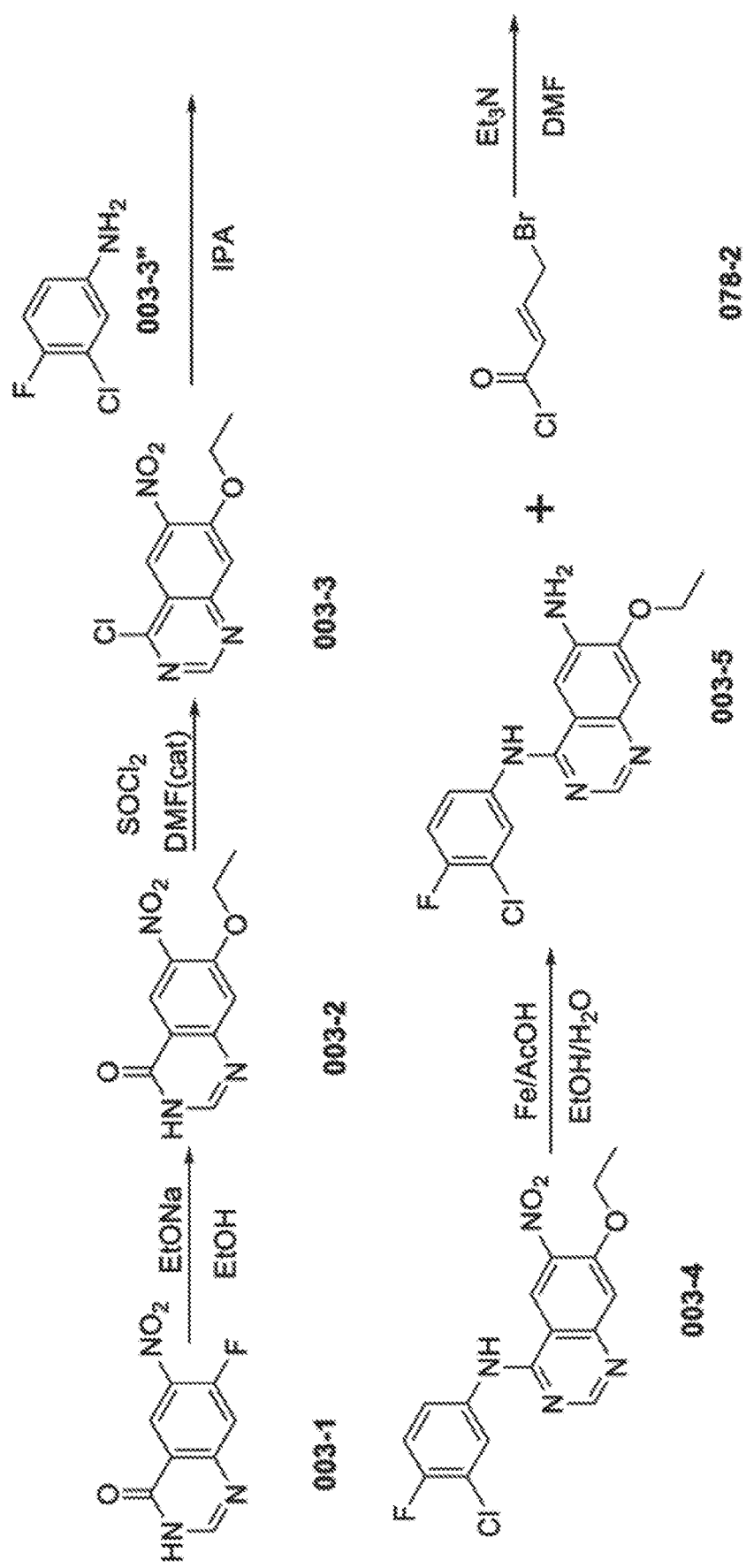
FIG. 1 shows the synthesis route of a representative compound of SGI-078.
Figure 1:
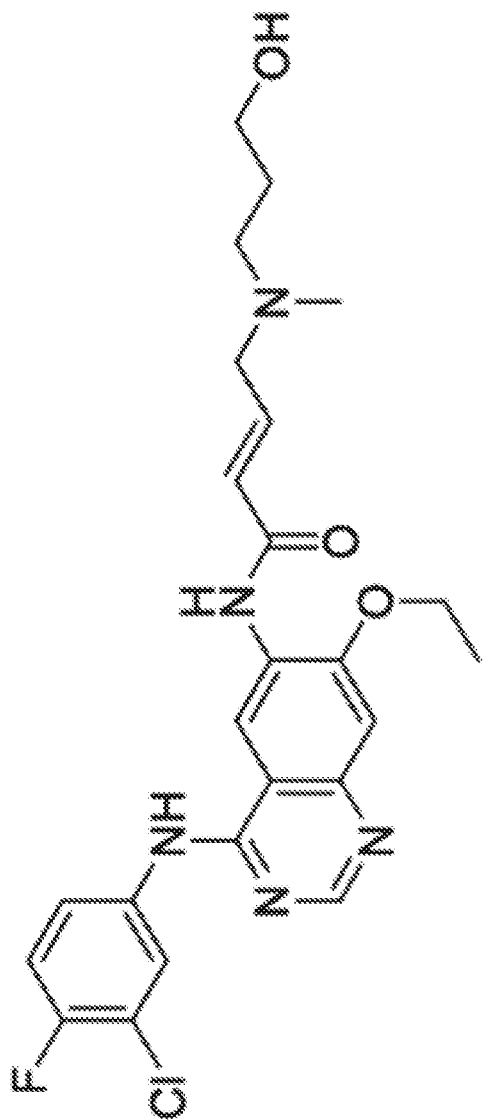
Figure 1:
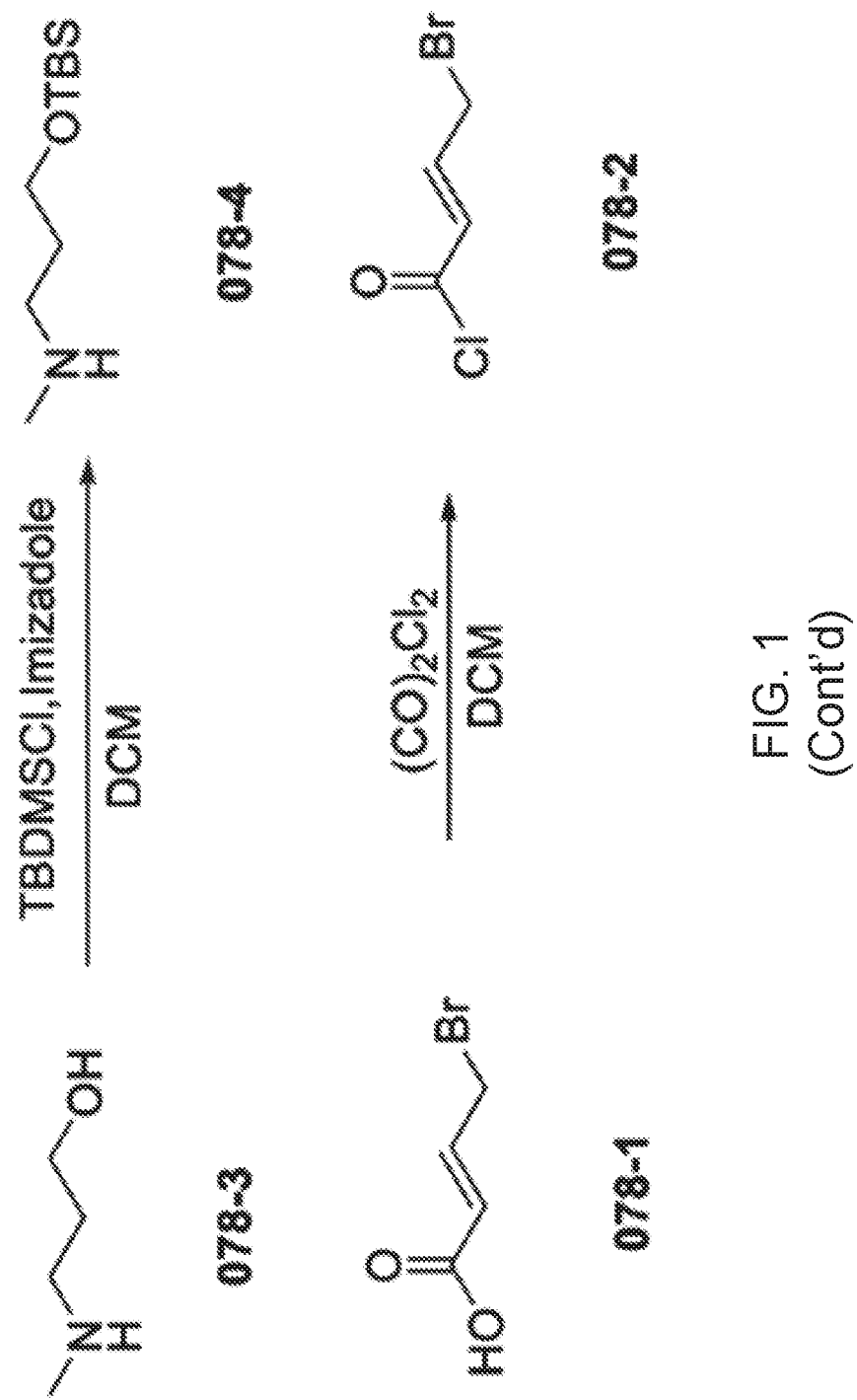

It has been found that compounds of formula (I) or formula (II) are inhibitors for EGFR kinase. Not wishing to be bound by theory, it is predicted that these compounds inhibit EGFR kinase by targeting a cavity near the ATP binding pocket in the kinase domain. The inhibitors demonstrate activity against the C797S, L858R, and T790M mutations, as well as the EGFR sensitive mutations. The inhibitors also inhibit HER2 with potent activity.

Various examples and embodiments of the inventive subject matter disclosed here are possible and will be apparent to a person of ordinary skill in the art, given the benefit of this disclosure. In this disclosure reference to "some embodiments," "certain embodiments," "certain exemplary embodiments" and similar phrases each means that those embodiments are non-limiting examples of the inventive subject matter, and there may be alternative embodiments which are not excluded.

The articles "a," "an," and "the" are used herein to refer to one or more than one (i.e., to at least one) of the grammatical object of the article. By way of example, "an element" means one element or more than one element.

As used herein, the term "about" means±10% of the noted value. By way of example only, a composition comprising "about 30 wt %" of a compound could include from 27 wt. % of the compound up to and including 33 wt. % of the compound.

The word "comprising" is used in a manner consistent with its open-ended meaning, that is, to mean that a given product or process can optionally also have additional features or elements beyond those expressly described. It is understood that wherever embodiments are described with the language "comprising," otherwise analogous embodiments described in terms of "consisting of" and/or "consisting essentially of" are also contemplated and within the scope of this disclosure.

Compounds of the Disclosure

In certain embodiments, the present disclosure provides a compound of the formula (I), (I)

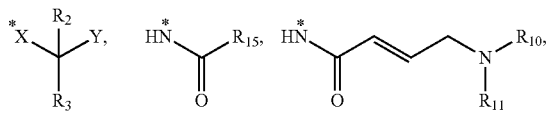

wherein
Q is

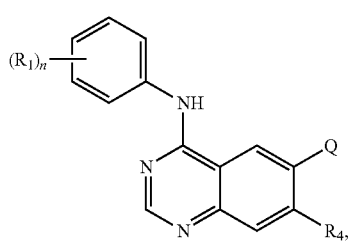

-continued

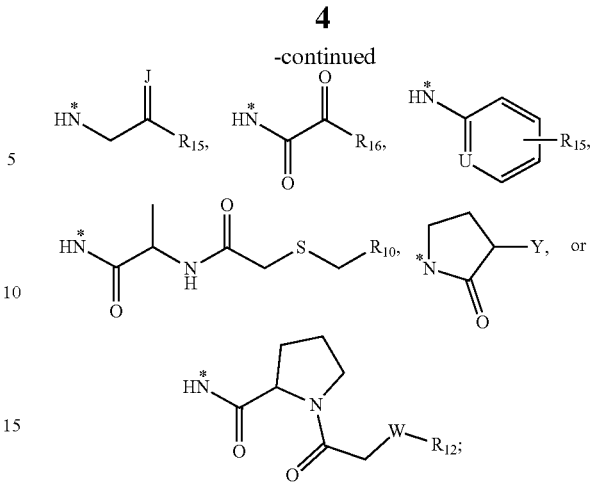

$R_1$ is independently H, optionally substituted amino, optionally substituted $C_{1-6}$ alkyl, optionally substituted $C_{1-6}$ alkoxy, optionally substituted $C_{2-6}$ alkenyl, optionally substituted $C_{2-6}$ alkynyl, optionally substituted benzyloxy, cyano, halo, hydroxy, nitro, optionally substituted phenoxy, or mono-, di-, or trifluoromethyl;
n is 1, 2, or 3;
$R_2$ is H or $C_{1-6}$ alkyl;
$R_3$ is H or $C_{1-6}$ alkyl;
$R_4$ is H, $N(R_6)_2$, optionally substituted $C_{1-3}$ alkyl, optionally substituted $C_{1-3}$-alkoxy, cyano, halo, hydroxy, nitro, (S)-3-((tetrahydrofuran-3-yl)oxy), or mono-, di-, or trifluoromethyl;
$R_5$ is H or $C_{1-6}$ alkyl;
$R_6$ is independently H, alkyl, $C_{1-6}$ alkylamine, or $C_{1-6}$ alkylhydroxy;
X is $C_{1-6}$ alkyl, —$N(R_5)C(O)$—, —$O$-($C_{1-6}$ alkyl)-, —$N(R_5)$-($C_{1-6}$ alkyl)-, —$C(O)N(R_5)$—, —$C(O)N(R_5)$-($C_{1-6}$ alkyl)-, —$SO_2N(R_5)$—, or —$N(R_5)SO_2$-($C_{1-6}$ alkyl)-;
Y is

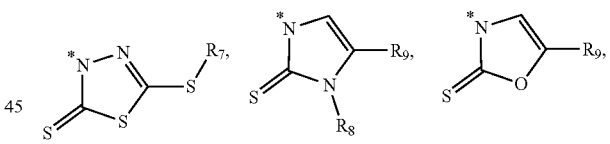

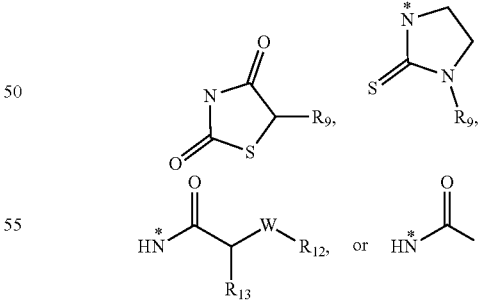

$R_7$ is $C_{1-6}$ alkyl, $C_{1-6}$ alkylhydroxy, optionally substituted $C_{1-6}$ alkylether, $C_{1-6}$ alkylcarboxylic acid, $C_{1-6}$ alkyldicarboxylic acid, optionally substituted $C_{1-6}$ alkylester, $C_{1-6}$ alkylcarboxylate, optionally substituted $C_{1-6}$ alkyphosphoric acid, or $C_{1-6}$ alkysulfuric acid;
$R_8$ is $C_{1-6}$ alkyl;
$R_9$ is $C_{1-6}$ alkylcarboxylic acid;
U is C or N;

$R_{10}$ is $C_{1-6}$ alkylcarboxylic acid, $C_{1-6}$ alkyl alcohol, $C_{1-6}$ alkyl ether, or $C_{1-6}$ alkyl ester;
$R_{11}$ is H, $C_{1-6}$ alkyl, $C_{1-6}$ alkyl alcohol, $C_{1-6}$ alkyl ether, or $C_{1-6}$ alkyl ester;
W is C, S, or O;
$R_{12}$ is $C_{1-6}$ alkylcarboxylic acid or $C_{1-6}$ alkylhydroxy;
$R_{13}$ is H or $C_{1-6}$ alkyl;
$R_{14}$ is $C_{1-6}$ alkyl;
J is O or S;
$R_{15}$ is optionally substituted cycloalkyl, optionally substituted heterocycloalkyl, optionally substituted aryl, optionally substituted heteroaryl, $C_{1-6}$ cyanoalkyl; and
$R_{16}$ is optionally substituted aryl or heterocycloalkyl;
wherein * represents the point of attachment,
or a pharmaceutically acceptable salt thereof.

In certain embodiments, Q can be

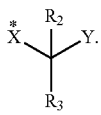

In certain embodiments, Q can be

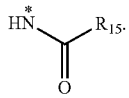

In certain embodiments, Q can be

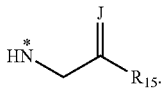

In certain embodiments, Q can be

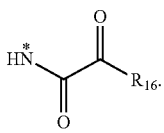

In certain embodiments, Q can be

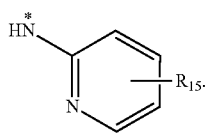

In certain embodiments, Q can be

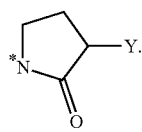

In certain embodiments, Q can be

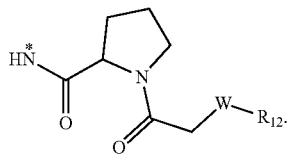

In certain embodiments, Q can be

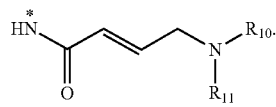

In certain embodiments, $R_1$ can be cyano or halo. In certain embodiments, $R_1$ can be fluoro or chloro.

In certain embodiments, n can be 1. In certain embodiments, n can be 2. In certain embodiments, n can be 3.

In certain embodiments, $R_2$ can be H. In certain embodiments, $R_2$ can be methyl or ethyl.

In certain embodiments, $R_3$ can be H. In certain embodiments, $R_3$ can be methyl or ethyl.

In certain embodiments, $R_4$ can be optionally substituted $C_{1-6}$ alkoxy. In certain embodiments, the $C_{1-6}$ alkoxy can be substituted by $C_{1-6}$ alkylhydroxyl, $C_{1-3}$ alkoxy, $C_{3-6}$ cycloalkyl, or optionally substituted heterocycloalkyl. In certain embodiments, $R_4$ can be $N(R_6)_2$.

In certain embodiments, X can be $C_{1-6}$ alkyl. In certain embodiments, X can be —$N(R_5)C(O)$—. In certain embodiments, X can be —O-($C_{1-6}$ alkyl)-. In certain embodiments, X can be $N(R_5)$-($C_{1-6}$ alkyl)-. In certain embodiments, X can be —$C(O)N(R_5)$—. In certain embodiments, X can be —$C(O)N(R_5)$-($C_{1-6}$ alkyl)-. In certain embodiments, X can be —$SO_2N(R_5)$—. In certain embodiments, X can be —$N(R_5)SO_2$-($C_{1-6}$ alkyl)-.

In certain embodiments, Y can be

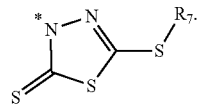

In certain embodiments, Y can be

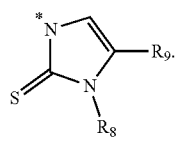

In certain embodiments, Y can be

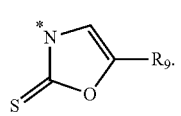

In certain embodiments, Y can be

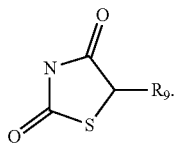

In certain embodiments, Y can be

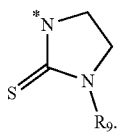

In certain embodiments, Y can be

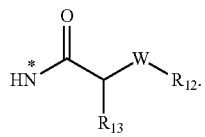

In certain embodiments, Y can be

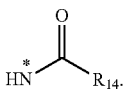

In certain embodiments, $R_7$ can be $C_{1-6}$ alkylcarboxylic acid. In certain embodiments, $R_7$ can be optionally substituted $C_{1-6}$ alkylester. In certain embodiments, $R_7$ can be $C_{1-6}$ alkyldicarboxylic acid. In certain embodiments, $R_7$ can be optionally substituted $C_{1-6}$ alkyphosphoric acid.

In certain embodiments, $R_{10}$ can be $C_{1-6}$ alkyl alcohol.
In certain embodiments, $R_{11}$ can be $C_{1-6}$ alkyl alcohol.
In certain embodiments, W can be C. In certain embodiments, W can be S. In certain embodiments, W can be O.

In certain embodiments, Ru can be $C_{1-6}$ alkylcarboxylic acid. In certain embodiments, $R_{12}$ can be $C_{1-6}$ alkylhydroxy.

In certain embodiments, J can be O. In certain embodiments, wherein J can be S.

In certain embodiments, U can be N.

In certain embodiments, $R_{15}$ can be optionally substituted cycloalkyl. In certain embodiments, $R_{15}$ cam ne optionally substituted heterocycloalkyl.

In certain embodiments, Rib can be optionally substituted aryl. In certain embodiments, wherein $R_{16}$ can be heterocycloalkyl.

In certain embodiments, a compound of the present disclosure can have the following structure:

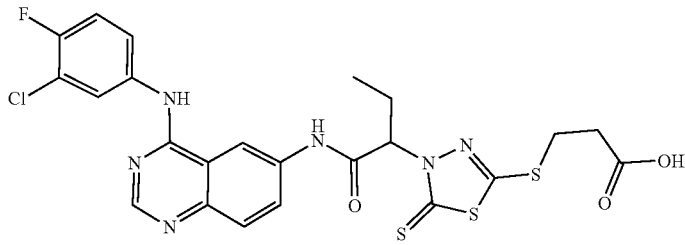

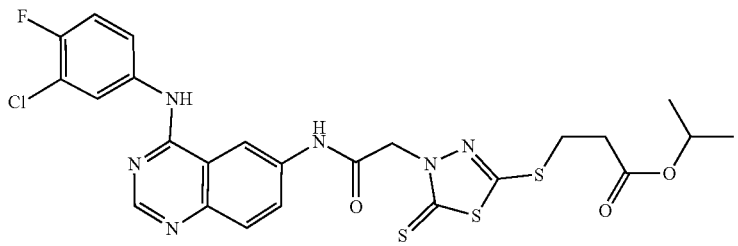

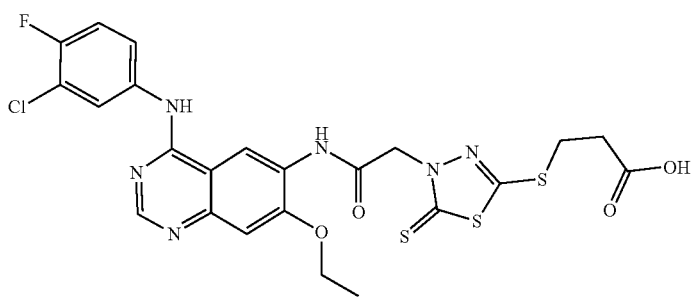

-continued
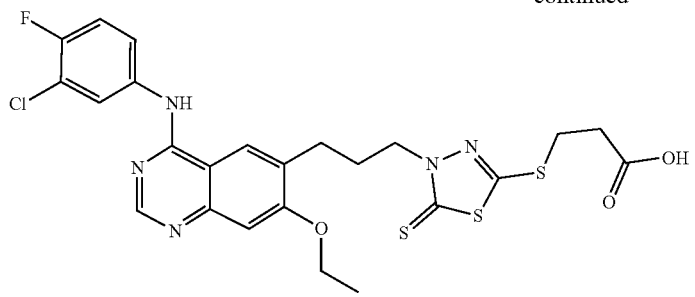
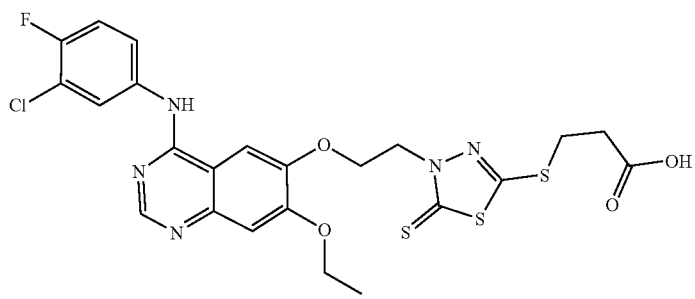
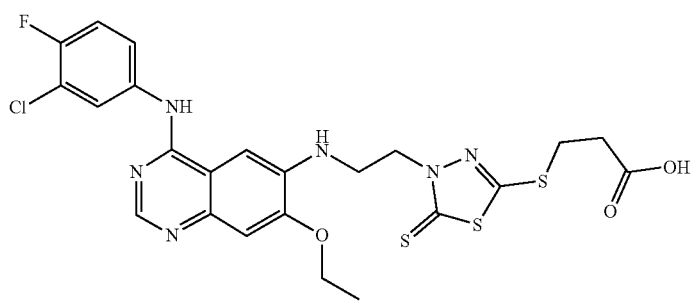
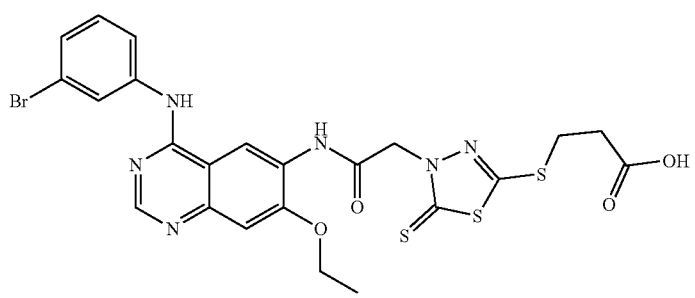
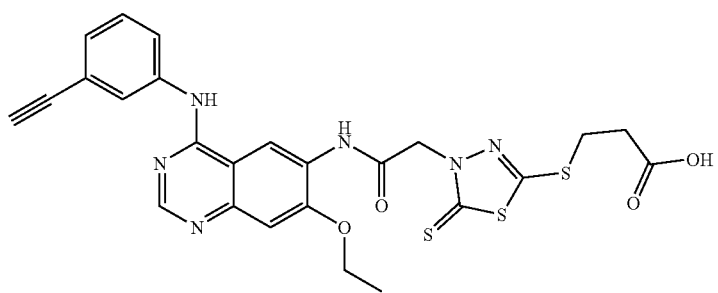

-continued
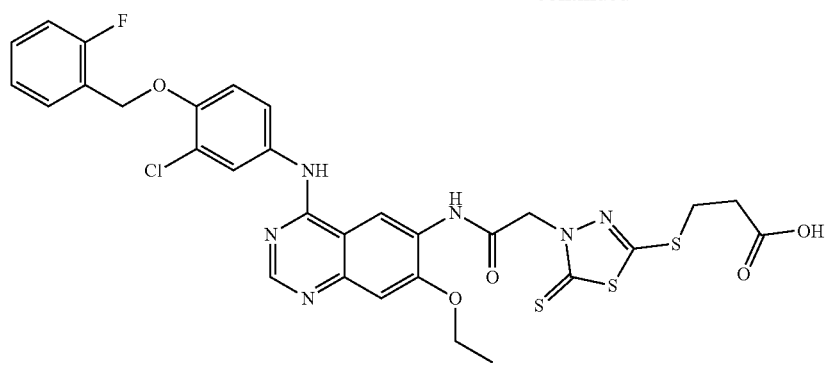
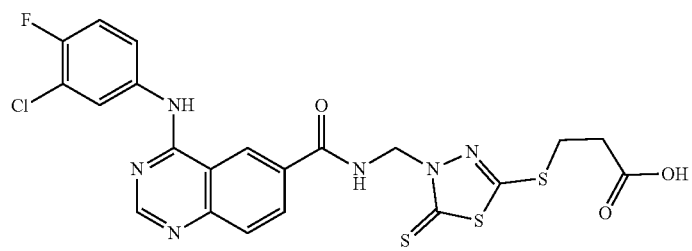
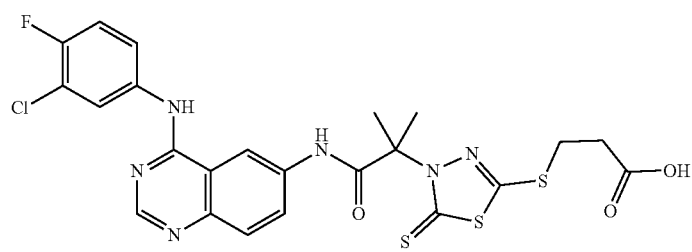
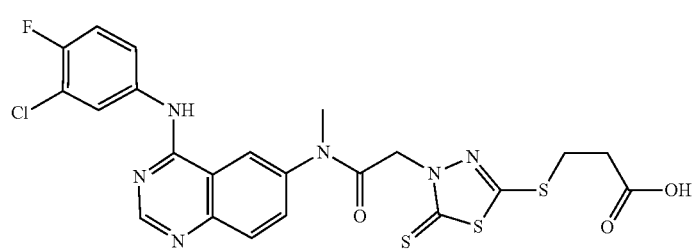
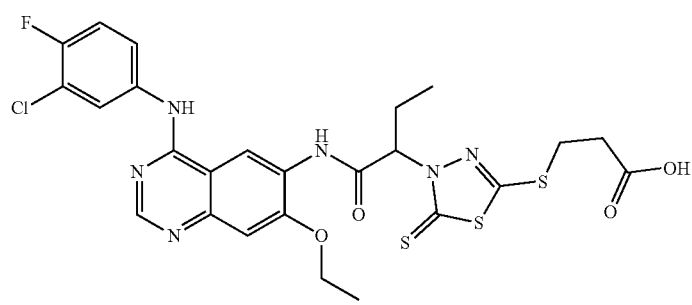
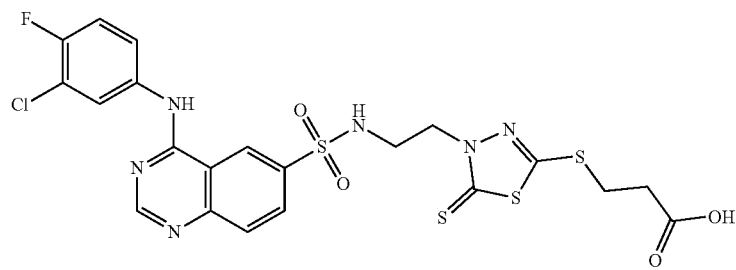

-continued
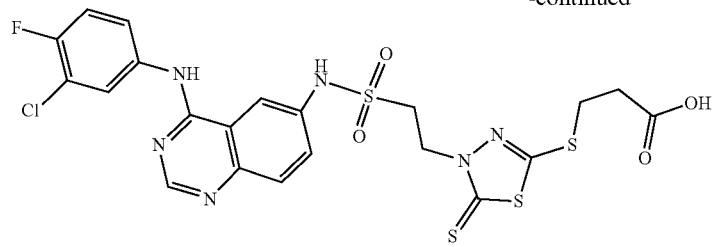
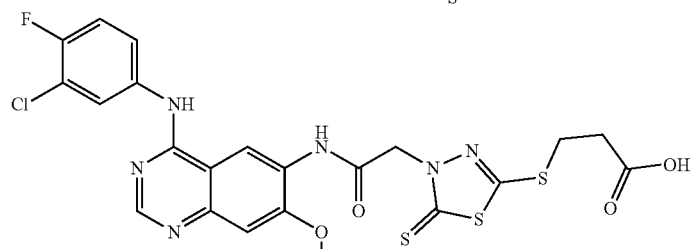
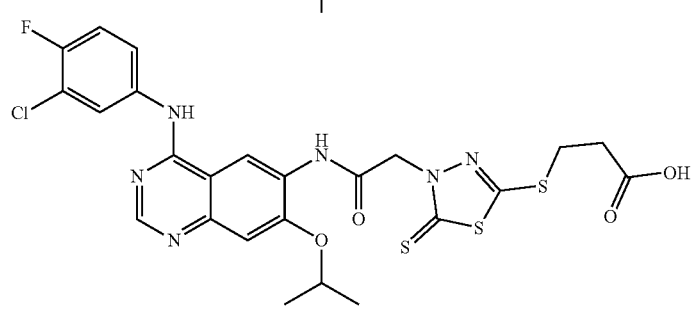
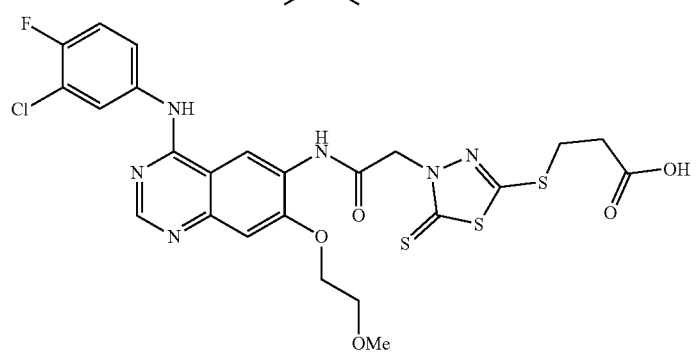
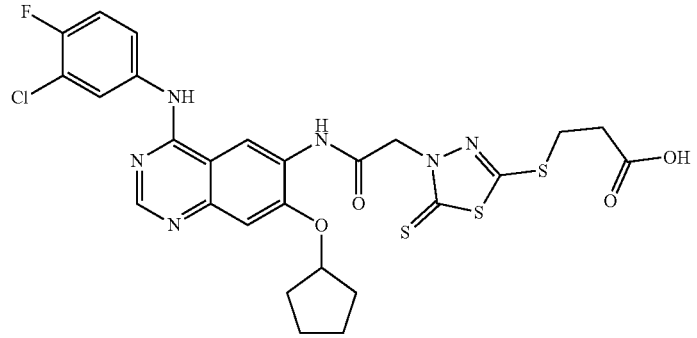
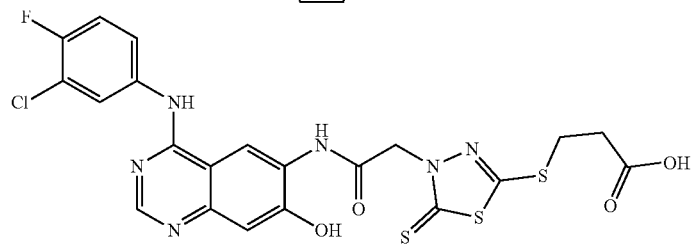

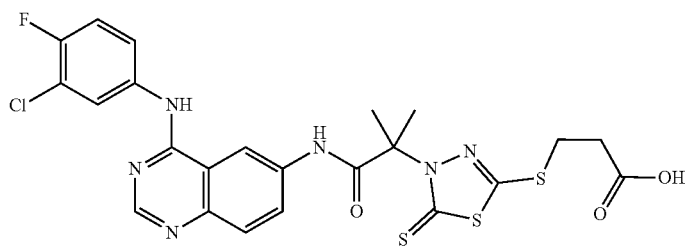
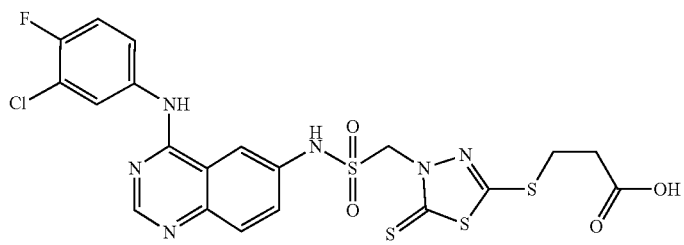
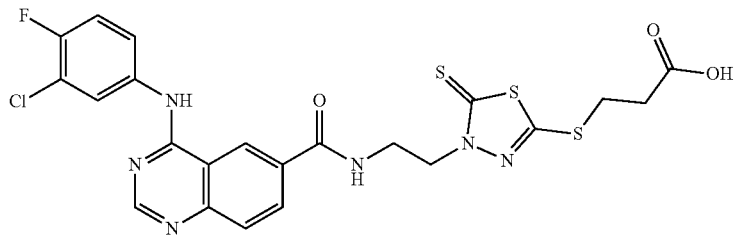
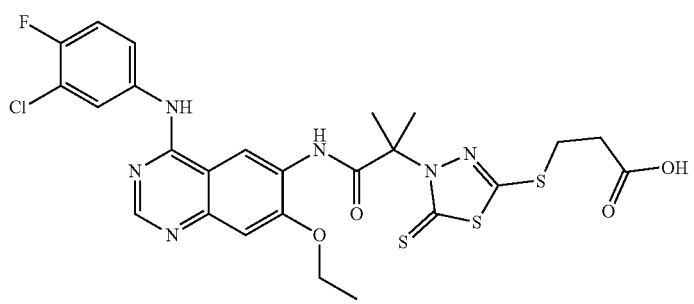
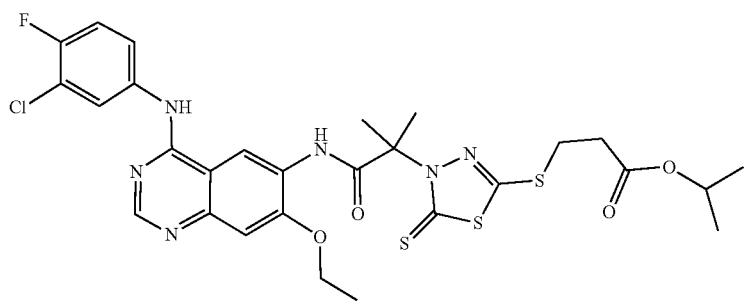
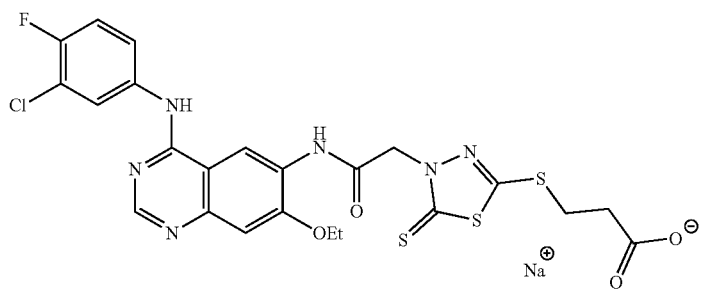

-continued
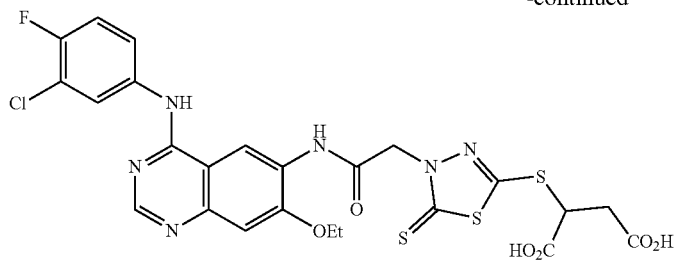
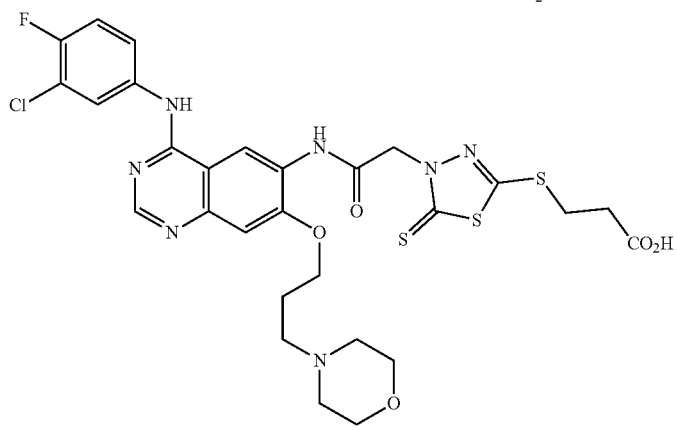
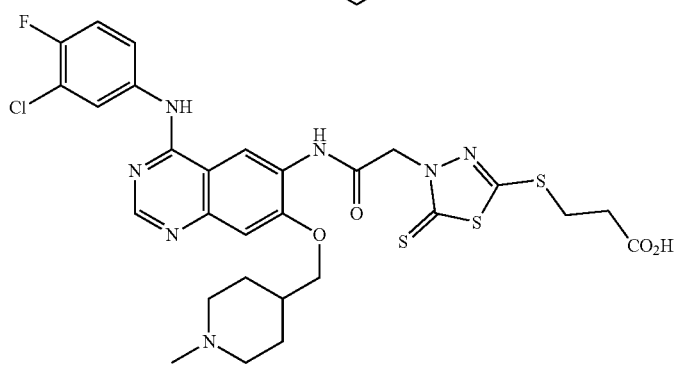
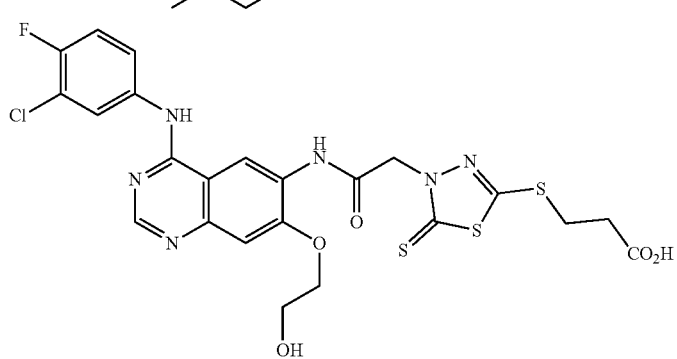
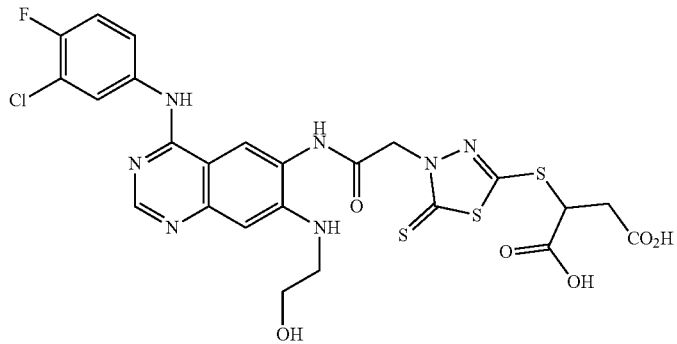

-continued
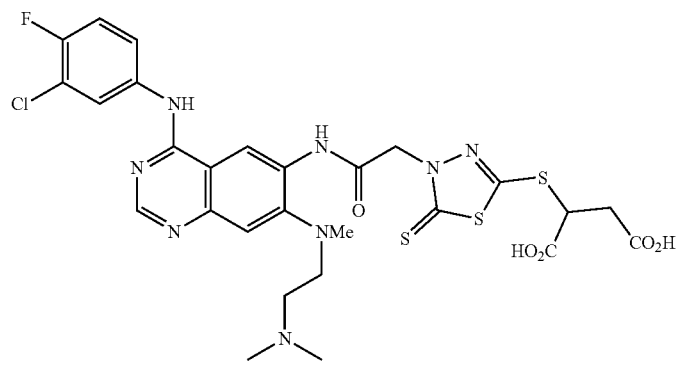
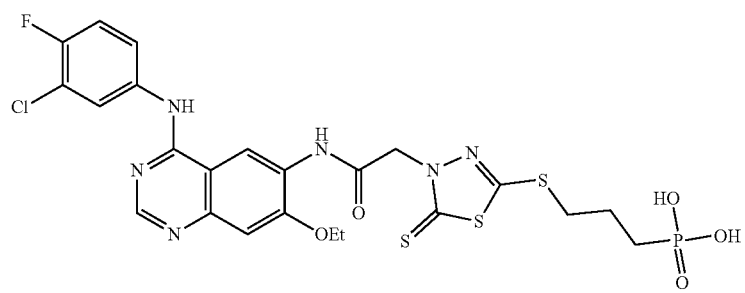
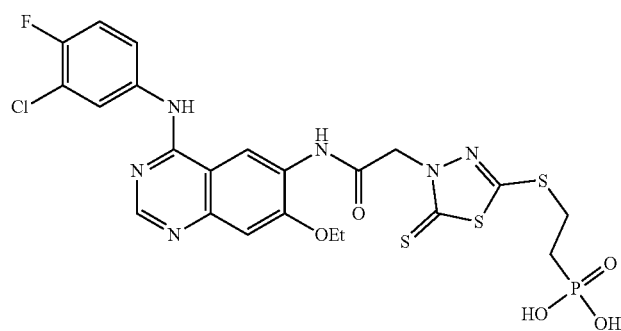
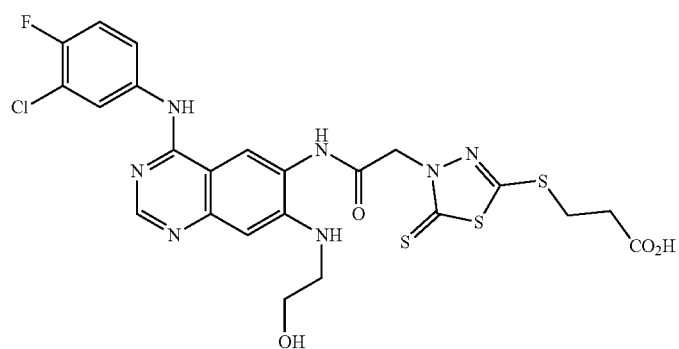
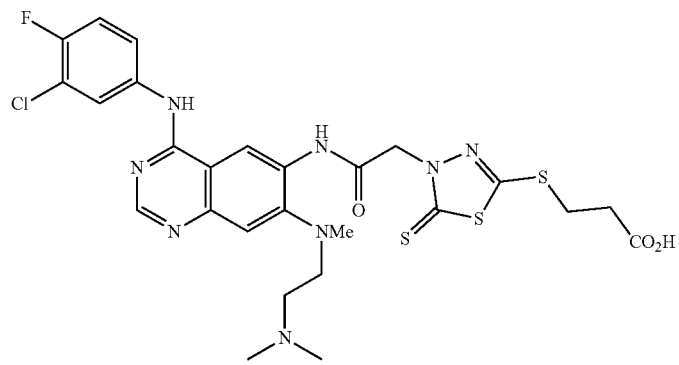

-continued
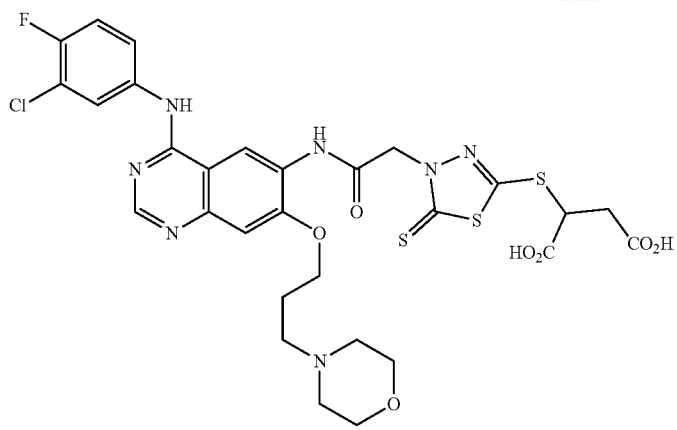
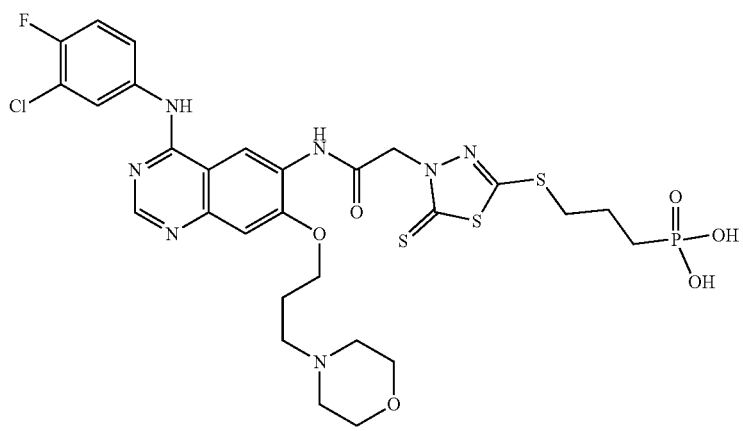
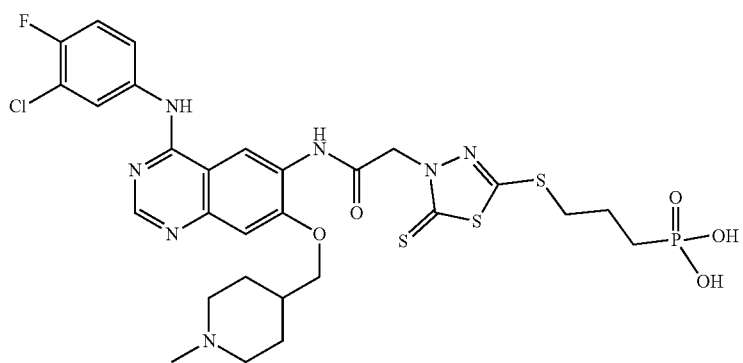
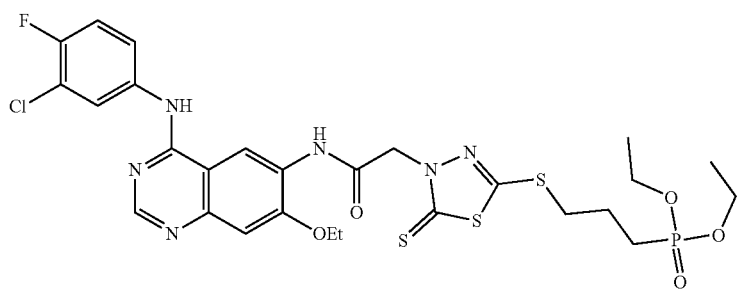

-continued
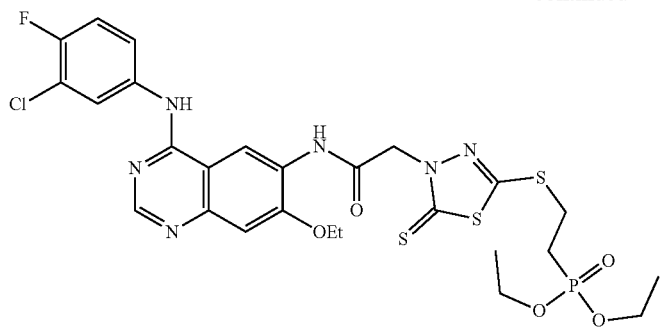
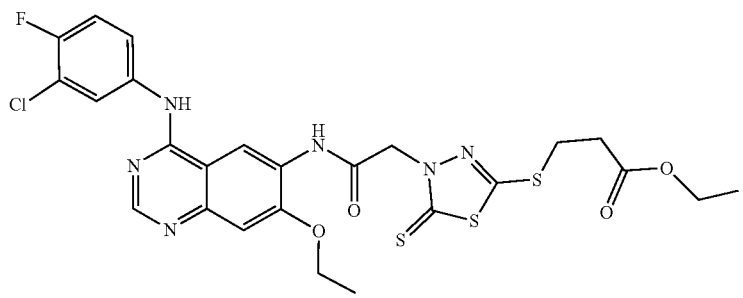
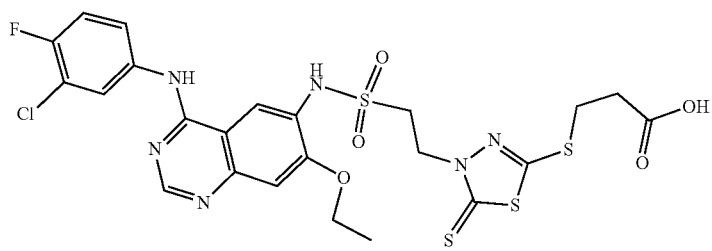
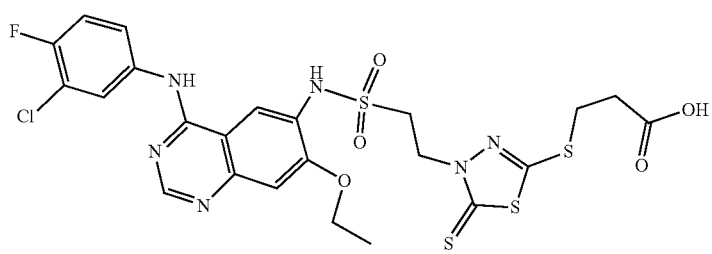
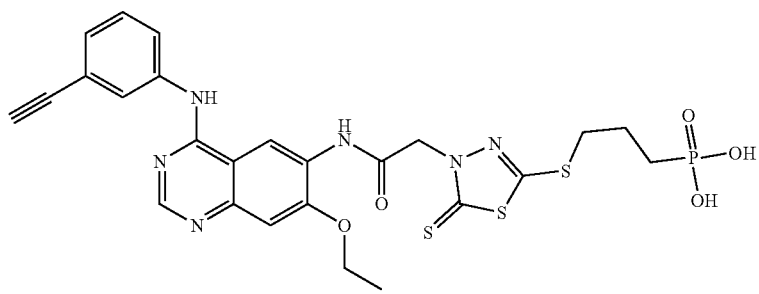
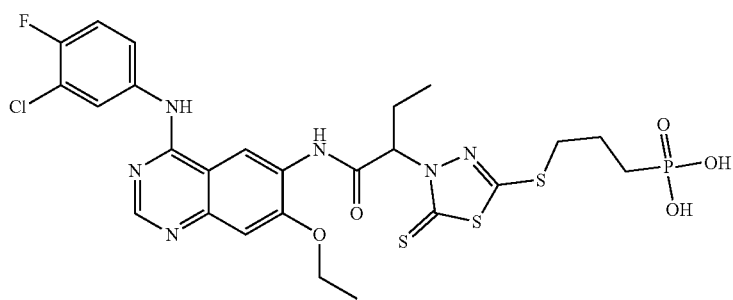

-continued
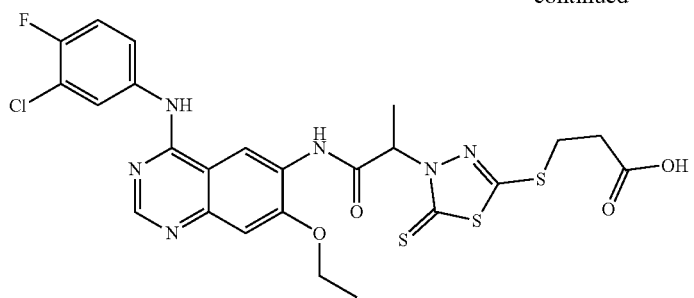
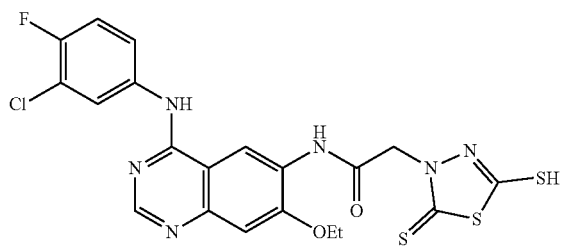
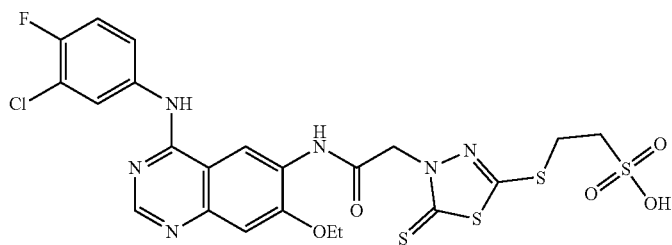
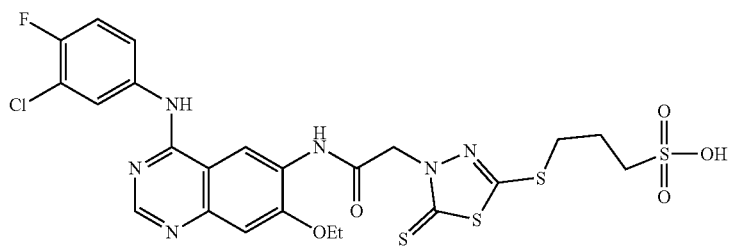
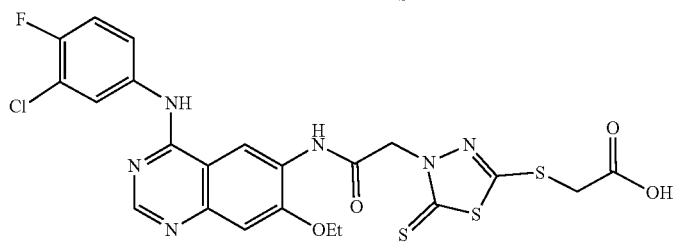
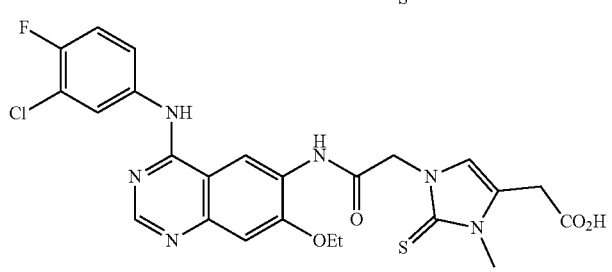

-continued
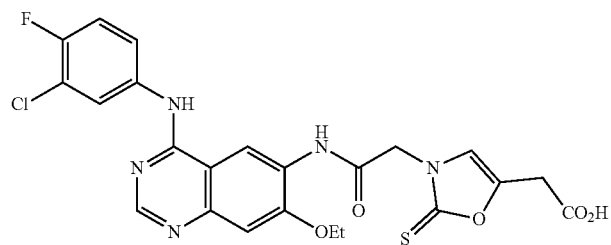
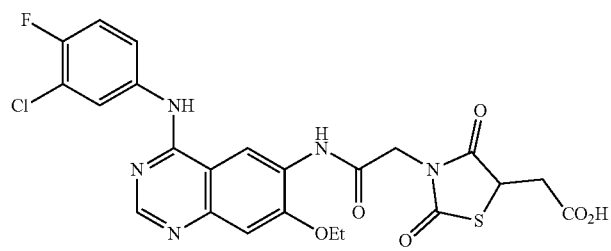
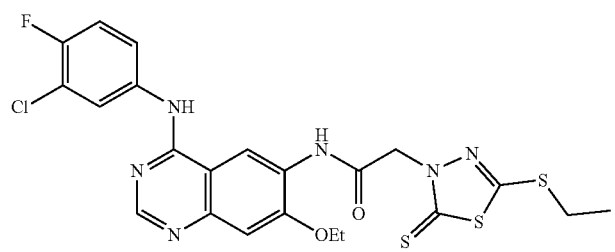
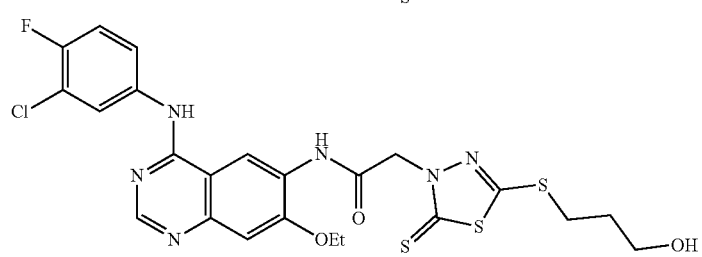
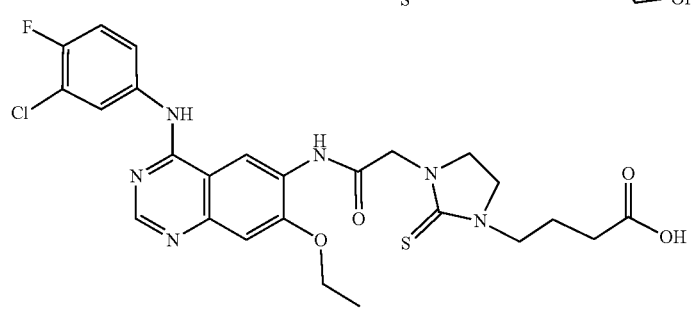
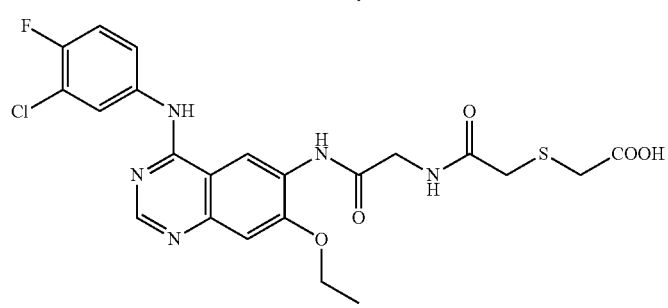

-continued
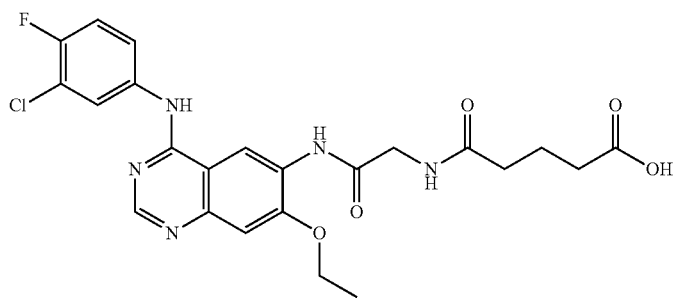
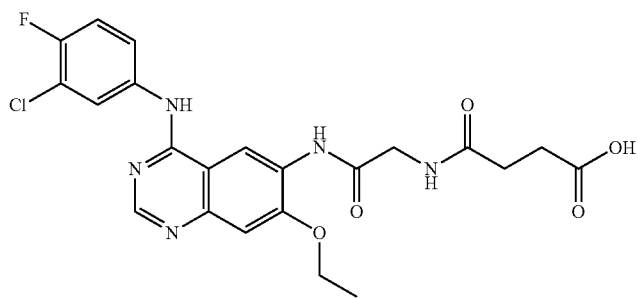
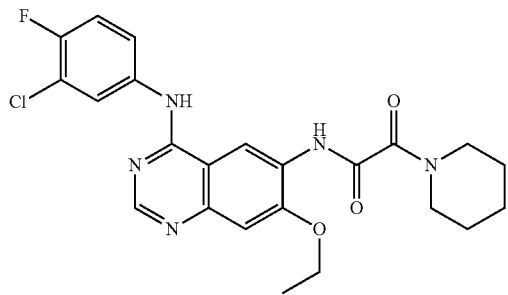
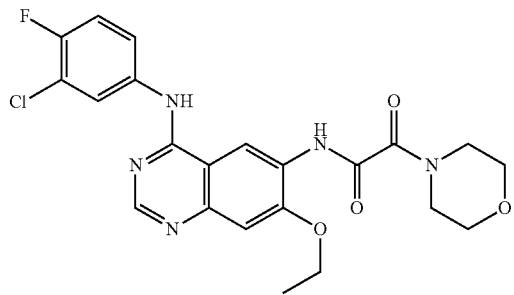
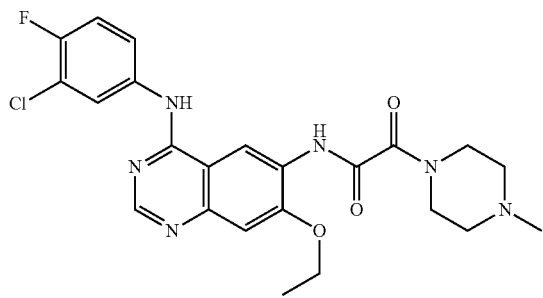
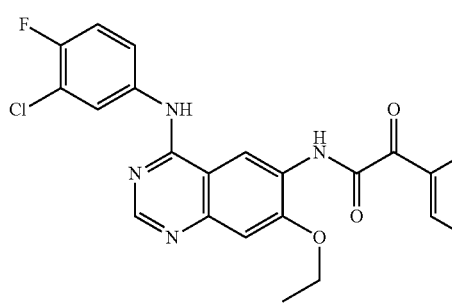
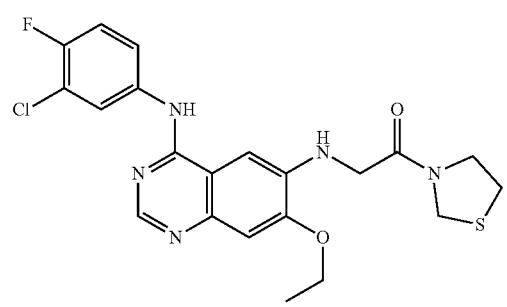

-continued
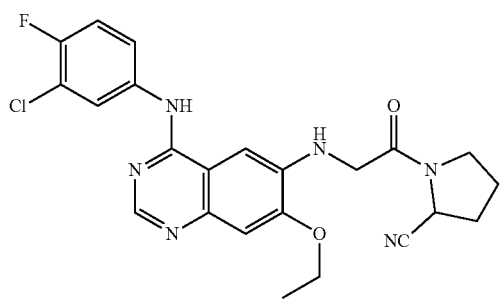
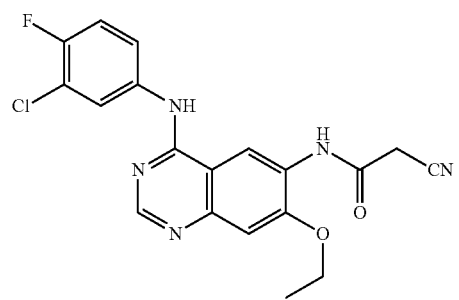
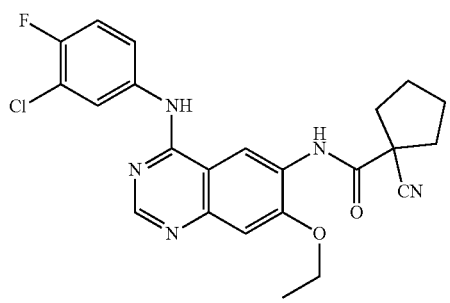
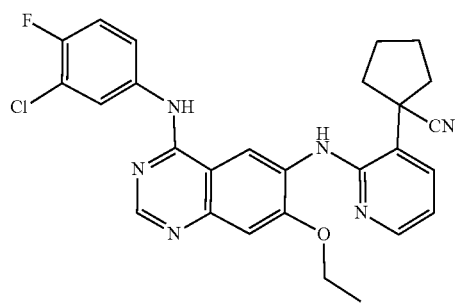
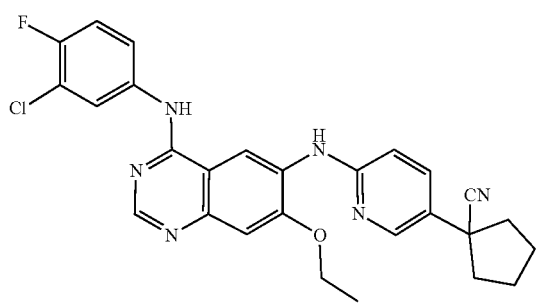
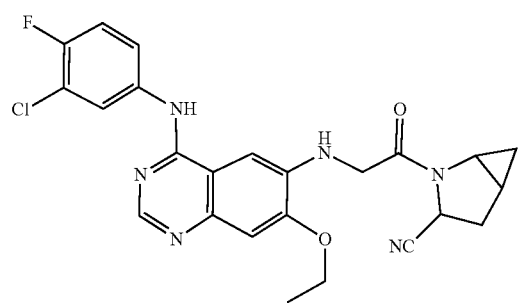
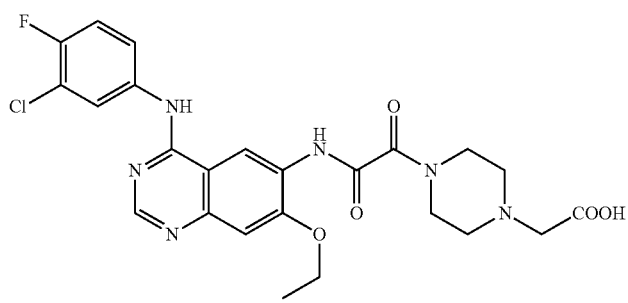
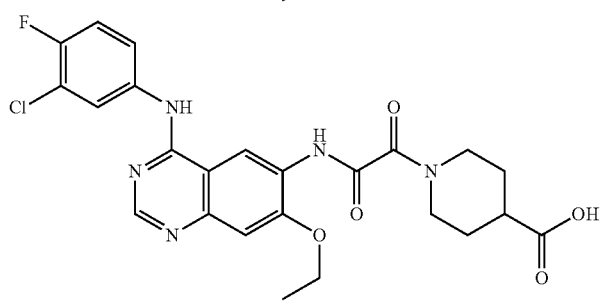

-continued
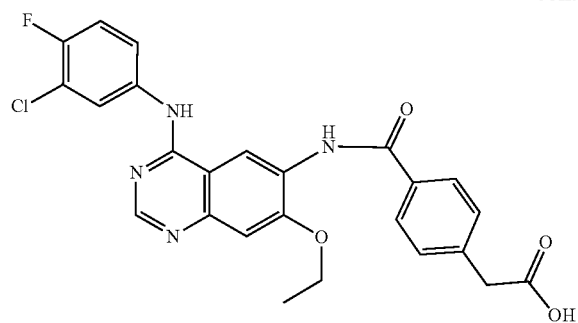
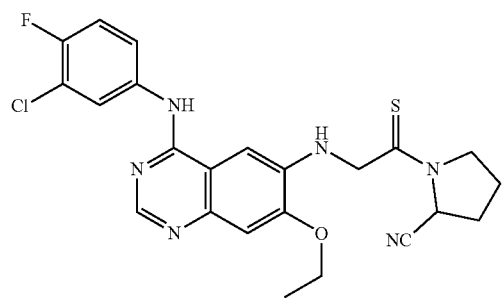
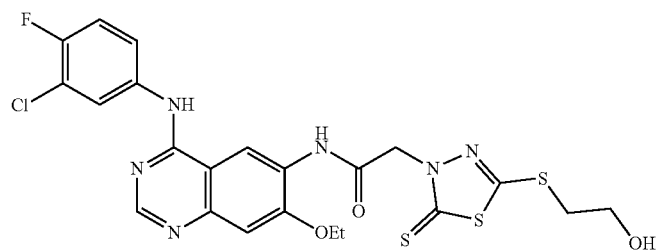
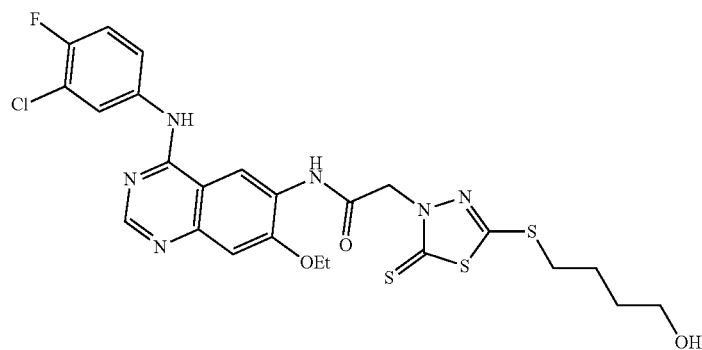
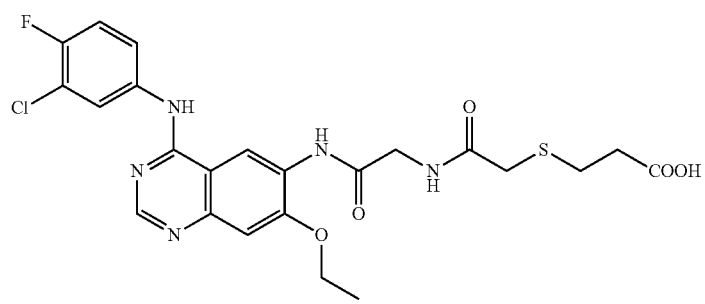

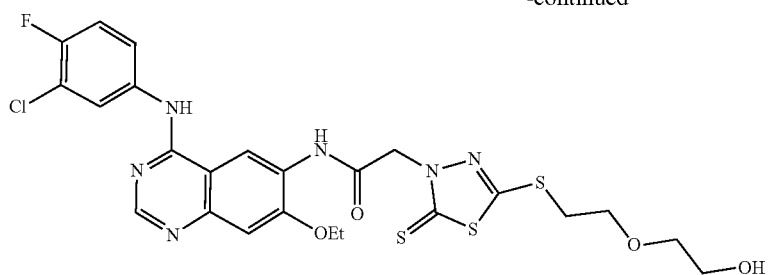
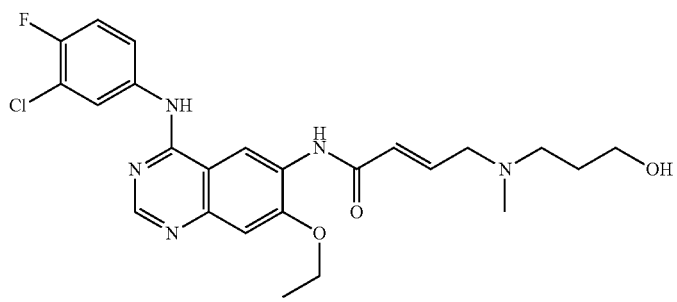
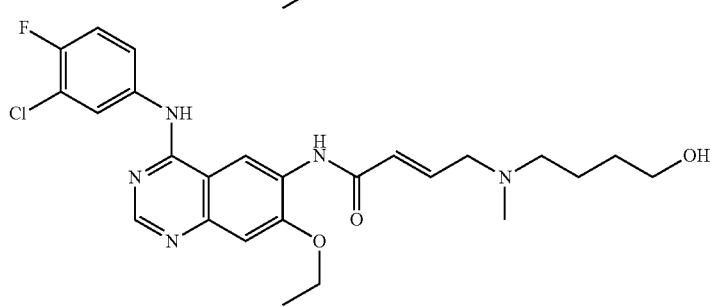
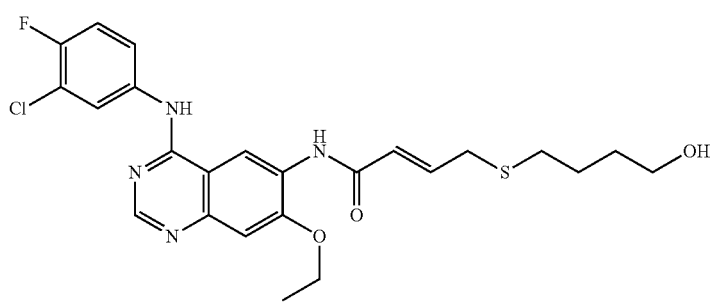
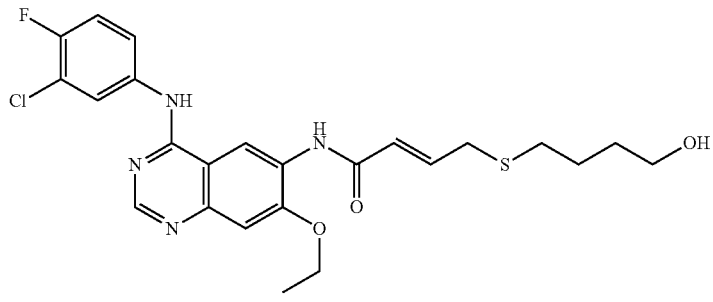
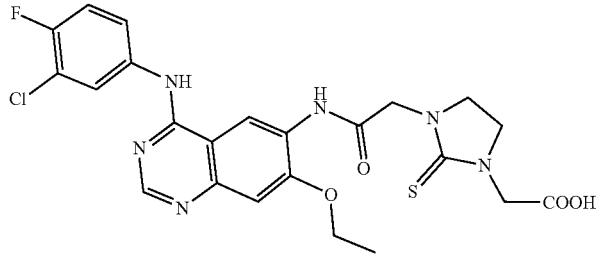

-continued
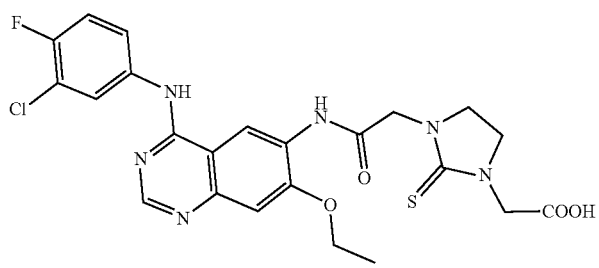
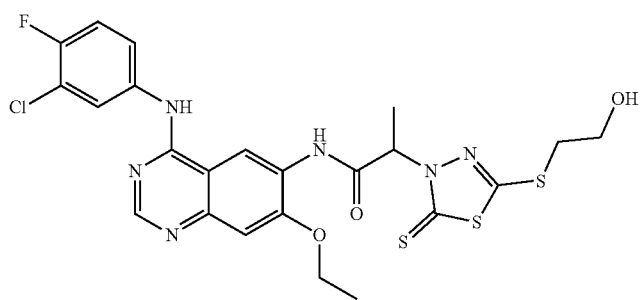
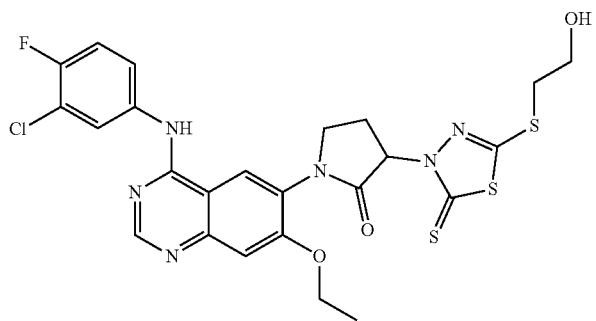
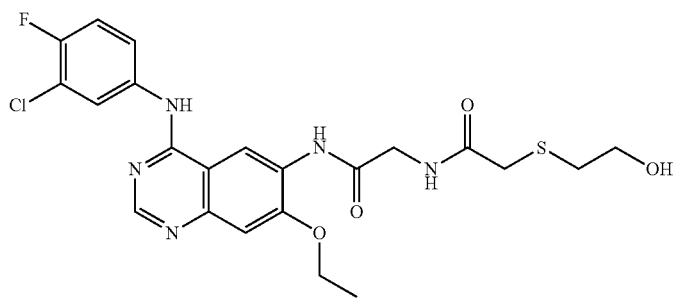
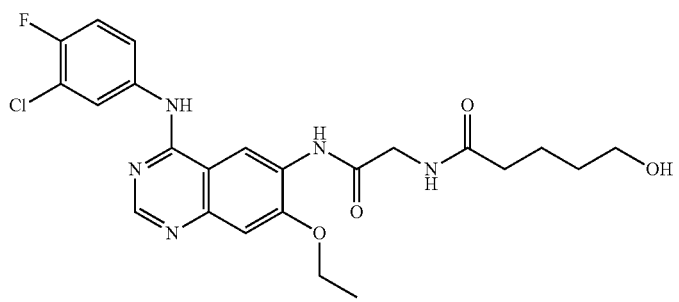

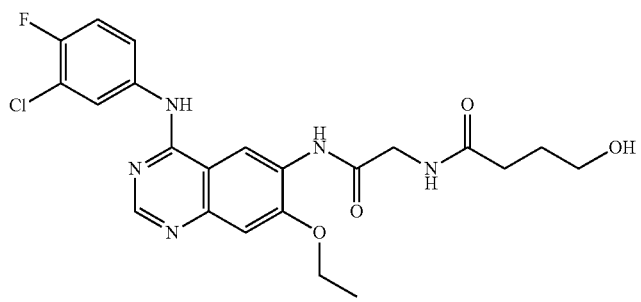
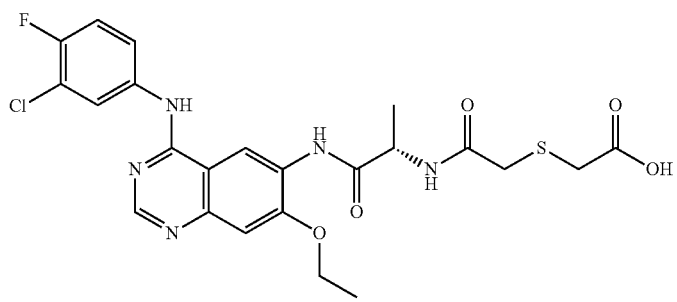
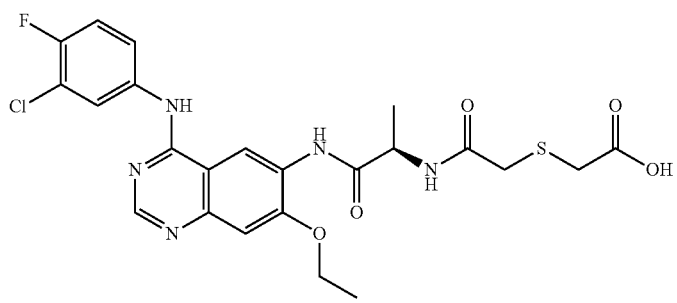
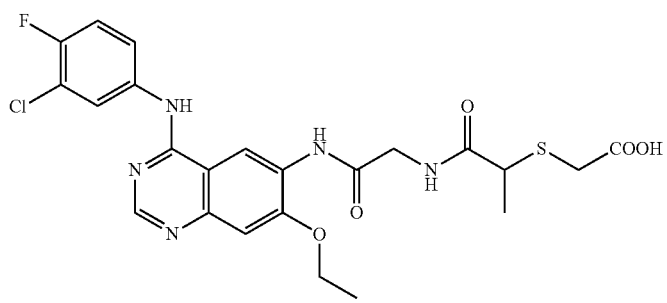
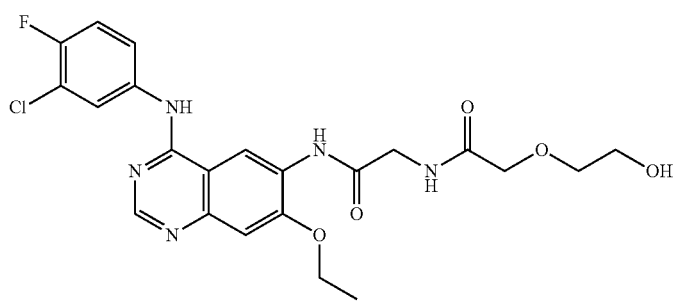

-continued
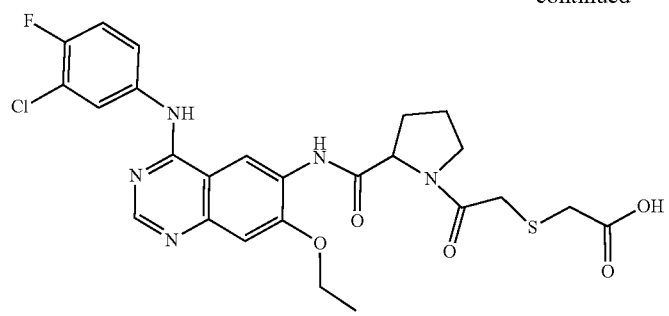
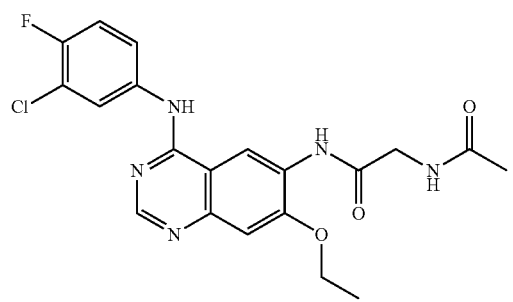
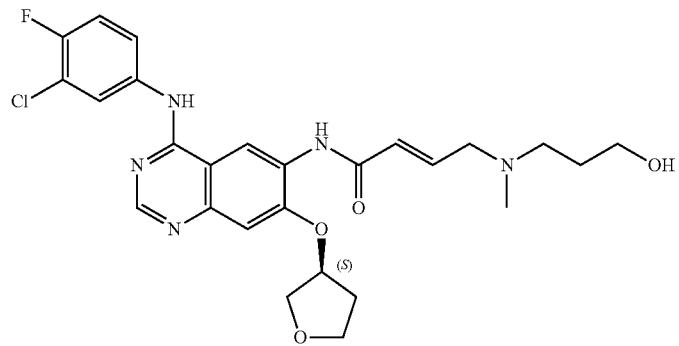
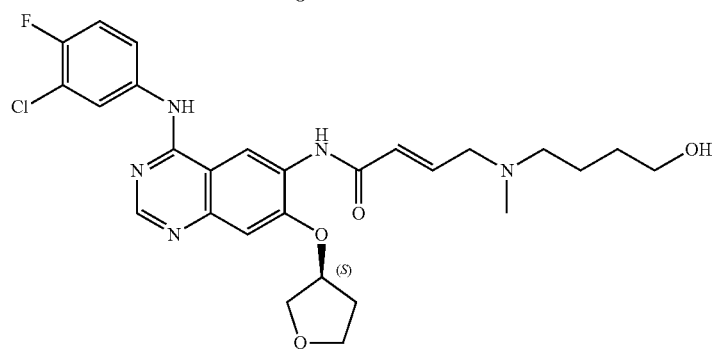
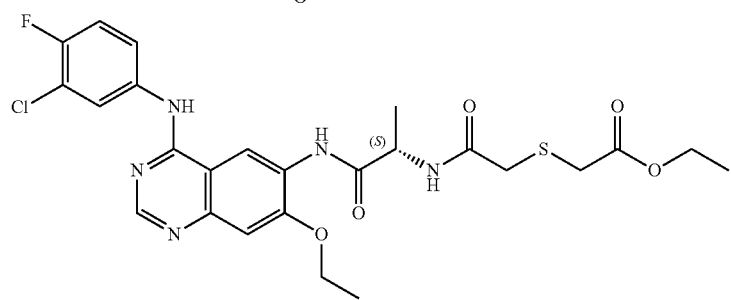

-continued
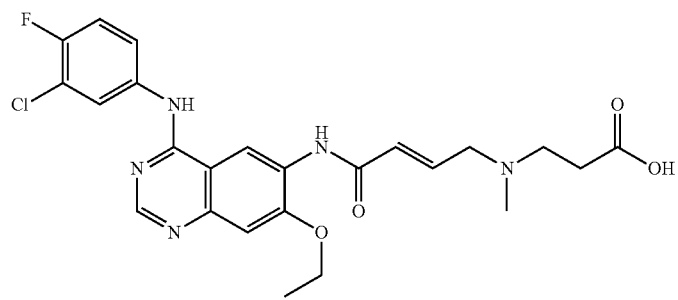
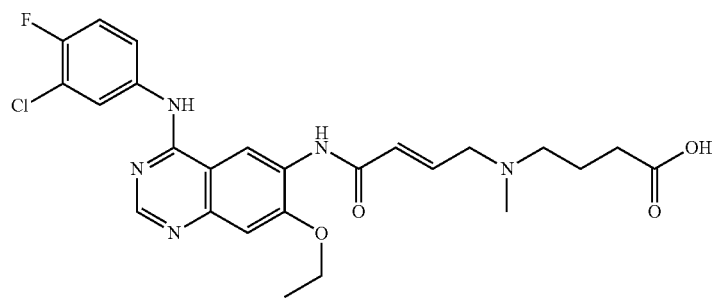
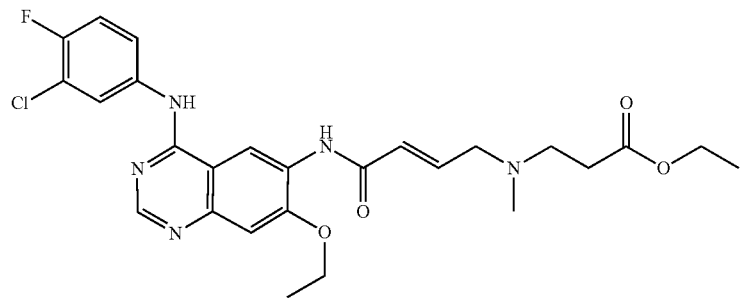
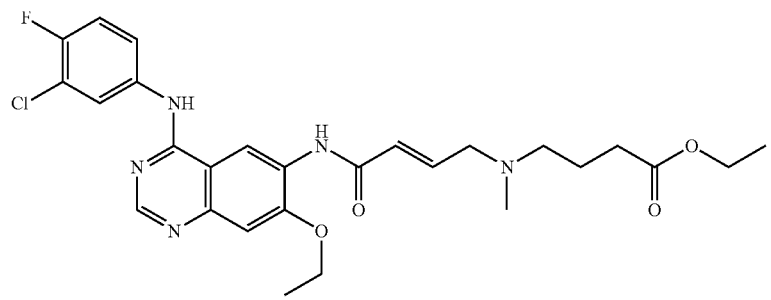
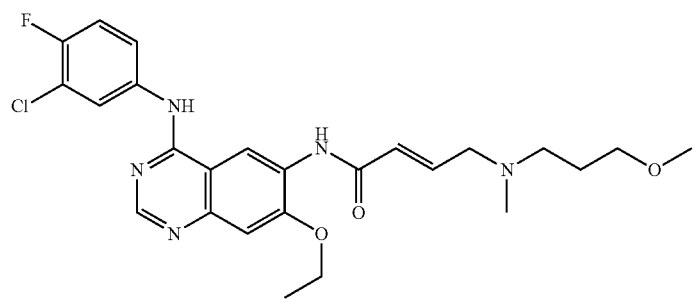

-continued

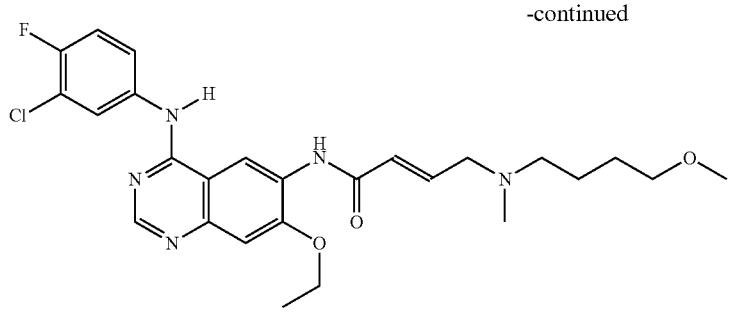

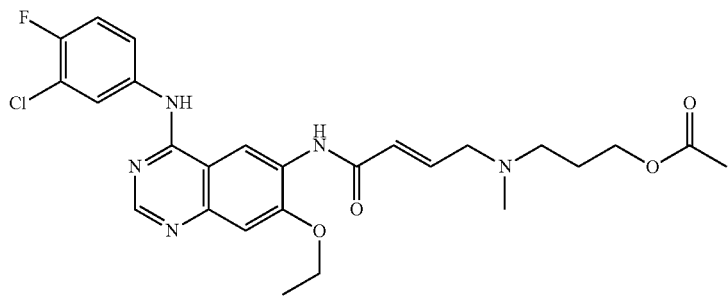 [SMILES: CCOc1cc2ncnc(Nc3ccc(F)c(Cl)c3)c2cc1NC(=O)/C=C/CN(C)CCCOC(C)=O]

or a pharmaceutically acceptable salt thereof.

In certain embodiments, a compound of the disclosure can have the following structure:

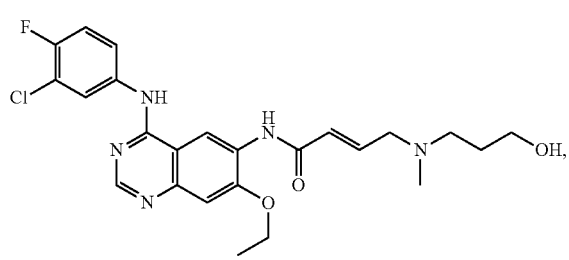 [SMILES: CCOc1cc2ncnc(Nc3ccc(F)c(Cl)c3)c2cc1NC(=O)/C=C/CN(C)CCCO]

or a pharmaceutically acceptable salt thereof.

In certain embodiments, a compound of the disclosure can have the following structure:

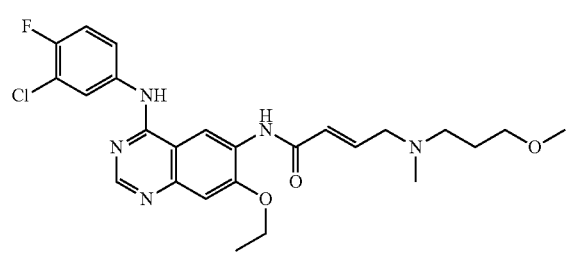 [SMILES: CCOc1cc2ncnc(Nc3ccc(F)c(Cl)c3)c2cc1NC(=O)/C=C/CN(C)CCCOC]

or a pharmaceutically acceptable salt thereof.

In certain embodiments, a compound of the disclosure can have the following structure:

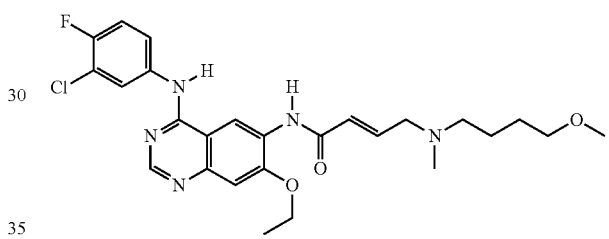

or a pharmaceutically acceptable salt thereof.

In certain embodiments, the present disclosure provides compounds of the formula (II),

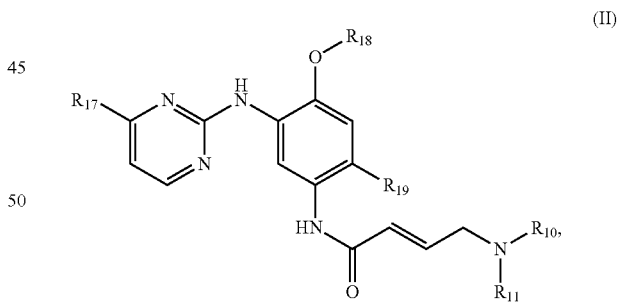

wherein $R_{10}$ is $C_{1-6}$ alkylcarboxylic acid, $C_{1-6}$ alkyl alcohol, $C_{1-6}$ alkyl ether, or $C_{1-6}$ alkyl ester;

$R_{11}$ is H, $C_{1-6}$ alkyl, $C_{1-6}$ alkyl alcohol, $C_{1-6}$ alkyl ether, or $C_{1-6}$ alkyl ester;

$R_{17}$ is optionally substituted aryl or optionally substituted heteroaryl;

$R_{18}$ is H or $C_{1-6}$ alkyl; and $R_{19}$ is H, optionally substituted amine, or optionally substituted diamine or a pharmaceutically acceptable salt thereof.

In certain embodiments, $R_{17}$ can be optionally substituted bicyclic aryl or optionally substituted bicyclic heteroaryl. In certain embodiments, $R_{17}$ can be optionally substituted indole.

In certain embodiments, a compound of the present disclosure can have the following structure:

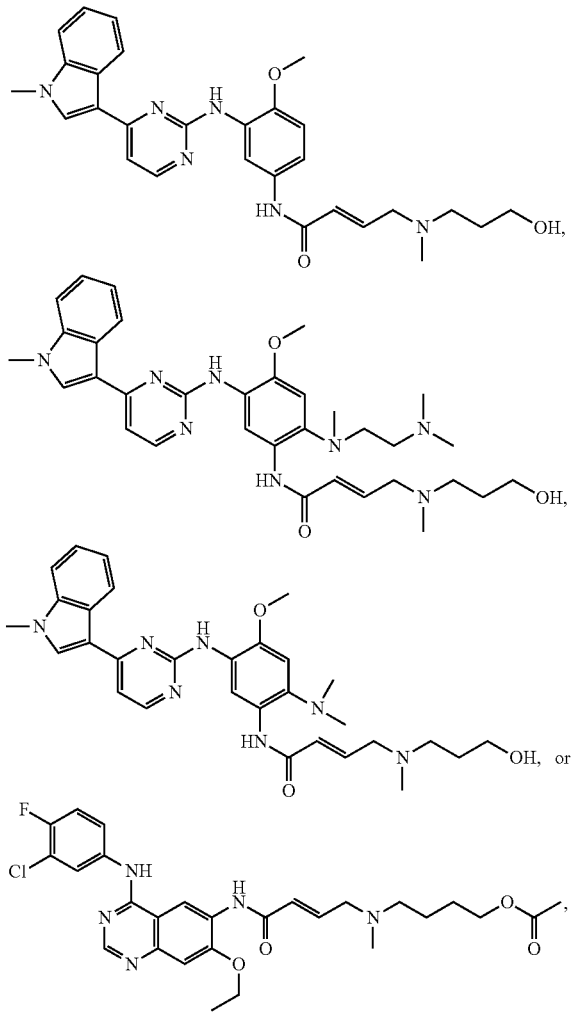

or a pharmaceutically acceptable salt thereof.

In certain embodiments, the present disclosure provides a compound for use in the treatment of cancer. In certain embodiments, the cancer can be a lung, head, neck, or pancreatic cancer. In certain embodiments, a compound of the disclosure is used in In certain embodiments, the present disclosure provides a method of treating cancer, comprising administering to a subject in need thereof a therapeutically effective amount of a compound of the disclosure or a pharmaceutically acceptable salt thereof. In certain embodiments, the cancer can be a lung, head, neck, or pancreatic cancer.

In certain embodiments, the present disclosure provides a pharmaceutical composition comprising a therapeutically effective amount of a compound of the disclosure or a pharmaceutically acceptable salt thereof, and one or more pharmaceutically acceptable carriers.

As used herein, the terms "compound of the disclosure" or "compounds of the disclosure" refers to any compound disclosed in the present application or a pharmaceutically acceptable salt thereof, such as a compound of formula (I) or formula (II) or a pharmaceutically acceptable salt thereof.

As used herein, the terms "halo" and "halogen" refer to fluoro, chloro, bromo or iodo.

As used herein, the term "$C_{1-6}$ alkyl" as used by itself or as part of another group refers to straight-chain and branched non-cyclic saturated hydrocarbons having from 1 to 6 carbon atoms. In certain embodiments, alkyl groups can be selected from straight chain ($C_1$-$C_6$)alkyl groups and branched chain ($C_3$-$C_6$)alkyl groups. ($C_3$-$C_6$)alkyl groups can be methyl, ethyl, propyl, isopropyl, butyl, sec-butyl, tert-butyl, iso-butyl, pentyl, 3-pentyl, hexyl, among others. In certain embodiments, alkyl groups can be straight chain ($C_2$-$C_6$)alkyl groups and branched chain ($C_3$-$C_6$)alkyl groups. ($C_2$-$C_6$)alkyl groups can be ethyl, propyl, isopropyl, butyl, sec-butyl, tert-butyl, iso-butyl, pentyl, 3-pentyl, hexyl among others. In certain embodiments, alkyl groups can be straight chain ($C_1$-$C_4$)alkyl groups and branched chain ($C_3$-$C_4$)alkyl groups. ($C_1$-$C_4$)alkyl groups can be methyl, ethyl, propyl, isopropyl, butyl, sec-butyl, tert-butyl, and iso-butyl.

As used herein, the term "$C_{2-6}$ alkenyl" as used by itself or as part of another group refers to straight chain and branched non-cyclic hydrocarbons having from 2 to 6 carbon atoms and including at least one carbon-carbon double bond. Straight chain and branched $C_{2-6}$ alkenyl groups can be vinyl, allyl, 1-butenyl, 2-butenyl, isobutylenyl, 1-pentenyl, 2-pentenyl, 3-methyl-1-butenyl, and the like. In certain embodiments, $C_{2-6}$ alkenyl groups can be $C_{2-4}$ alkenyl. $C_{2-4}$ alkenyl groups can be ethenyl, propenyl, isopropenyl, butenyl, and sec-butenyl.

As used herein, the term "$C_{2-6}$ alkynyl" as used by itself or as part of another group refers to straight chain and branched non-cyclic hydrocarbons having from 2 to 6 carbon atoms and including at least one carbon-carbon triple bond. Straight chain and branched $C_{2-6}$ alkynyl groups can be acetylenyl, propynyl, butyn-1-yl, butyn-2-yl, pentyn-1-yl, pentyn-2-yl, 3-methylbutyn-1-yl, pentyn-4-yl, hexyn-1-yl, hexyn-2-yl, hexyn-5-yl, and the like. $C_{2-6}$ alkynyl groups include include acetylenyl (i.e., ethynyl), propynyl, 1-butynyl, 2-butynyl, 1-pentynyl, 2-pentynyl, 3-methyl-1-butynyl, 4-pentynyl, and the like. In certain embodiments, the $C_{2-6}$ alkynyl group can be a $C_{2-4}$ alkynyl group. $C_{2-4}$ alkynyl groups can be ethynyl, propynyl, butynyl, and 2-butynyl groups.

As used herein, the term "$C_{1-6}$ alkylhydroxy" as used by itself or as part of another group can be any of the above-mentioned $C_{1-6}$ alkyl groups substituted by one or more hydroxy groups. $C_{1-6}$ alkylhydroxy groups can be hydroxymethyl, hydroxyethyl, hydroxypropyl and hydroxybutyl groups, for example, hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

As used herein, "cycloalkyl" groups can be selected from saturated cyclic hydrocarbon groups containing 1, 2, or 3 rings having from 3, 4, 5, 6, 7, 8, 9, 10, 11, or 12 carbon atoms (i.e., $C_{3-12}$ cycloalkyl). In certain embodiments, the cycloalkyl can have one or two rings. In certain embodiments, the cycloalkyl can be a $C_{3-8}$ cycloalkyl. In certain embodiments, the cycloalkyl can be a $C_{3-7}$ cycloalkyl. In certain embodiments, the cycloalkyl can be a $C_{3-6}$ cycloalkyl. In certain embodiments, the cycloalkyl group can be cyclopropyl, cyclobutyl, cyclopentyl, cyclohexyl, cycloheptyl, cyclooctyl, norbornyl, decalin, and adamantyl.

As used herein, the terms "heterocycle" or "heterocycloalkyl" as used by itself or as part of another group refer to a 3- to 12-membered monocyclic heterocyclic ring which is either saturated, or unsaturated, and non-aromatic. A 3-membered heterocycle can contain 1 heteroatom; a 4-membered heterocycle can contain 2 heteroatoms; a 5-membered heterocycle can contain 4 heteroatoms; a 6-membered heterocycle can contain 4 heteroatoms; and a 7-membered heterocycle can contain 5 heteroatoms. Each heteroatom can be independently selected from the group consisting of nitrogen (which can be quaternized), oxygen, and sulfur (including sulfoxide and sulfone). The (3- to 12-membered)heterocycle can be attached via a nitrogen or carbon atom. (3- to 12-membered)heterocycle groups can be thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, the term "$C_{1-6}$ alkoxy" as used by itself or as part of another group can be a straight chain or branched non-cyclic hydrocarbon having one or more ether groups and from 1 to 6 carbon atoms. Straight chain and branched $C_{1-6}$ alkoxy groups can be methoxy, ethoxy, propoxy, butyloxy, pentyloxy, hexyloxy, methoxymethyl, 2-methoxyethyl, 5-methoxypentyl, 3-ethoxybutyl, and the like.

As used herein, the term "aryl" can be $C_{6-14}$ aryl, for example $C_{6-10}$ aryl. $C_{6-14}$ aryl groups can ebe phenyl, naphthyl, phenanthryl, anthracyl, indenyl, azulenyl, biphenyl, biphenylenyl, and fluorenyl groups, for example phenyl, naphthyl, and biphenyl groups. In certain embodiments, the aryl group can be a (6- to 12-membered)aryl group.

As used herein, the term "heteroaryl" as used by itself or as part of another group can be an aromatic heterocycle ring of 5 to 12 members, including both mono- and bicyclic ring systems, where at least one carbon atom (of one or both of the rings) is replaced with a heteroatom independently selected from nitrogen, oxygen, and sulfur, or at least two carbon atoms of one or both of the rings are replaced with a heteroatom independently selected from nitrogen, oxygen, and sulfur. (5- to 12-membered)heteroaryl groups can be pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, thiadiazolyl, cinnolinyl, phthalazinyl, quinazolinyl, and the like.

As used herein, the term "amino" refers to —$NH_2$.
As used herein, the term "hydroxy" refers to —OH.
As used herein, the term "cyano" refers to —CN.
As used herein, the term "nitro" refers to —$NO_2$.
As used herein, the term "carboxylic acid" refers to —COOH.

Optional substituents on optionally substituted groups, when not otherwise indicated, include one or more groups, for example, 1, 2, or 3 groups, independently selected from the group consisting of halo, halo($C_{1-6}$)alkyl, aryl, heterocycle, cycloalkyl, $C_{1-6}$ alkyl, $C_{2-6}$ alkenyl, $C_{2-6}$ alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxy($C_{1-6}$)alkyl, amino($C_{1-6}$)alkyl, carboxy($C_{1-6}$)alkyl, alkoxy($C_{1-6}$)alkyl, nitro, amino, ureido, cyano, alkylcarbonylamino, hydroxy, thiol, alkylcarbonyloxy, aryloxy (e.g., phenoxy and benzyloxy), ar($C_{1-6}$)alkyloxy, carboxamido, sulfonamido, azido, $C_{1-6}$ alkoxy, halo($C_{1-6}$)alkoxy, carboxy, aminocarbonyl, (=O), and mercapto($C_{1-6}$)alkyl groups mentioned above. Preferred optional substituents include halo, halo($C_{1-6}$)alkyl, hydroxy($C_{1-6}$)alkyl, amino($C_{1-6}$)alkyl, hydroxy, nitro, $C_{1-6}$ alkyl, $C_{1-6}$ alkoxy, halo($C_{1-6}$)alkoxy, and amino.

Compounds of the disclosure encompass all the salts of the disclosed compounds of formula (I) or formula (II). The present disclosure includes all non-toxic pharmaceutically acceptable salts thereof of the disclosed compounds. In certain embodiments, pharmaceutically acceptable addition salts can be inorganic and organic acid addition salts and basic salts. In certain embodiments, pharmaceutically acceptable salts can be metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

In certain embodiments, compounds of the disclosure can contain one or more asymmetric centers and may thus give rise to enantiomers, diastereomers, and other stereoisomeric forms, such as epimers. The present disclosure is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present dicslosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral streogenic centres present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

As used herein, the terms "treating," "treat," or "treatment" refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response with or without excessive levels of side effects. Treatment can include inhibiting cell proliferation or the growth of tumors, or ameliorating the symptoms, prolonging the survival of, or otherwise mitigating the undesirable effects of the disease for which the patient is being treated. In certain embodiments, compounds of the disclosure can be used in combination with at least one other therapeutic agent.

Methods of Treatment and Pharmaceutical Compositions

Due to their activity, the compounds of the disclosure are advantageously useful in medicine. As described above, the compounds of the disclosure are useful for treating cancer in a subject in need thereof. The term "subject" as used herein refers to any animal that may experience the beneficial effects of a compound of the disclosure. Foremost such animals are mammals, e.g., humans and companion animals, although the disclosure is not intended to be so limited.

For detection of expression or activity of EGFR, a tissue (cancer tissue, blood vessel wall tissue, skin, oral mucosa etc.) or a body fluid (blood, lymph) and the like, which is obtained from a subject, can be applied to a test to detect expression or activity of EGFR. Such tests are known to those skilled in the art.

When administered to a subject, a compound of the disclosure can be administered as a component of a composition that comprises a pharmaceutically acceptable carrier or excipient. A compound of the disclosure can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (such as to the ears, nose, eyes, or skin). Delivery can be either local or systemic. In certain embodiments, administration can result in the release of a compound of the disclosure into the bloodstream.

Pharmaceutical compositions of the present disclosure can take the form of solutions, suspensions, emulsions, tablets, pills, pellets, powders, multi-particulates, capsules, capsules containing liquids, capsules containing powders, capsules containing multi-particulates, lozenges, sustained-release formulations, suppositories, transdermal patches, transmucosal films, sub-lingual tablets or tabs, aerosols, sprays, or any other form suitable for use. In one embodiment, the composition is in the form of a tablet. In certain embodiments, the composition can be in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the present disclosure can comprise a suitable amount of a pharmaceutically acceptable excipient so as to provide the form for proper administration to the subject. In certain embodiments, the pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. Auxiliary, stabilizing, thickening, lubricating, and coloring agents can be used. In certain embodiments, the pharmaceutically acceptable excipient can be sterile when administered to a subject. Water can be an excipient when a compound of the disclosure is administered intravenously. Saline solutions and aqueous dextrose and glycerol solutions can also be employed as liquid excipients, such as for injectable solutions. In certain embodiments, the pharmaceutical excipients can include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. In certain embodiments, the compositions can contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the compounds of the disclosure can be formulated for oral administration. A compound of the disclosure to be orally delivered can be in the form of tablets, capsules, gelcaps, caplets, lozenges, aqueous or oily solutions, suspensions, granules, powders, emulsions, syrups, or elixirs, for example. When a compound of the disclosure is incorporated into oral tablets, such tablets can be compressed, tablet triturates, enteric-coated, sugar-coated, film-coated, multiply compressed or multiply layered.

An orally administered a compound of the disclosure can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980). Liquid oral dosage forms can include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a compound of the disclosure is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a compound of the disclosure is to be injected parenterally, it can be, e.g., in the form of an isotonic sterile solution. A compound of the disclosure can also be in the form of a powder for reconstitution as an injectable formulation.

In certain embodiments, a compound of the disclosure can be formulated into a pharmaceutical composition for intravenous administration. In certain embodiments, such compositions comprise sterile isotonic aqueous buffer. In certain embodiments, the compositions can include a solubilizing agent. A compound of the disclosure for intravenous administration can include a local anesthetic such as benzocaine or prilocaine to lessen pain at the site of the injection. In certain embodiments, the ingredients can be supplied either separately or mixed together in unit dosage form, for example, as a dry lyophilized powder or water free concentrate in a hermetically sealed container such as an ampule or sachette indicating the quantity of active agent. Where a compound of the disclosure is to be administered by infusion, it can be dispensed, for example, with an infusion bottle containing sterile pharmaceutical grade water or saline. Where a compound of the disclosure is administered by injection, an ampule of sterile water for injection or saline can be provided so that the ingredients can be mixed prior to administration.

When a compound of the disclosure is to be administered by inhalation, it can be formulated into a dry aerosol, or an aqueous or partially aqueous solution.

In another embodiment, a compound of the disclosure can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a compound of the disclosure can be administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a compound of the disclosure can be delivered in an immediate release form. In other embodiments, a compound of the disclosure can be delivered in a controlled-release system or sustained-release system. Controlled- or sustained-release pharmaceutical compositions can have a common goal of improving drug therapy over the results achieved by their non-controlled or non-sustained-release counterparts. In certain embodiments, a controlled- or sustained-release composition can comprise a minimal amount of a compound of the disclosure to treat in a minimum amount of time. Advantages of controlled- or sustained-release compositions include extended activity of the drug, reduced dosage frequency, and increased compliance. Controlled- or sustained-release compositions can favorably affect the time of onset of action or other characteristics, such as blood levels of the compound of the disclosure, and can thus reduce the occurrence of adverse side effects.

Controlled- or sustained-release compositions can initially immediately release an amount of a compound of the disclosure that promptly produces the desired therapeutic effect, and gradually and continually release other amounts of the compound of the disclosure to maintain a level of therapeutic effect over an extended period of time. To maintain a constant level of the compound of the disclosure in the body, the compound of the disclosure can be released from the dosage form at a rate that will replace the amount of compound of the disclosure being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present disclosure can be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with compounds of the disclosure in view of this disclosure.

When in tablet or pill form, a pharmaceutical composition of the invention can be coated to delay disintegration and absorption in the gastrointestinal tract, thereby providing a sustained action over an extended period of time. Selectively permeable membranes surrounding an osmotically active driving compound can be suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include excipients such as mannitol, lactose, starch, magnesium stearate, sodium saccharin, cellulose, and magnesium carbonate. In certain embodiments, the excipients can be of pharmaceutical grade.

The amount of the compound of the disclosure that is effective for the treatment of cancer can be determined by standard clinical techniques. In addition, in vitro and/or in vivo assays can be employed to help identify optimal dosage ranges. The precise dose to be employed can also depend on, e.g., the route of administration and the extent of the cancer to be treated, and can be decided according to the judgment of a practitioner and/or each subject's circumstances. Variations in dosing can occur depending upon typical factors such as the weight, age, sex, and physical condition (e.g., hepatic and renal function) of the subject being treated, the cancer to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the subject per day. In certain embodiments, the suitable effective dosage amounts can be from about 0.01 mg/kg of body weight to about 2500 mg/kg of body weight of the subject per day or from about 0.01 mg/kg of body weight to about 1000 mg/kg of body weight of the subject per day. In certain embodiments, the effective dosage amount can be about 100 mg/kg of body weight of the subject per day or less. In certain embodiments, the effective dosage amount can range from about 0.01 mg/kg of body weight to about 100 mg/kg of body weight of the subject per day of a compound of the disclosure, in another embodiment, about 0.02 mg/kg of body weight to about 50 mg/kg of body weight of the subject per day, and in another embodiment, about 0.025 mg/kg of body weight to about 20 mg/kg of body weight of the subject per day. Administration can be as a single dose or as a divided dose.

According to the present invention, methods for treating cancer in a subject in need thereof can further comprise co-administering to the subject an effective amount of a second therapeutic agent in addition to a compound of the disclosure (i.e., a first therapeutic agent). An effective amount of the second therapeutic agent can be known or determinable by a medical practitioner in view of this disclosure and published clinical studies. In one embodiment of the present disclosure a second therapeutic agent can be administered to a subject for treatment of a cancer. In this embodiment, the compound of the disclosure and the second therapeutic agent can act either additively or synergistically to treat cancer. Alternatively, the second therapeutic agent can be used to treat a disorder that is different from cancer. In certain embodiments, a compound of the disclosure can be administered concurrently with a second therapeutic agent as a single composition comprising an effective amount of a compound of the disclosure and an effective amount of the second therapeutic agent. In certain embodiments, an effective amount of a compound of the disclosure can be administered prior or subsequent to administration of an effective amount of the second therapeutic agent. In this embodiment, the compound of the disclosure can administered while the second therapeutic agent exerts its therapeutic effect, or the second therapeutic agent is administered while the compound of the disclosure exerts its therapeutic effect for treating of cancer.

Exemplary anti-cancer drugs include Erlotinib, Gefitinib, Lapatinib, or any compound having a structure in U.S. Pat. Nos. 5,747,498; 6,900,221; 7,087,613; RE41065 (corresponding to Erlotinib); U.S. Pat. Nos. 5,457,105; 5,616,582; 5,770,599 (corresponding to Gefitinib); U.S. Pat. Nos. 6,391,874; 6,713,485; 6,727,256; 6,828,320; and 7,157,466 (corresponding to Lapatinib). When administered in combination with such an anti-cancer drug, the ratio of the anti-cancer drug to a compound of disclosure can be in the range of about 1:100 to about 100:1. Independent embodiments provide that this range may be about 1:10 to about 10:1, about 1:5 to about 5:1, about 1:2 to about 2:1, or about 1:1.

The second therapeutic agent can be, but is not limited to, an opioid agonist, a non-opioid analgesic, a non-steroidal anti-inflammatory agent, an antimigraine agent, a Cox-IA inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

EXAMPLES

The compounds, compositions, and methods described herein are now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

Example 1: MTT Assay Protocol

An MTT assay can be performed to screen compounds for suitability as an EGFR inhibitor. A sample MTT assay protocol is as follows:

Seed 50 μl cells in microplates and ensure a reasonable cell density yielding a strong control signal. SKBR3, BT474, MDA-MB-231, MDA-MB-453, MDA-MB-468, Ml: 5000 cells/well, 5% FBS; NE91, NR6 and NR6 derived cell lines: 2500 cells/well, 5% FBS; H1975: 5000 cells/well, 1% FBS).

Add 50 μl medium with different concentrations of inhibitors. Incubate at 37° C., 5% $CO_2$ for 72 hrs.

Replace the medium with 100 μl of fresh medium. Leave at 37° C., 5% $CO_2$ for 4 hrs.

Add 25 μl of MIT (5 mg/ml stock solution, final concentration 1 mg/ml) to each well. Incubate the microtrays for 2 hours at 37° C.

Add 100 μl extraction buffer (50% DMF/20% SDS at pH 4.7) to each well.

Incubate overnight at 37° C. and OD measurements at 570 nm.

A MTT assay protocol is also described in Hansen et al., "Re-examination and further development of a precise and rapid dye method for measuring cell growth/cell kill," *J. Immunol. Methods* 119:203-210 (1989).

Example 2: RBC HotSpot Kinase Assay Protocol

An RBC HotSpot Kinase Assay can be performed to determine kinase activity data. A sample RBC HotSpot KinaseAssay protocol is as follows:

Reagent: Base Reaction buffer; 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO Add required cofactors individually to each kinase reaction.

Compound handling: Dissolve testing compounds in 100% DMSO to specific concentration. Serial dilution can be conducted using Integra Viaflo Assist in DMSO.

Reaction Procedure:

Prepare substrate in freshly prepared Reaction Buffer.

Deliver any required cofactors to the substrate solution above.

Deliver kinase into the substrate solution and gently mix.

Deliver compounds in 100% DMSO into the kinase reaction mixture by Acoustic technology (Echo550; nanoliter range) and incubate for 20 min at room temp.

Deliver $^{33}$P-ATP (Specific activity 10 µCi/µl) into the reaction mixture to initiate the reaction.

Incubate for 2 hours at room temperature.

Detect radioactivity by filter-binding method.

Kinase activity data can be expressed as the percent remaining kinase activity in test samples compared to vehicle (dimethyl sulfoxide) reactions. IC$_{50}$ values and curve fits can be obtained using Prism (GraphPad Software).

Another suitable assay for determining kinase inhibitor selectivity is disclosed in Anastassiadis et al., "Comprehensive assay of kinase catalytic activity reveals features of kinase inhibitor selectivity," *Nature Biotechnology* 29(11): 1039-1045 (2011), which is incorporated by reference herein.

Example 3: Synthesis of SGI-078

Synthesis route for SGI-078 is represented in FIG. 1. The synthesis may be achieved with the following steps:

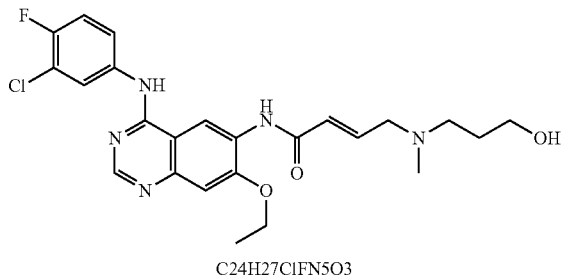

SGI-078

C24H27ClFN5O3

1) Preparation of Compound 003-2

To a solution of compound 003-1 (15 g, 71.73 mmol) in 150 mL of ethanol was cooled to 0° C. and added slowly sodium ethoxide (10.74 g, 157.81 mmol). Then the mixture was refluxed for 2 h (monitored by LCMS). The solvent was evaporated and the solution was neutralized with HCl aqueous solution to pH=2~3. The solid was filtered, and the cake was collected and dried in vacuo to give compound 003-2 (14 g, 83% yield) as a yellow solid.

2) Preparation of Compound 003-3

To a solution of compound 003-2 (14 g, 59.52 mmol), DMF (474 mg, 6.49 mmol) in 250 mL round-bottom flask was cooled to 0° C. and added dropwise 120 mL of thionyl chloride. Then the mixture was stirred at RT for 4 h (monitored by LCMS). The solvent was evaporated and 50 mL of PE:EA=3:1 was add and stirred at RT for 1 h. The solid was filtered and the cake was collected and dried in vacuo to give compound 003-3 (11 g, 72.8% yield) as a yellow solid.

3) Preparation of Compound 003-4

To a solution of compound 003-3 (11 g, 43.37 mmol) and 3-chloro-4-fluoroaniline (6.94 g, 47.71 mmol) in 100 mL of isopropanol was refluxed for 1 h (Checked by LCMS and TLC). The solid was filtered, and the cake was collected and dried in vacuo to give compound 003-4 (14 g, 89% yield) as a yellow solid.

4) Preparation of Compound 003-5

To a solution of compound 003-4 (14 g, 38.6 mmol), iron powder (12.1 g, 216.16 mmol), glacial acetic acid (11 g, 184 mmol) in 80 mL of ethanol and 40 mL of water was refluxed for 1.5 h (Checked by LCMS and TLC). The solvent was evaporated and the solution was neutralized with Na$_2$CO$_3$ aqueous solution to pH=9~10. It was extracted with DCM (80 mL×5), brine (50 mL×1), dried over Na$_2$SO$_4$ and concentrated in vacuo to give compound 003-5 (10 g, 77.9% yield) as a faint yellow solid.

5) Preparation of Compound 078-2

To a solution of compound 078-1 (1.2 g, 7.27 mmol), DMF (20 mg, 0.27 mmol) in 25 mL of DCM was cooled to 0° C. and added dropwise oxalyl chloride (1.2 g, 9.45 mmol). Then the mixture was stirred at RT for 1 h. The reaction mixture was dried in vacuo to give compound 078-2 (1.6 g (crude)) as a yellow oil used for the next step.

6) Preparation of Compound 078-4

To a solution of compound 078-3 (1.0 g, 11.22 mmol), imizadole (1.15 g, 16.83 mmol) in 20 mL of DCM was cooled to 0° C. and added slowly tert-butyldimethylsilyl chloride (2.03 g, 13.46 mmol). Then the mixture was stirred at RT for overnight. The residue was purified by flash column chromatography of silica gel (PE/EtOAc=20:1) to give compound 078-4 (1.2 g, 52.6% yield) as a yellow oil.

7) Preparation of Compound 078-5

To a solution of compound 003-5 (2 g, 6.01 mmol) and triethylamine (1.52 g, 15.03 mmol) in 15 mL of DMF was added dropwise a solution of compound 078-2 (1.6 g(crude)) in 5 mL of DMF. Then the reaction mixture was stirred at RT for 2 h under N$_2$ (Checked by LCMS). 20 mL of water was added and extracted with EtOAc (40 mL×2), washed with water (20 mL×3), brine (20 mL×1), dried over Na$_2$SO$_4$ and concentrated in vacuo. The residue was purified by flash column chromatography of silica gel using DCM to give compound 078-5 (2.5 g, 86.5%) as a yellow oil.

8) Preparation of Compound 078-6

To a solution of compound 078-5 (1.5 g, 3.13 mmol) and triethylamine (475 mg, 4.7 mmol) in 15 mL of THF was added compound 078-4 (866 mg, 3.76 mmol). Then the mixture was stirred at RT for overnight (Checked by LCMS). The reaction mixture was extracted with EtOAc (20 mL×2), washed with water (10 mL×1), brine (20 mL×1), dried over Na$_2$SO$_4$ and concentrated in vacuo to give compound 078-6 (2 g, (crude)) as a yellow oil used for the next step.

9) Preparation of SGI-078

To a solution of compound 078-6 (2 g (crude)) in 20 mL of methanol was cooled to 0° C. and added dropwise 4N HCl (2 mL). Then the mixture was stirred at RT for 1.5 h (Checked by LCMS). The crude mixture was purified by prep-HPLC to give SGI-078 (210 mg, 11.2%, total yield of two steps) as a faint yellow solid.

Example 4: Synthesis of SGI-105 and SGI-106

Figure 2:
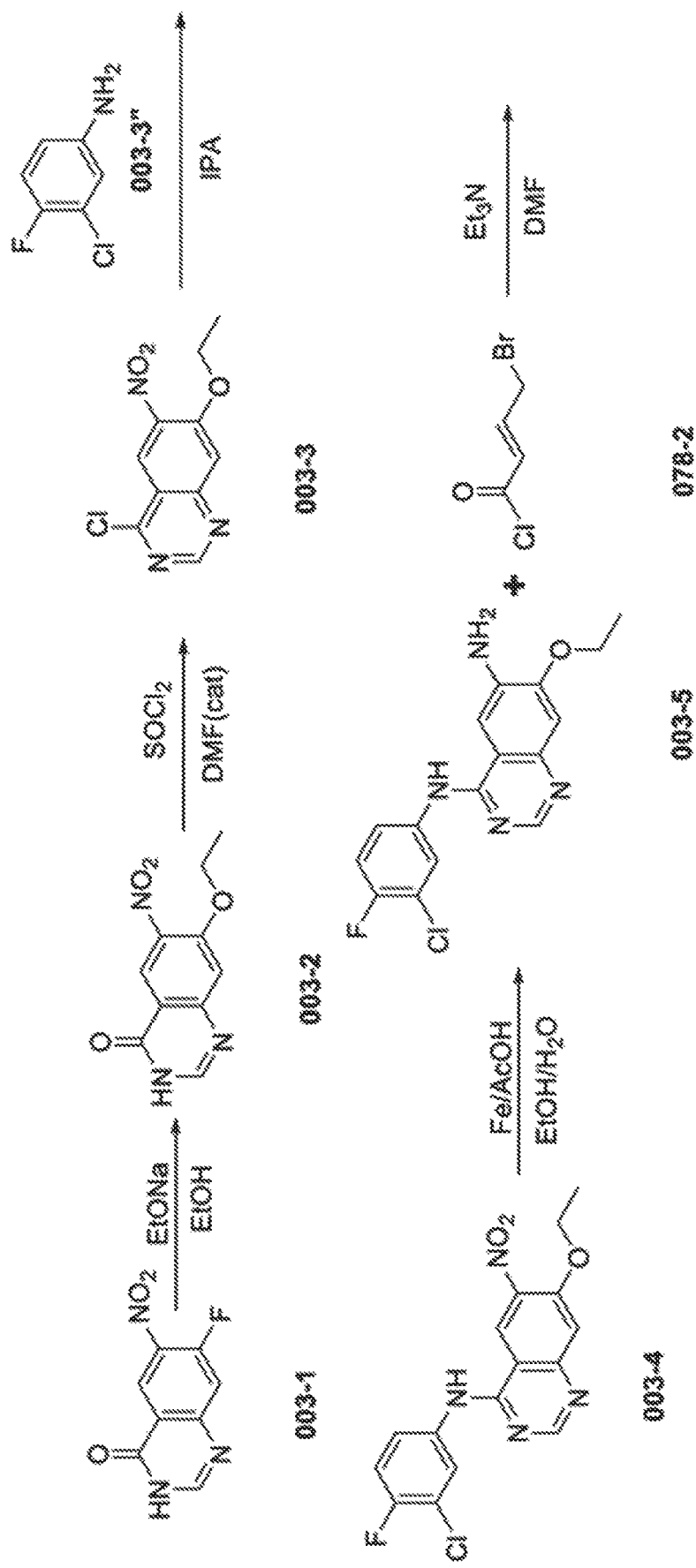
FIG. 2 shows the synthesis route of a representative compounds of SGI-105 and SGI-106.
Figure 2:
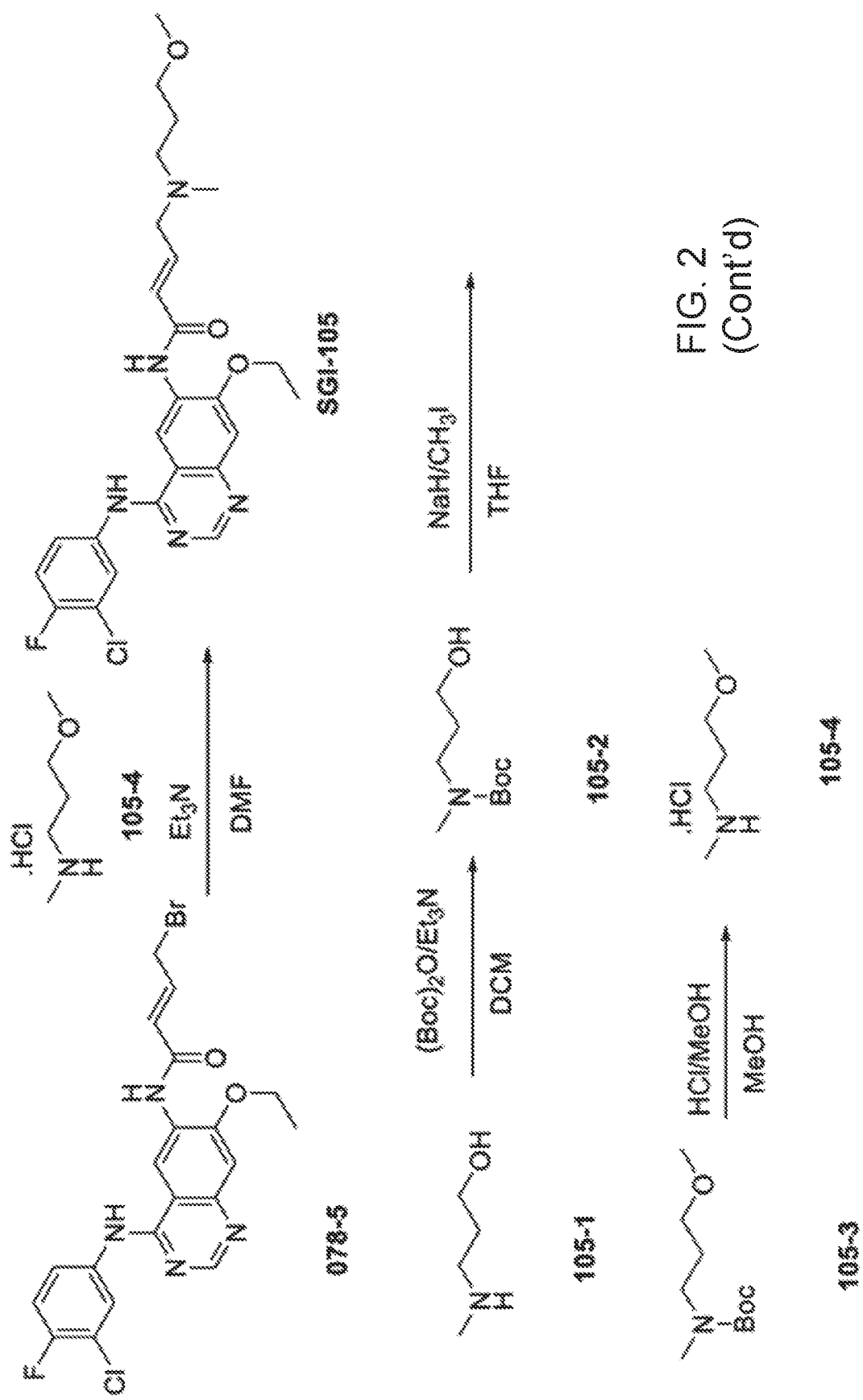
Figure 2:
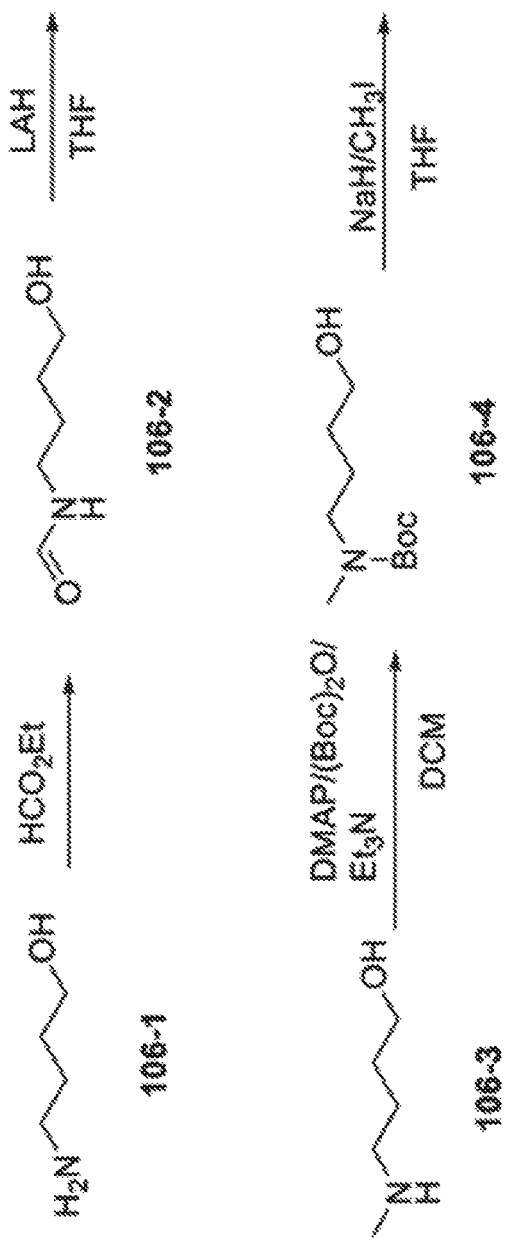
Figure 2:
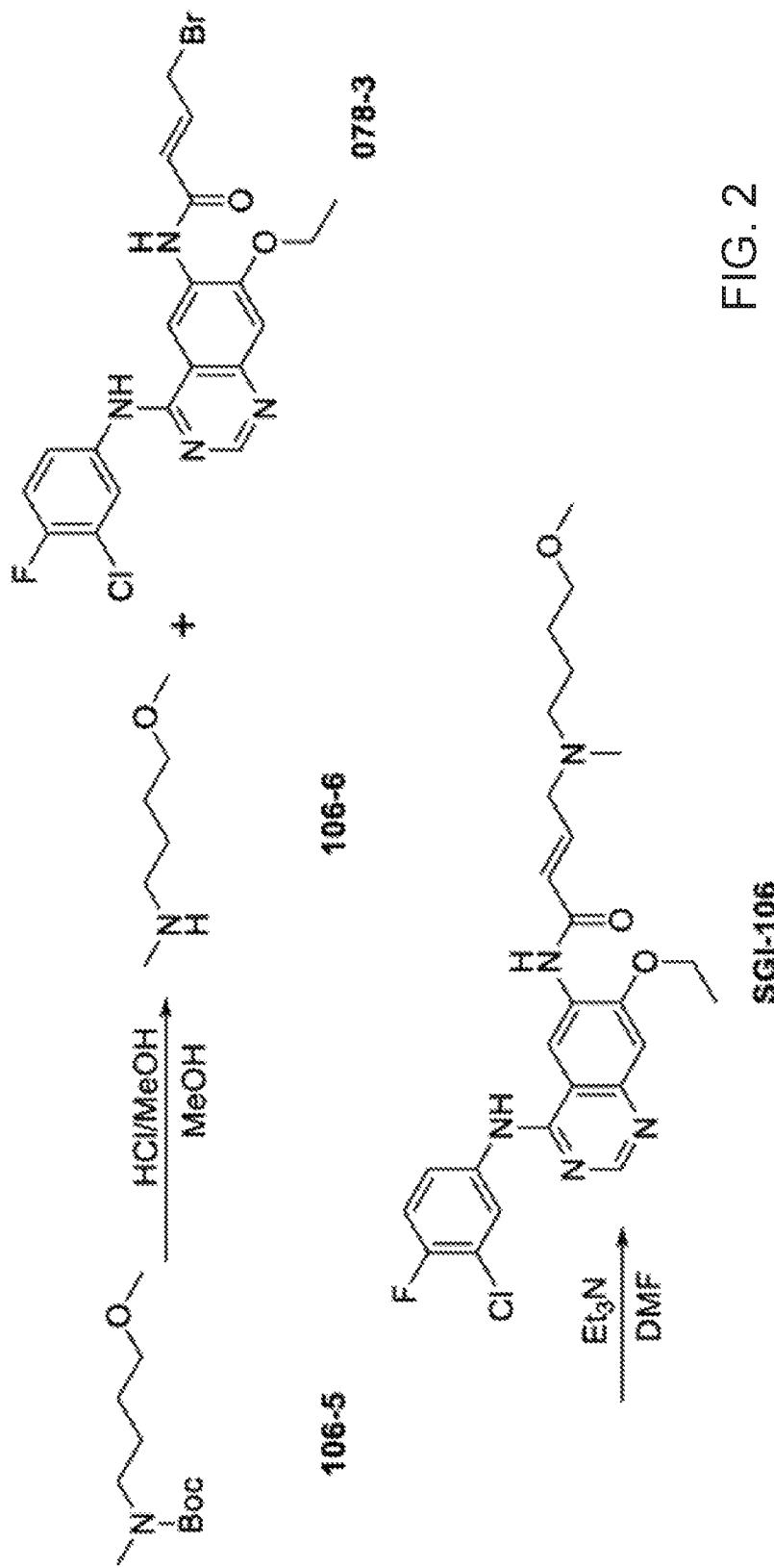

Synthesis route for SGI-105 and SGI-106 is represented in FIG. 2. The synthesis may be achieved with the following steps:

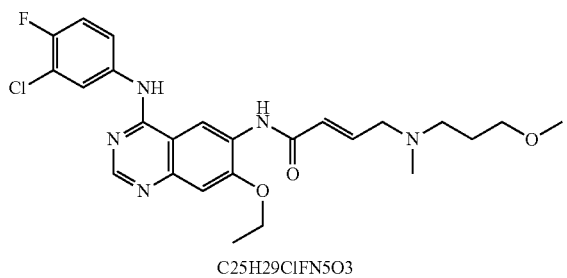

SGI-105

C25H29ClFN5O3

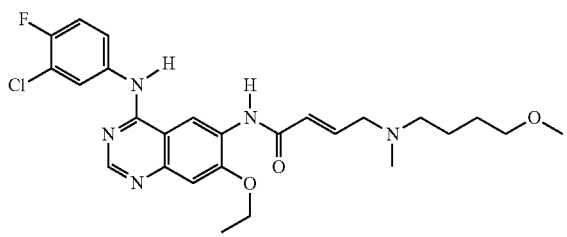 [SMILES: CCOc1cc2ncnc(Nc3ccc(F)c(Cl)c3)c2cc1NC(=O)/C=C/CN(C)CCCCOC]

SGI-106

1) Preparation of Compound 003-2

To a solution of compound 003-1 (15 g, 71.73 mmol) in 150 mL of ethanol was cooled to 0° C. and added slowly sodium ethoxide (10.74 g, 157.81 mmol). Then the mixture was refluxed for 2 h (Checked by LCMS). It was evaported and the solution was neutralized with aq.HCl to pH=2~3. The solid was filtered, and the cake was collected and dried in vacuo to give compound 003-2 (14 g, 83% yield) as a yellow solid.

2) Preparation of Compound 003-3

To a solution of compound 003-2 (14 g, 59.52 mmol), DMF (474 mg, 6.49 mmol) in 250 mL round-bottom flask was cooled to 0° C. and added dropwise 120 mL of thionyl chloride. Then the mixture was stirred at RT for 4 h (Checked by LCMS). It was evaporated and 50 mL of PE:EA=3:1 was add and stirred at RT for 1 h. The solid was filtered, and the cake was collected and dried in vacuo to give compound 003-3 (11 g, 72.8% yield) as a yellow solid.

3) Preparation of Compound 003-4

To a solution of compound 003-3 (11 g, 43.37 mmol) and 3-chloro-4-fluoroaniline (6.94 g, 47.71 mmol) in 100 mL of isopropanol was refluxed for 1 h (Checked by LCMS and TLC). The solid was filtered, and the cake was collected and dried in vacuo to give compound 003-4 (14 g, 89% yield) as a yellow solid.

4) Preparation of Compound 003-5

To a solution of compound 003-4 (14 g, 38.6 mmol), iron powder (12.1 g, 216.16 mmol), glacial acetic acid (11 g, 184 mmol) in 80 mL of ethanol and 40 mL of water was refluxed for 1.5 h (Checked by LCMS and TLC). It was evaporated and the solution was neutralized with aq.$Na_2CO_3$ to pH=9~10 and extracted with DCM (80 mL×5), brine (50 mL×1), dried over $Na_2SO_4$ and concentrated in vacuo to give compound 003-5 (10 g, 77.9% yield) as a faint yellow solid.

5) Preparation of Compound 078-2

To a solution of compound 078-1 (1.2 g, 7.27 mmol), DMF (20 mg, 0.27 mmol) in 25 mL of DCM was cooled to 0° C. and added dropwise oxalyl chloride (1.2 g, 9.45 mmol). Then the mixture was stirred at RT for 1 h. The reaction mixture was dried in vacuo to give compound 078-2 (1.6 g (crude)) as a yellow oil used for the next step.

6) Preparation of Compound 078-5

To a solution of compound 003-5 (2 g, 6.01 mmol) and triethylamine (1.52 g, 15.03 mmol) in 15 mL of DMF was added dropwise a solution of 078-2(1.6 g(crude)) in 5 mL of DMF. Then the reaction mixture was stirred at RT for 2 h under $N_2$. Checked by LCMS. 20 mL of water was added and extracted with EtOAc (40 mL×2), washed wih water (20 mL×3), brine (20 mL×1), dried over $Na_2SO_4$ and concentrated in vacuo. The residue was purified by flash column chromatography using DCM as eluent on silica gel to give compound 078-5 (2.5 g, 86.5%) as a yellow oil.

7) Preparation of Compound 105-2

To a solution of compound 105-1 (1.0 g, 11.22 mmol) and triethylamine (2.27 g, 22.44 mmol) in 15 mL of DCM was cooled to 0° C. and added dropwise di-tert-butyl dicarbonate (2.94 g, 13.46 mmol). Then the mixture was stirred at RT for 1.5 h (Checked by TLC). The reaction mixture was extracted with DCM (15 mL×2), washed with water (10 mL×1), brine (20 mL×1), dried over $Na_2SO_4$ and concentrated in vacuo. The residue was purified by flash column chromatography (PE/EA=2:1) on silica gel to give compound 105-2 (1.1 g, 51.9%) as a white oil.

8) Preparation of Compound 105-3

To a suspension of sodium hydride (109 mg, 7.55 mmol) in 10 mL of THF was cooled to 0° C. and added dropwise a solution of compound 105-2 (1.1 g, 5.81 mmol) in 15 mL THF. Then the mixture was stirred at 0° C. for 0.5 h. Iodomethane (990 mg, 6.97 mmol) was added slowly, and the mixture was stirred at RT for 1.5 h (Checked by TLC). The reaction mixture was extracted with EtOAc (20 mL×2), washed with water (10 mL×1), brine (20 mL×1), dried over $Na_2SO_4$ and concentrated in vacuo. The residue was purified by flash column chromatography (PE/EA=20:1) on silica gel to give 105-3 (700 mg, 59.3%) as a white oil.

9) Preparation of Compound 105-4

To a solution of compound 105-3 (700 mg, 3.44 mmol) in 10 mL of methanol was cooled to 0° C. and added dropwise 4N HCl (2 mL). Then the mixture was stirred at RT for 1.5 h (Checked by LCMS). The reaction mixture was dried in vacuo to give compound 105-4 (550 mg (crude)) as a white oil used for the next step.

10) Preparation of Compound 105

To a solution of compound 078-5 (1.1 g, 2.3 mmol) and triethylamine (475 mg, 4.6 mmol) in 15 mL of DMF was added 105-4 (550 mg (crude)). Then the mixture was stirred at RT for overnight (Checked by LCMS). The crude mixture was purified by preparative TLC (DCM/MeOH=20:1) to give SGI-105 (120 mg, 10.3%) as a faint yellow solid.

10) Preparation of Compound 106-2

To a solution of compound 106-1 (5 g, 56 mmol) in 50 mL of ethanol was and ethyl formate (7.2 g, 84 mmol). Then the mixture was refluxed for 18 h (Checked by TLC). The reaction mixture was dried in vacuo and purified by flash column (PE/EtOAc=10:1) on silica gel to give compound 106-2 (4.1 g, 62.4%) as an oil.

11) Preparation of Compound 106-3

To a suspension of Lithium aluminium hydride (2 g, 52.5 mmol) in 30 mL of THF was and a solution of compound 106-2 (4.1 g, 35 mmol). Then the mixture was refluxed for 2 h (Checked by TLC). 10 mL of water was added and filtered, the filtrate was collected and concentrated in vacuo and purified by flash column (PE/EtOAc=10:1) on silica gel to give compound 106-3 (2 g, 55.6%) as an oil.

12) Preparation of Compound 106-4

To a solution of compound 106-3 (1.0 g, 9.7 mmol), triethylamine (1.96 g, 19.4 mmol) and N,N-dimethylpyridin-4-amine (109 mg, 0.97 mmol) in 15 mL of DCM was cooled to 0° C. and added drop-wise di-tert-butyl dicarbonate (2.54 g, 11.64 mmol). Then the mixture was stirred at RT for 1.5 h (Checked by TLC). The reaction mixture was extracted with DCM (15 mL×2), washed with water (10 mL×1), brine (20 mL×1), dried over $Na_2SO_4$ and concentrated in vacuo. The residue was purified by flash column (PE/EtOAc=2:1) on silica gel to give compound 106-4 (1.2 g, 60.9%) as an oil.

13) Preparation of Compound 106-5

To a suspension of sodium hydride (354 mg, 8.85 mmol) in 10 mL of THF was cooled to 0° C. and added drop-wise a solution of compound 106-4 (1.2 g, 5.9 mmol) in 15 mL THF. Then the mixture was stirred at 0° C. for 0.5 h. Iodomethane (1.51 g, 10.62 mmol) was added slowly. Then the mixture was stirred at RT for 1.5 h (Checked by TLC). The reaction mixture was extracted with EtOAc (20 mL×2), washed with water (10 mL), brine (20 mL×1), dried over $Na_2SO_4$ and concentrated in vacuo. The residue was purified by flash column chromatography (PE/EtOAc=20:1) on silica gel to give compound 106-5 (600 mg, 46.9%) as an oil.

14) Preparation of Compound 106-6

To a solution of compound 106-5 (600 mg, 2.76 mmol) in 10 mL of methanol was cooled to 0° C. and added drop-wise 4N HCl (2 mL). Then the mixture was stirred at RT for 1.5 h (Checked by LCMS). The reaction mixture was dried in vacuo to give compound 106-6 (500 mg (crude)) as an oil used for the next step.

15) Preparation of Compound 106

To a solution of compound 078-5 (500 mg, 1.04 mmol) and triethylamine (210 mg, 2.08 mmol) in 10 mL of DMF was added compound 106-6 (500 mg, crude). Then the mixture was stirred at RT for overnight (Checked by LCMS). The crude mixture was purified by preparative TLC (DCM/MeOH=20:1) to give SGI-106 (23 mg, 4.3%) as a faint yellow solid.

Example 4: Activity of Different Inhibitors Against Various EGFR Mutants

Activity of different inhibitors against various EGFR mutants in the presence of 10 μM ATP is shown in FIG. 3. Both SGI-078 and SGI-105 show very strong activity against EGFR(C797S) and good activity on EGFR(d746-750/T790M/C797 S) and EGFR(L858R/T790M/C797S). Essays conducted as outlined in Examples 1 and 2.

Example 5: Determination of IC50 of Exemplary EGFR Kinase Inhibitors

In vitro proliferation of A431 and NCI-1975 cells to determine IC50 for EGFR kinase inhibitors in shown in FIG. 4. Both SGI-078 and SGI-105 have weak activity against A431 cells, which express the wild type EGFR, and better activity against NCI-H1975 cells, which express the EGFR (T790M) mutant. SG1-105 is more active than SGI-078 in the inhibition of HCI-H1975 cell proliferation. SGI-105 is even slightly better than AZD-9291 (181 nM vs. 260 nM). Essays conducted as outlined in Examples 1 and 2.

Example 6: Determination of IC50 of Exemplary EGFR Kinase Inhibitors

Figure 5:
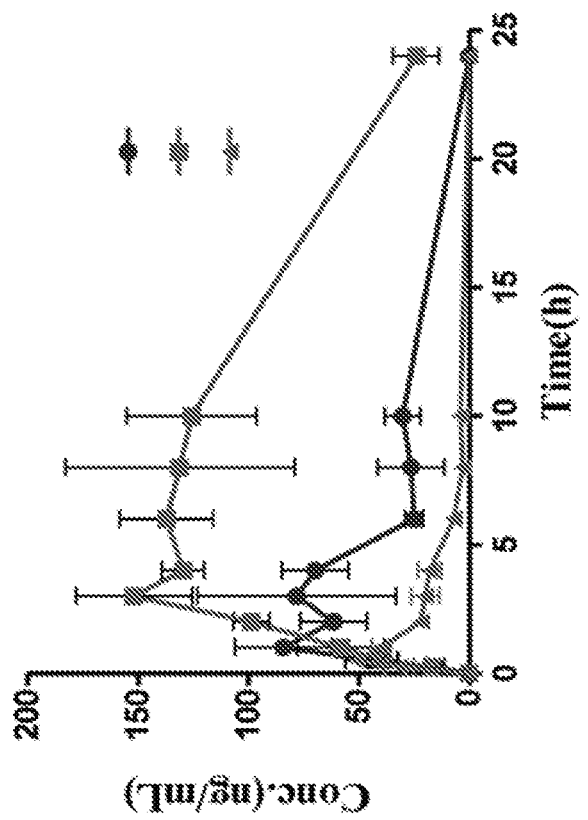
FIG. 5 shows Oral PK study of SGI-105 in comparison with AZD9291 and SGI-101. Compounds were administrated to mouse as a single dose of 10 mg/kg.

Oral PK study of SGI-105 in comparison with AZD9291 and SGI-101 is shown on FIG. 5. Compounds were administrated to mouse as a single dose of 10 mg/kg. Essays conducted as outlined in Examples 1 and 2.

Compounds reference in the present disclosure is listed below in Table 1.

TABLE 1

Compound List

| Cpd ID | Structure |
|---|---|
| SGI-001 | 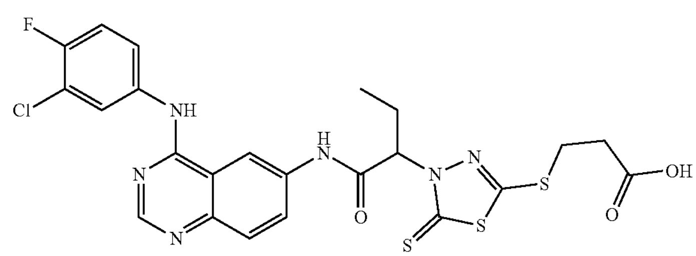 [SMILES: CCC(C(=O)Nc1ccc2ncnc(Nc3ccc(F)c(Cl)c3)c2c1)n1nc(SCCC(=O)O)sc1=S] |
| SGI-002 | 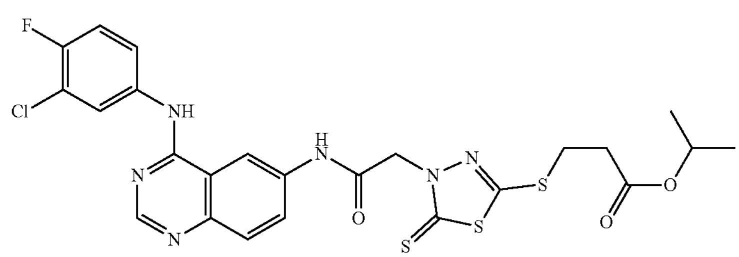 [SMILES: CC(C)OC(=O)CCSc1nn(CC(=O)Nc2ccc3ncnc(Nc4ccc(F)c(Cl)c4)c3c2)c(=S)s1] |

TABLE 1-continued
Compound List
| Cpd ID | Structure |
|---|---|
| SGI-003 | 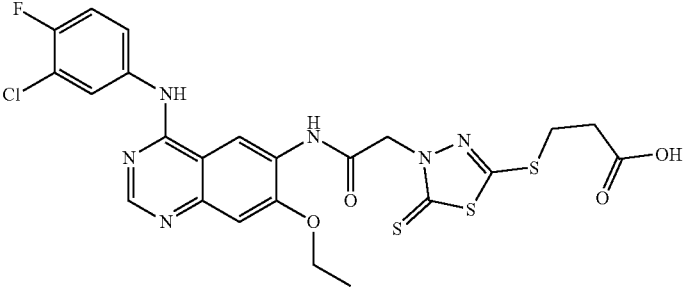 [SMILES: CCOc1cc2ncnc(Nc3ccc(F)c(Cl)c3)c2cc1NC(=O)Cn1nc(SCCC(=O)O)sc1=S] |
| SGI-004 | 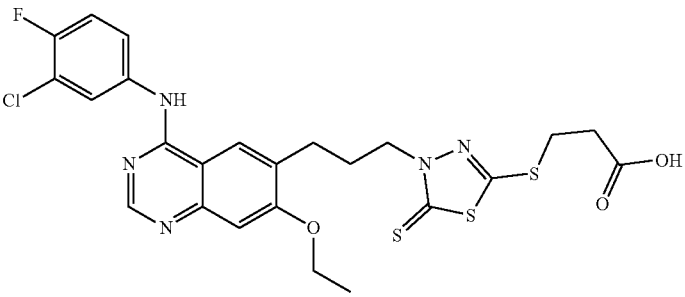 [SMILES: CCOc1cc2ncnc(Nc3ccc(F)c(Cl)c3)c2cc1CCCn1nc(SCCC(=O)O)sc1=S] |
| SGI-005 | 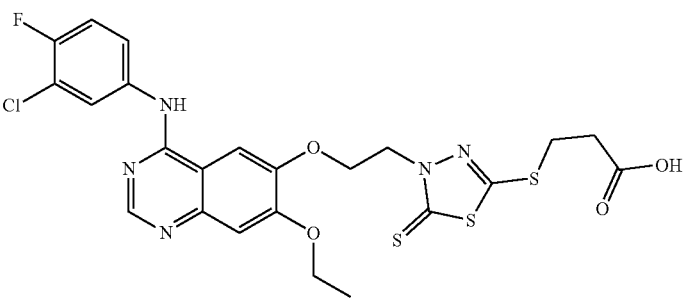 [SMILES: CCOc1cc2ncnc(Nc3ccc(F)c(Cl)c3)c2cc1OCCn1nc(SCCC(=O)O)sc1=S] |
| SGI-006 | 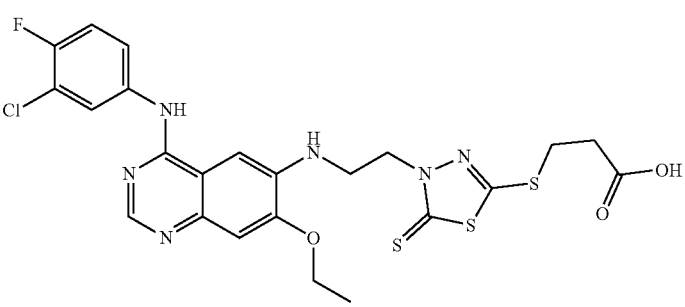 [SMILES: CCOc1cc2ncnc(Nc3ccc(F)c(Cl)c3)c2cc1NCCn1nc(SCCC(=O)O)sc1=S] |
| SGI-007 | 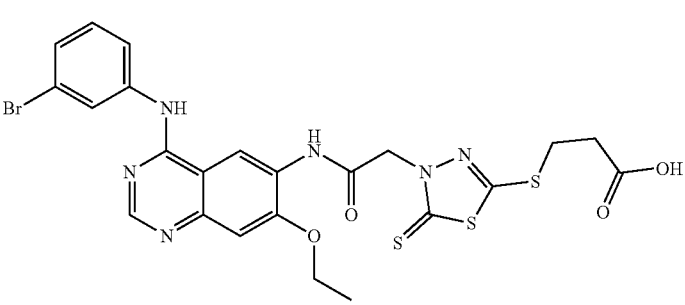 [SMILES: CCOc1cc2ncnc(Nc3cccc(Br)c3)c2cc1NC(=O)Cn1nc(SCCC(=O)O)sc1=S] |

TABLE 1-continued

Compound List

| Cpd ID | Structure |
|---|---|
| SGI-008 | 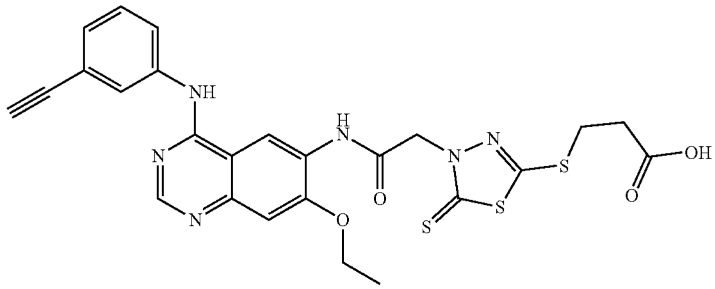 [SMILES: C#Cc1cccc(Nc2ncnc3cc(OCC)c(NC(=O)Cn4nc(SCCC(=O)O)sc4=S)cc23)c1] |
| SGI-009 | 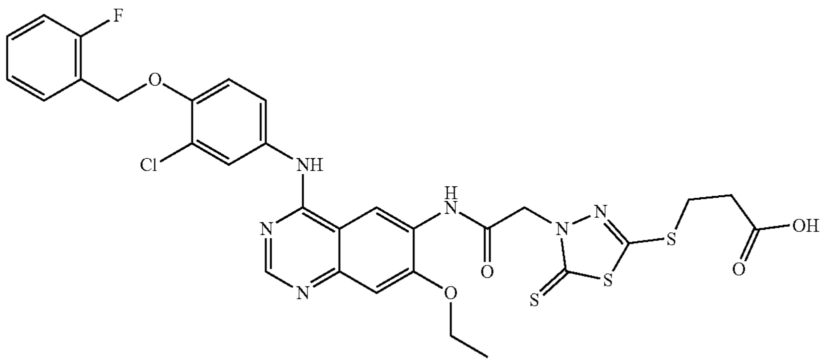 [SMILES: CCOc1cc2ncnc(Nc3ccc(OCc4ccccc4F)c(Cl)c3)c2cc1NC(=O)Cn1nc(SCCC(=O)O)sc1=S] |
| SGI-010 | 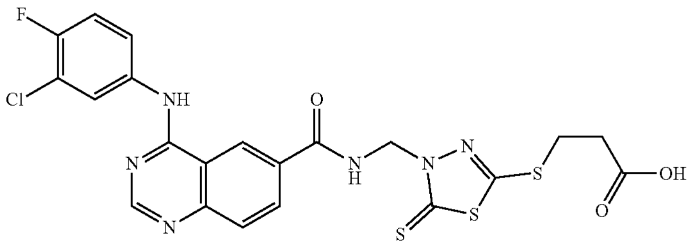 [SMILES: O=C(O)CCSc1nn(CNC(=O)c2ccc3ncnc(Nc4ccc(F)c(Cl)c4)c3c2)c(=S)s1] |
| SGI-011 | 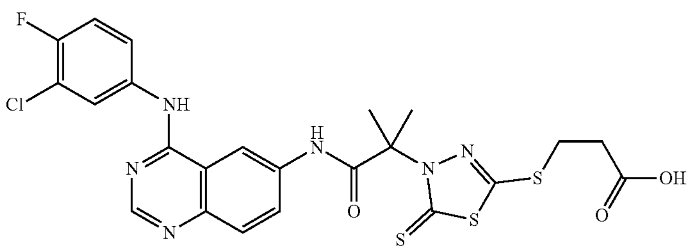 [SMILES: CC(C)(C(=O)Nc1ccc2ncnc(Nc3ccc(F)c(Cl)c3)c2c1)n1nc(SCCC(=O)O)sc1=S] |
| SGI-012 | 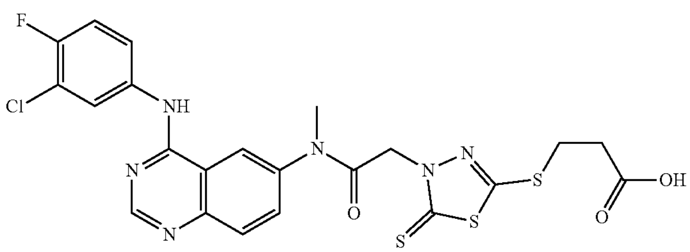 [SMILES: CN(C(=O)Cn1nc(SCCC(=O)O)sc1=S)c1ccc2ncnc(Nc3ccc(F)c(Cl)c3)c2c1] |

TABLE 1-continued

| Cpd ID | Structure |
|---|---|
| SGI-013 | 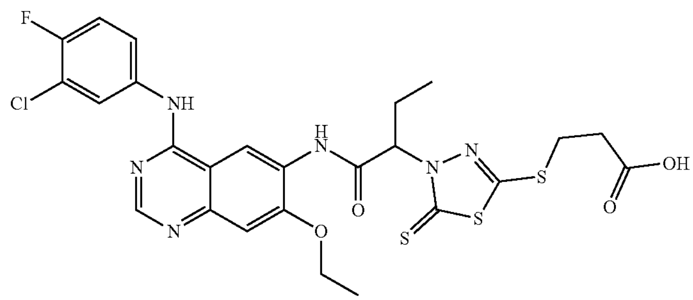 [SMILES: CCOc1cc2ncnc(Nc3ccc(F)c(Cl)c3)c2cc1NC(=O)C(CC)n1nc(SCCC(=O)O)sc1=S] |
| SGI-014 | 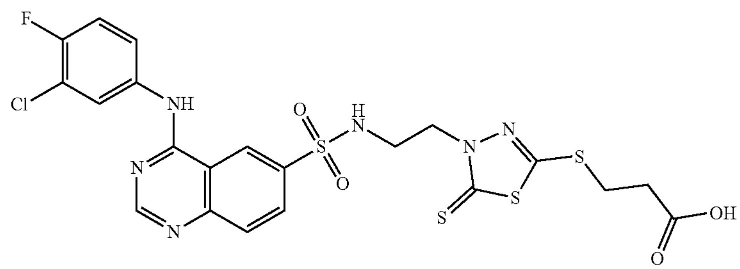 [SMILES: O=C(O)CCSc1nn(CCNS(=O)(=O)c2ccc3ncnc(Nc4ccc(F)c(Cl)c4)c3c2)c(=S)s1] |
| SGI-015 | 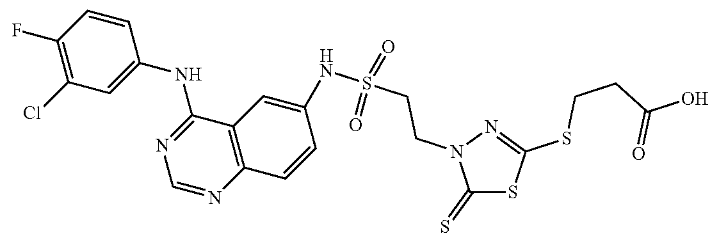 [SMILES: O=C(O)CCSc1nn(CCS(=O)(=O)Nc2ccc3ncnc(Nc4ccc(F)c(Cl)c4)c3c2)c(=S)s1] |
| SGI-016 | 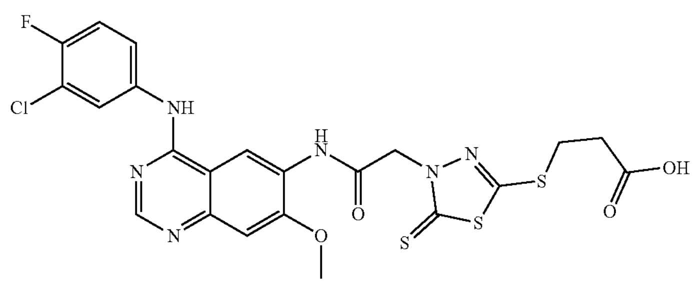 [SMILES: COc1cc2ncnc(Nc3ccc(F)c(Cl)c3)c2cc1NC(=O)Cn1nc(SCCC(=O)O)sc1=S] |
| SGI-017 | 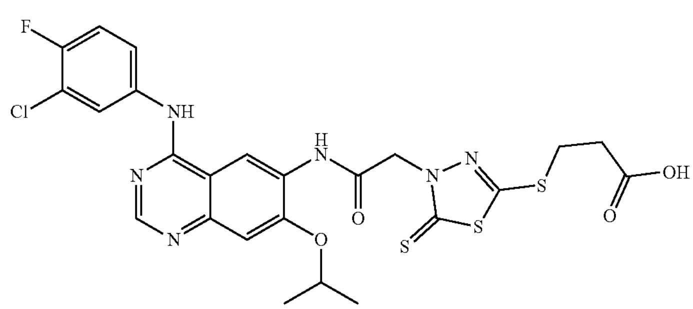 [SMILES: CC(C)Oc1cc2ncnc(Nc3ccc(F)c(Cl)c3)c2cc1NC(=O)Cn1nc(SCCC(=O)O)sc1=S] |

TABLE 1-continued

Compound List

| Cpd ID | Structure |
|---|---|
| SGI-018 | (structure) |
| SGI-019 | (structure) |
| SGI-020 | (structure) |
| SGI-021 | (structure) |
| SGI-022 | (structure) |

TABLE 1-continued

Compound List

| Cpd ID | Structure |
|---|---|
| SGI-023 | 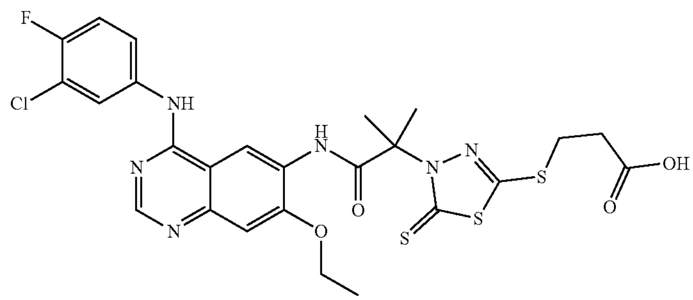 [SMILES: CCOc1cc2ncnc(Nc3ccc(F)c(Cl)c3)c2cc1NC(=O)C(C)(C)n1nc(SCCC(=O)O)sc1=S] |
| SGI-024 | 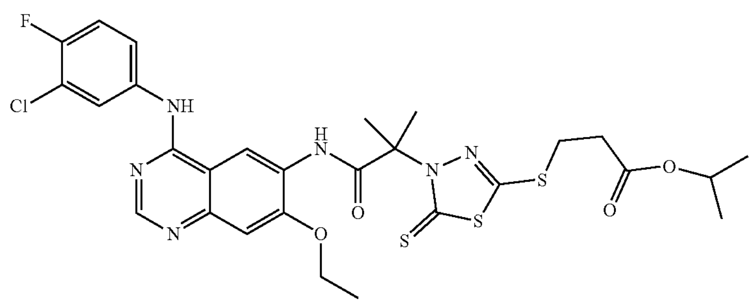 [SMILES: CCOc1cc2ncnc(Nc3ccc(F)c(Cl)c3)c2cc1NC(=O)C(C)(C)n1nc(SCCC(=O)OC(C)C)sc1=S] |
| SGI-003-Na salt | 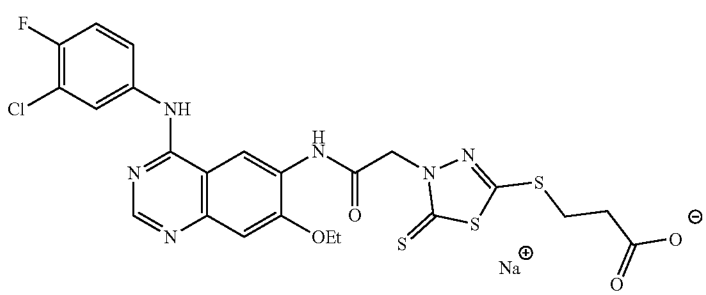 [SMILES: CCOc1cc2ncnc(Nc3ccc(F)c(Cl)c3)c2cc1NC(=O)Cn1nc(SCCC(=O)[O-])sc1=S ; [Na+]] |
| SGI-025 | 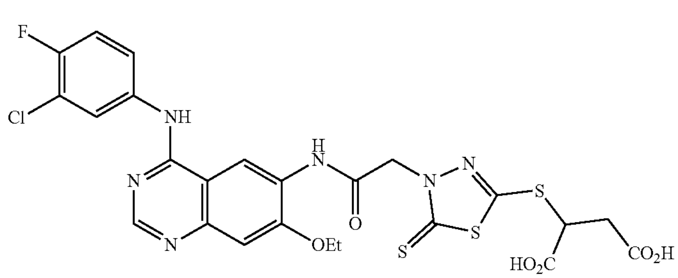 [SMILES: CCOc1cc2ncnc(Nc3ccc(F)c(Cl)c3)c2cc1NC(=O)Cn1nc(SC(CC(=O)O)C(=O)O)sc1=S] |

TABLE 1-continued
Compound List
| Cpd ID | Structure |
|---|---|
| SGI-026 | 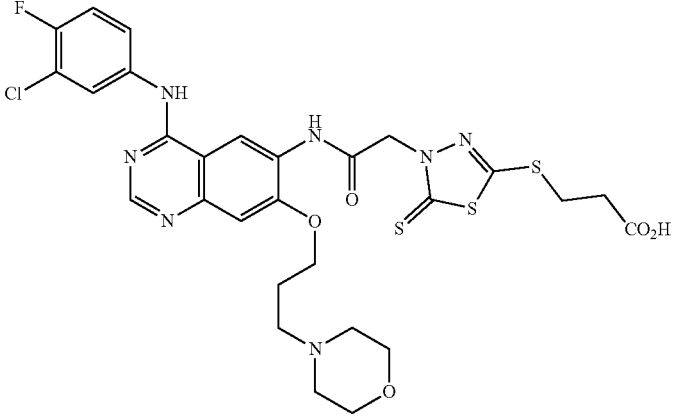 [SMILES: O=C(O)CCSc1nn(CC(=O)Nc2cc3c(Nc4ccc(F)c(Cl)c4)ncnc3cc2OCCCN2CCOCC2)c(=S)s1] |
| SGI-027 | 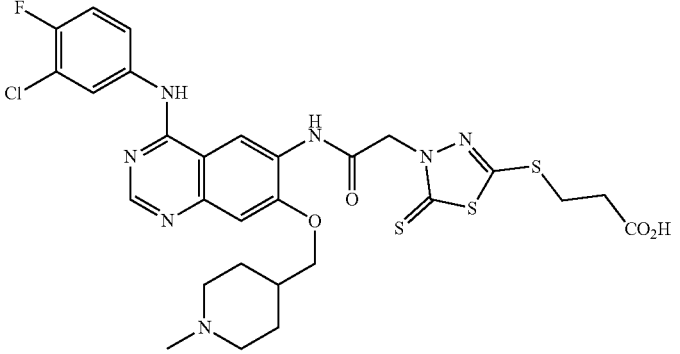 [SMILES: CN1CCC(COc2cc3ncnc(Nc4ccc(F)c(Cl)c4)c3cc2NC(=O)Cn2nc(SCCC(=O)O)sc2=S)CC1] |
| SGI-028 | 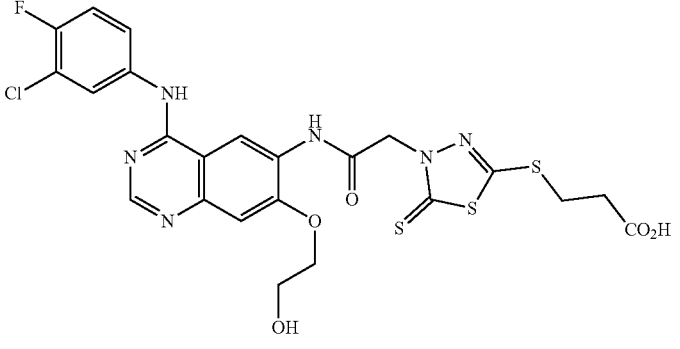 [SMILES: O=C(O)CCSc1nn(CC(=O)Nc2cc3c(Nc4ccc(F)c(Cl)c4)ncnc3cc2OCCO)c(=S)s1] |
| SGI-029 | 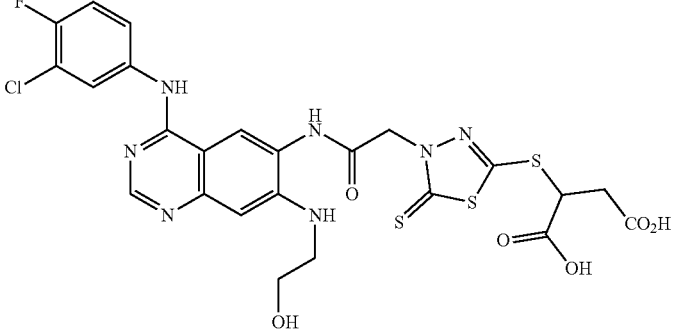 |

TABLE 1-continued

Compound List

| Cpd ID | Structure |
|---|---|
| SGI-030 | 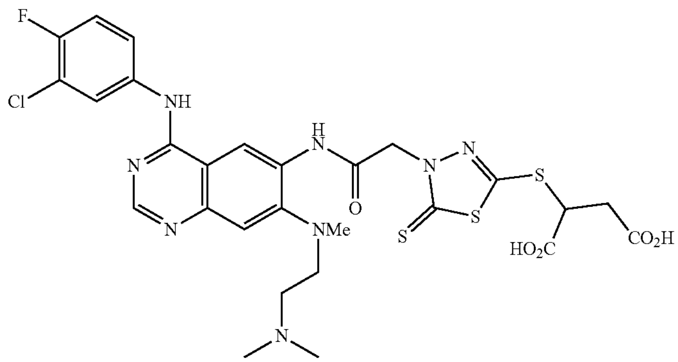 [SMILES: CN(C)CCN(C)c1cc2ncnc(Nc3ccc(F)c(Cl)c3)c2cc1NC(=O)Cn1nc(SC(CC(=O)O)C(=O)O)sc1=S] |
| SGI-031 or Na salt | 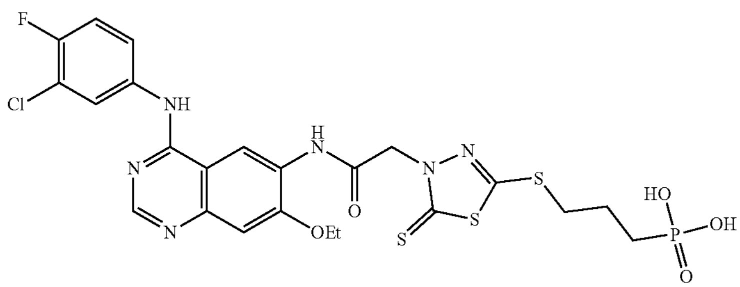 [SMILES: CCOc1cc2ncnc(Nc3ccc(F)c(Cl)c3)c2cc1NC(=O)Cn1nc(SCCCP(=O)(O)O)sc1=S] |
| SGI-032 | 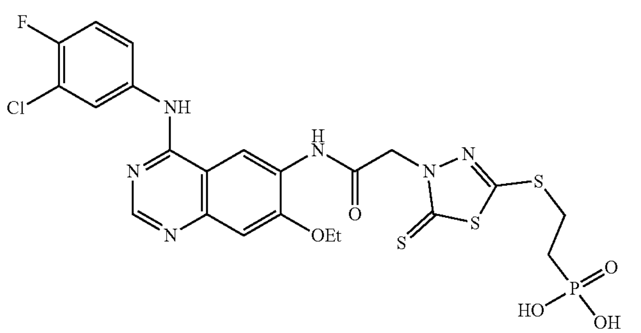 [SMILES: CCOc1cc2ncnc(Nc3ccc(F)c(Cl)c3)c2cc1NC(=O)Cn1nc(SCCP(=O)(O)O)sc1=S] |
| SGI-033 | 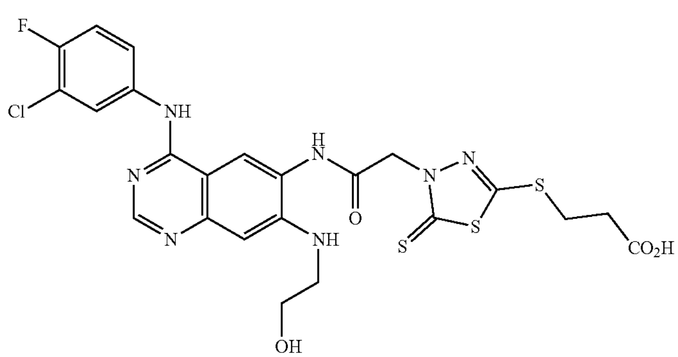 [SMILES: O=C(O)CCSc1nn(CC(=O)Nc2cc3c(Nc4ccc(F)c(Cl)c4)ncnc3cc2NCCO)c(=S)s1] |

TABLE 1-continued
Compound List
| Cpd ID | Structure |
|---|---|
| SGI-034 | 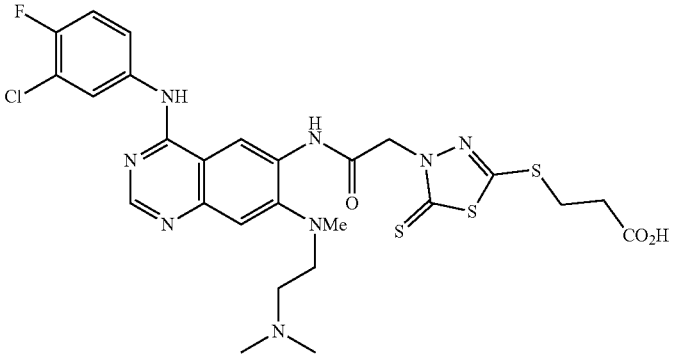 [SMILES: CN(C)CCN(C)c1cc2ncnc(Nc3ccc(F)c(Cl)c3)c2cc1NC(=O)Cn1nc(SCCC(=O)O)sc1=S] |
| SGI-035 | 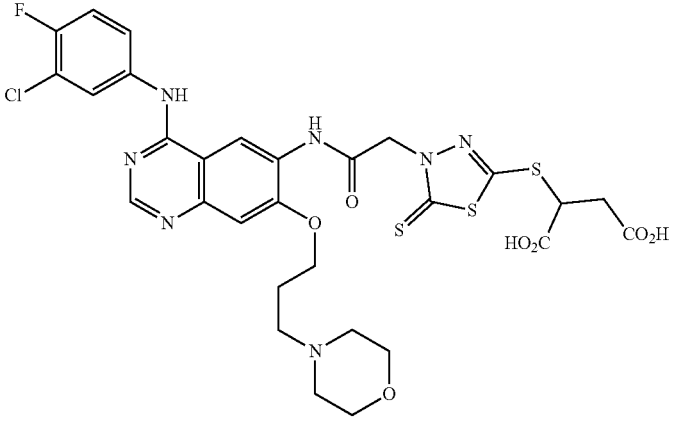 [SMILES: O=C(O)CC(Sc1nn(CC(=O)Nc2cc3c(Nc4ccc(F)c(Cl)c4)ncnc3cc2OCCCN2CCOCC2)c(=S)s1)C(=O)O] |
| SGI-036 | 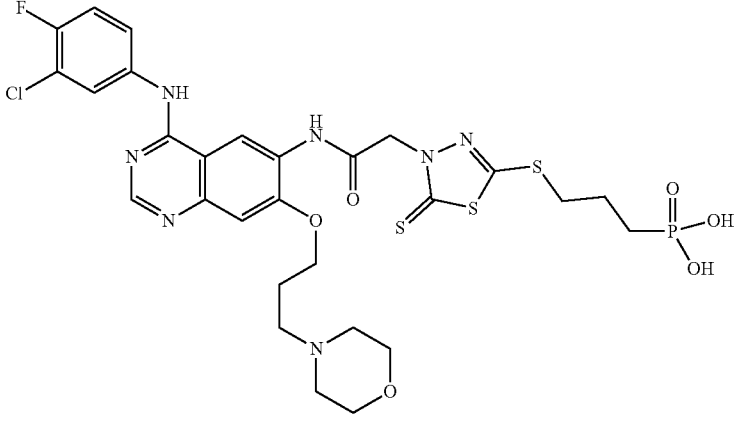 [SMILES: O=C(Cn1nc(SCCCP(=O)(O)O)sc1=S)Nc1cc2c(Nc3ccc(F)c(Cl)c3)ncnc2cc1OCCCN1CCOCC1] |
| SGI-037 | 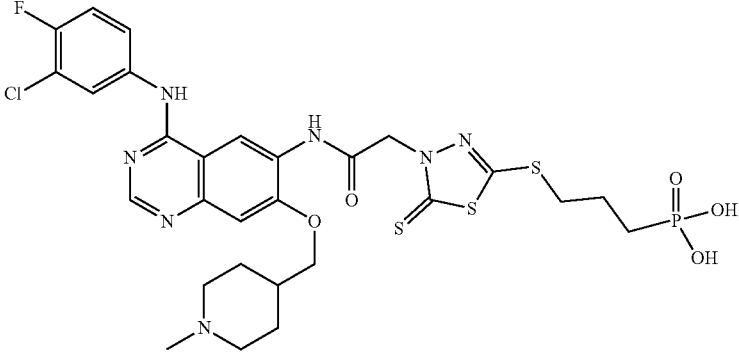 |

TABLE 1-continued
Compound List
| Cpd ID | Structure |
|---|---|
| SGI-038 | 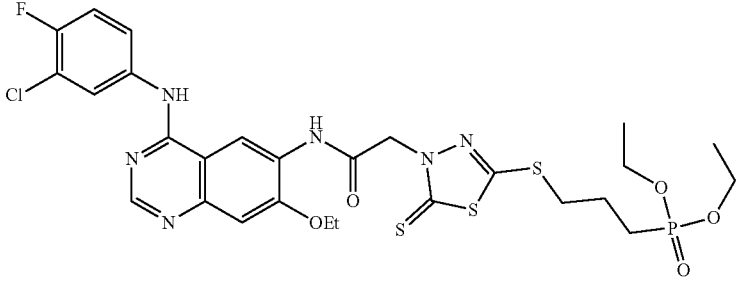 [SMILES: CCOc1cc2ncnc(Nc3ccc(F)c(Cl)c3)c2cc1NC(=O)Cn1nc(SCCCP(=O)(OCC)OCC)sc1=S] |
| SGI-039 | 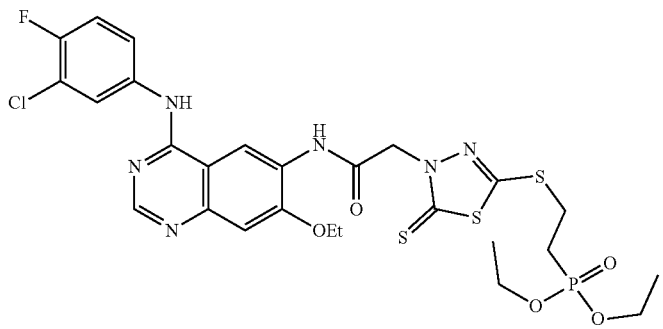 [SMILES: CCOc1cc2ncnc(Nc3ccc(F)c(Cl)c3)c2cc1NC(=O)Cn1nc(SCCP(=O)(OCC)OCC)sc1=S] |
| SGI-040 | 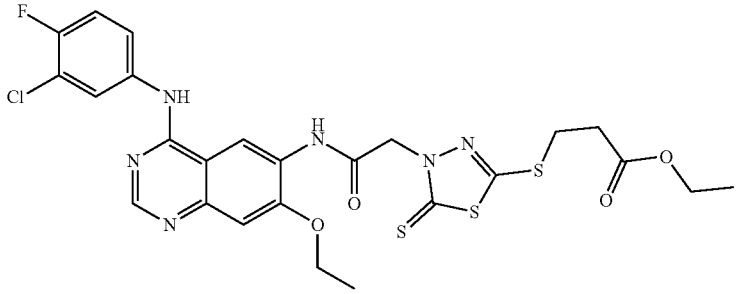 [SMILES: CCOC(=O)CCSc1nn(CC(=O)Nc2cc3c(Nc4ccc(F)c(Cl)c4)ncnc3cc2OCC)c(=S)s1] |
| SGI-041 | 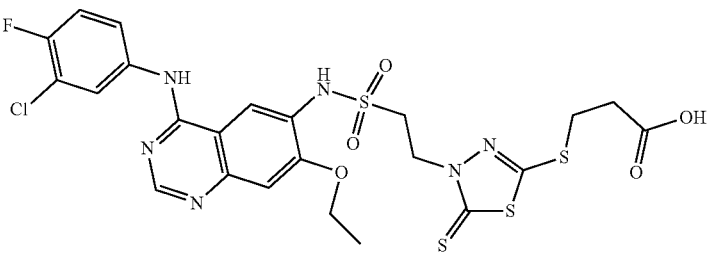 [SMILES: CCOc1cc2ncnc(Nc3ccc(F)c(Cl)c3)c2cc1NS(=O)(=O)CCn1nc(SCCC(=O)O)sc1=S] |
| SGI-042 | 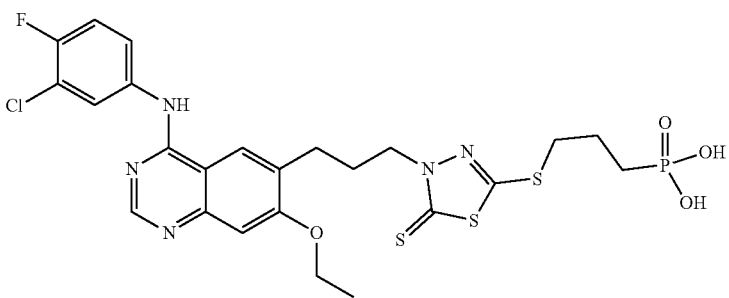 [SMILES: CCOc1cc2ncnc(Nc3ccc(F)c(Cl)c3)c2cc1CCCn1nc(SCCCP(=O)(O)O)sc1=S] |

TABLE 1-continued

Compound List

| Cpd ID | Structure |
|---|---|
| SGI-043 | *(structure)* |
| SGI-044 | *(structure)* |
| SGI-045 | *(structure)* |
| SGI-046 | *(structure)* |
| SGI-047 | *(structure)* |

TABLE 1-continued
Compound List
| Cpd ID | Structure |
|---|---|
| SGI-048 | 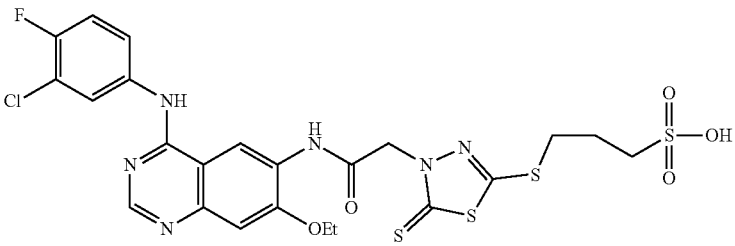 [SMILES: CCOc1cc2ncnc(Nc3ccc(F)c(Cl)c3)c2cc1NC(=O)Cn1nc(SCCCS(=O)(=O)O)sc1=S] |
| SGI-049 | 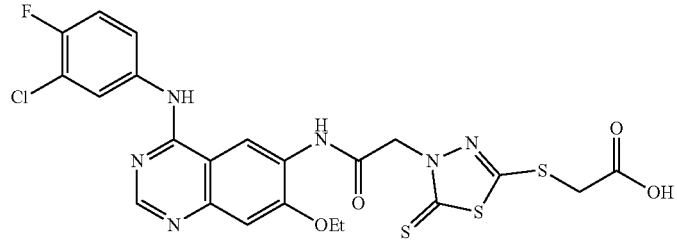 [SMILES: CCOc1cc2ncnc(Nc3ccc(F)c(Cl)c3)c2cc1NC(=O)Cn1nc(SCC(=O)O)sc1=S] |
| SGI-050 | 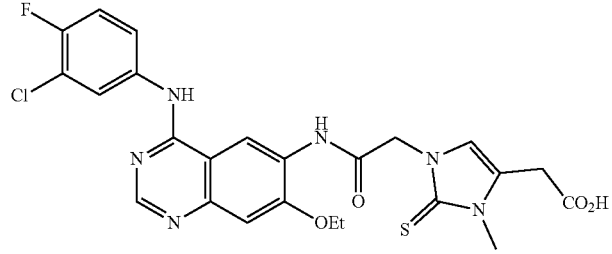 [SMILES: CCOc1cc2ncnc(Nc3ccc(F)c(Cl)c3)c2cc1NC(=O)Cn1cc(CC(=O)O)n(C)c1=S] |
| SGI-051 | 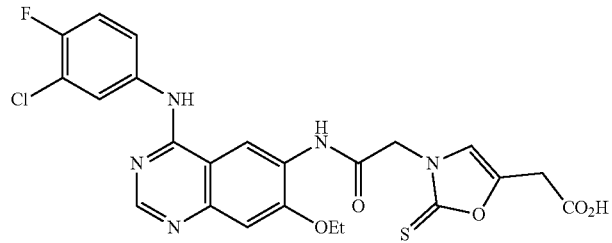 [SMILES: CCOc1cc2ncnc(Nc3ccc(F)c(Cl)c3)c2cc1NC(=O)Cn1cc(CC(=O)O)oc1=S] |
| SGI-052 | 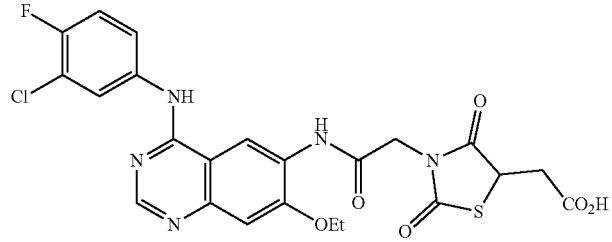 [SMILES: CCOc1cc2ncnc(Nc3ccc(F)c(Cl)c3)c2cc1NC(=O)CN1C(=O)SC(CC(=O)O)C1=O] |
| SGI-053 | 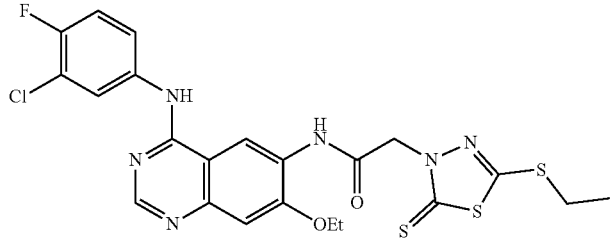 [SMILES: CCOc1cc2ncnc(Nc3ccc(F)c(Cl)c3)c2cc1NC(=O)Cn1nc(SCC)sc1=S] |

TABLE 1-continued

Compound List

| Cpd ID | Structure |
|---|---|
| SGI-054 | 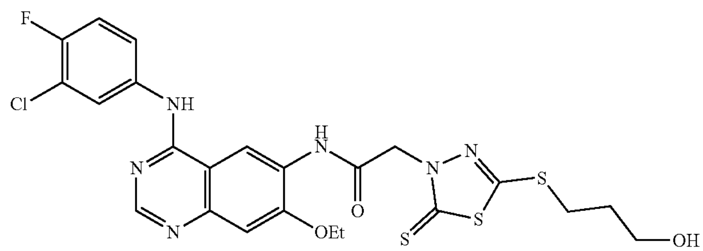 [SMILES: CCOc1cc2ncnc(Nc3ccc(F)c(Cl)c3)c2cc1NC(=O)Cn1nc(SCCCO)sc1=S] |
| SGI-055 | 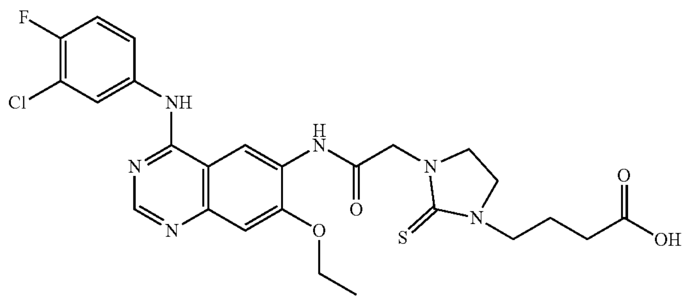 [SMILES: CCOc1cc2ncnc(Nc3ccc(F)c(Cl)c3)c2cc1NC(=O)CN1CCN(CCCC(=O)O)C1=S] |
| SGI-056 | 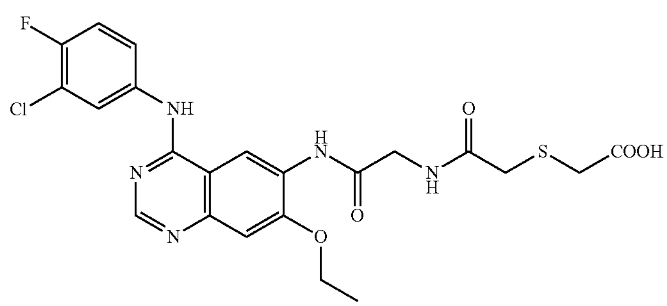 [SMILES: CCOc1cc2ncnc(Nc3ccc(F)c(Cl)c3)c2cc1NC(=O)CNC(=O)CSCC(=O)O] |
| SGI-057 | 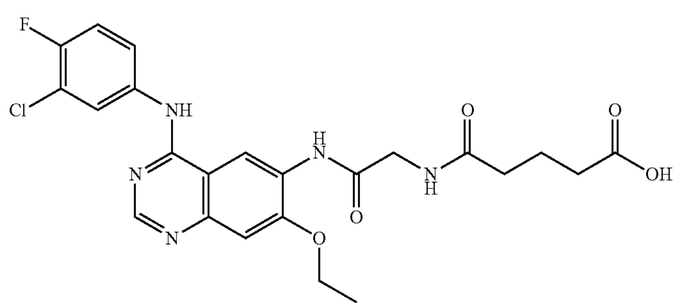 [SMILES: CCOc1cc2ncnc(Nc3ccc(F)c(Cl)c3)c2cc1NC(=O)CNC(=O)CCCC(=O)O] |
| SGI-058 | 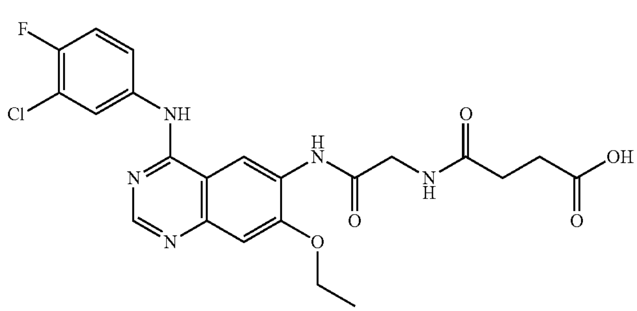 [SMILES: CCOc1cc2ncnc(Nc3ccc(F)c(Cl)c3)c2cc1NC(=O)CNC(=O)CCC(=O)O] |

TABLE 1-continued
Compound List
| Cpd ID | Structure |
|---|---|
| SGI-059 | 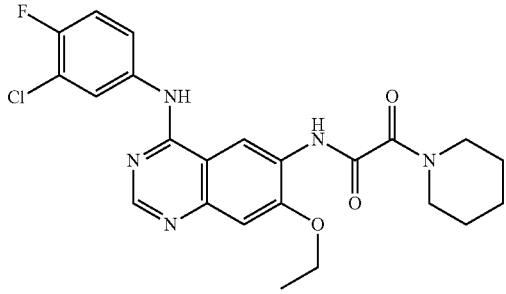 [SMILES: CCOc1cc2ncnc(Nc3ccc(F)c(Cl)c3)c2cc1NC(=O)C(=O)N1CCCCC1] |
| SGI-060 | 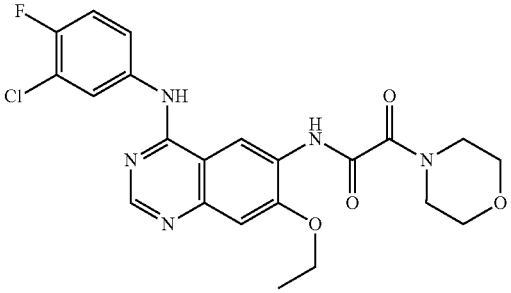 [SMILES: CCOc1cc2ncnc(Nc3ccc(F)c(Cl)c3)c2cc1NC(=O)C(=O)N1CCOCC1] |
| SGI-061 | 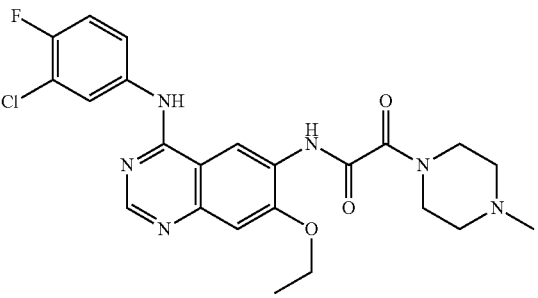 [SMILES: CCOc1cc2ncnc(Nc3ccc(F)c(Cl)c3)c2cc1NC(=O)C(=O)N1CCN(C)CC1] |
| SGI-062 | 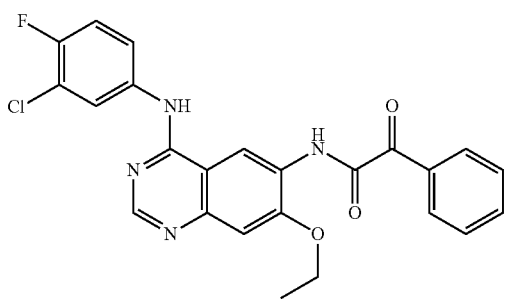 [SMILES: CCOc1cc2ncnc(Nc3ccc(F)c(Cl)c3)c2cc1NC(=O)C(=O)c1ccccc1] |
| SGI-063 | 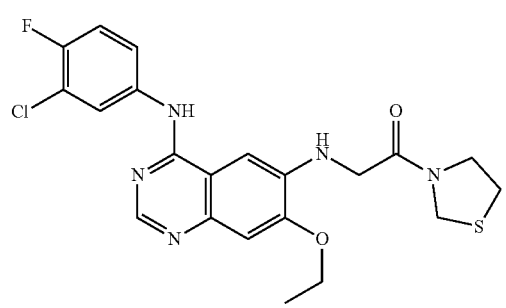 [SMILES: CCOc1cc2ncnc(Nc3ccc(F)c(Cl)c3)c2cc1NCC(=O)N1CCSC1] |

TABLE 1-continued

Compound List

| Cpd ID | Structure |
|---|---|
| SGI-064 | 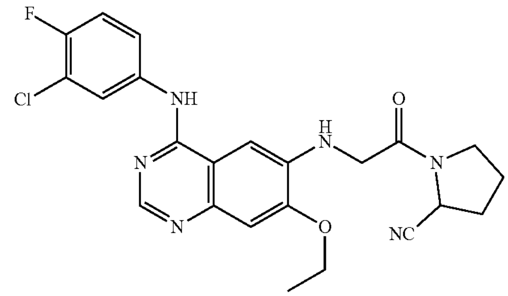 [SMILES: CCOc1cc2ncnc(Nc3ccc(F)c(Cl)c3)c2cc1NCC(=O)N1CCCC1C#N] |
| SGI-065 | 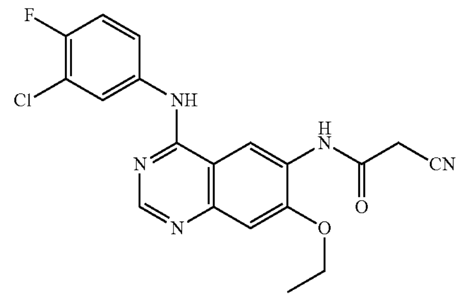 [SMILES: CCOc1cc2ncnc(Nc3ccc(F)c(Cl)c3)c2cc1NC(=O)CC#N] |
| SGI-066 | 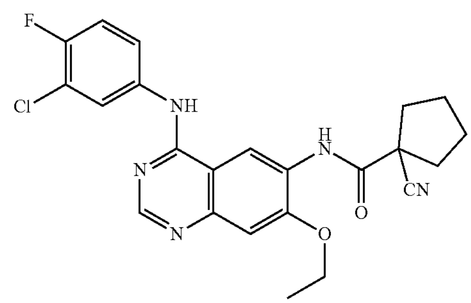 [SMILES: CCOc1cc2ncnc(Nc3ccc(F)c(Cl)c3)c2cc1NC(=O)C1(C#N)CCCC1] |
| SGI-067 | 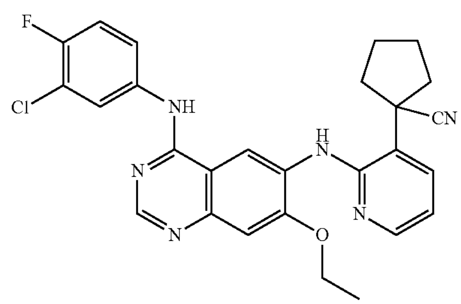 [SMILES: CCOc1cc2ncnc(Nc3ccc(F)c(Cl)c3)c2cc1Nc1ncccc1C1(C#N)CCCC1] |
| SGI-068 | 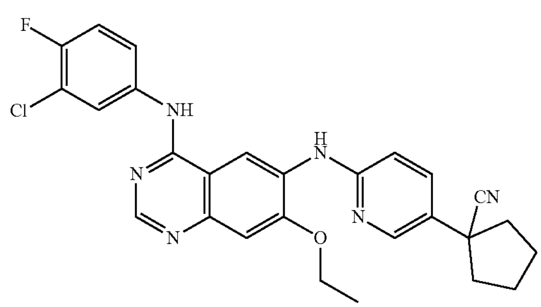 [SMILES: CCOc1cc2ncnc(Nc3ccc(F)c(Cl)c3)c2cc1Nc1ccc(C2(C#N)CCCC2)cn1] |

TABLE 1-continued
Compound List
| Cpd ID | Structure |
|---|---|
| SGI-069 | 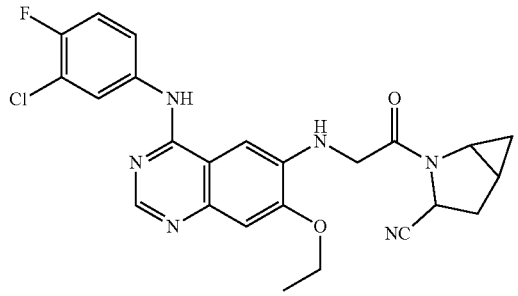 [SMILES: CCOc1cc2ncnc(Nc3ccc(F)c(Cl)c3)c2cc1NCC(=O)N1C(C#N)CC2CC21] |
| SGI-060 | 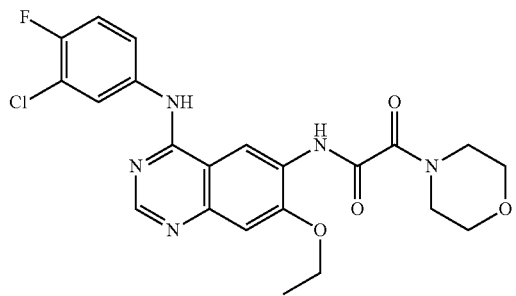 [SMILES: CCOc1cc2ncnc(Nc3ccc(F)c(Cl)c3)c2cc1NC(=O)C(=O)N1CCOCC1] |
| SGI-061 | 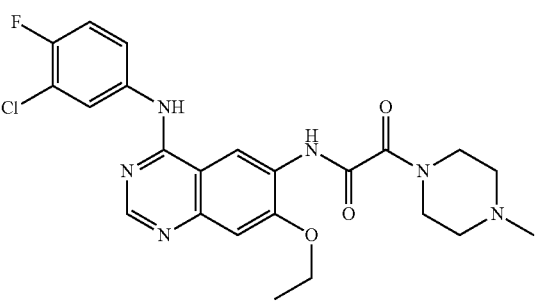 [SMILES: CCOc1cc2ncnc(Nc3ccc(F)c(Cl)c3)c2cc1NC(=O)C(=O)N1CCN(C)CC1] |
| SGI-062 | 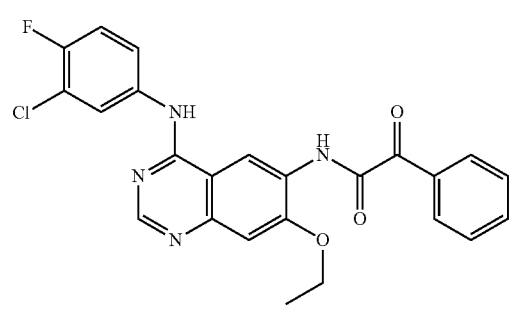 [SMILES: CCOc1cc2ncnc(Nc3ccc(F)c(Cl)c3)c2cc1NC(=O)C(=O)c1ccccc1] |
| SGI-063 | 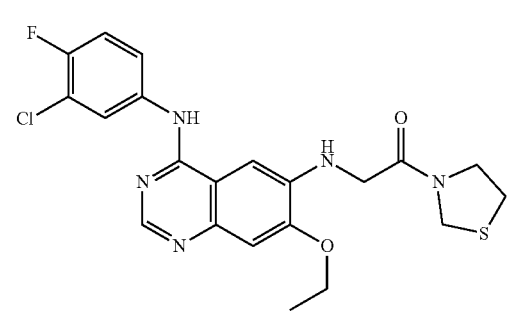 [SMILES: CCOc1cc2ncnc(Nc3ccc(F)c(Cl)c3)c2cc1NCC(=O)N1CCSC1] |

TABLE 1-continued
Compound List
| Cpd ID | Structure |
|---|---|
| SGI-064 | 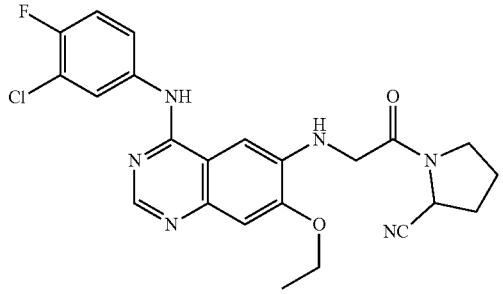 [SMILES: CCOc1cc2ncnc(Nc3ccc(F)c(Cl)c3)c2cc1NCC(=O)N1CCCC1C#N] |
| SGI-065 | 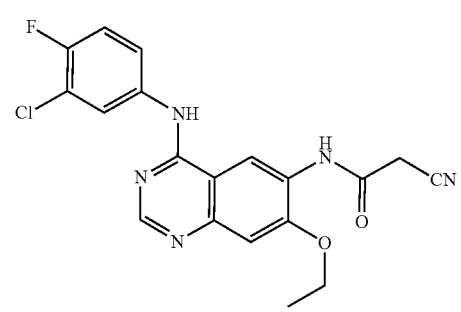 [SMILES: CCOc1cc2ncnc(Nc3ccc(F)c(Cl)c3)c2cc1NC(=O)CC#N] |
| SGI-066 | 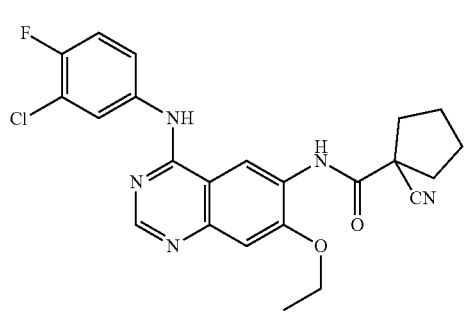 [SMILES: CCOc1cc2ncnc(Nc3ccc(F)c(Cl)c3)c2cc1NC(=O)C1(C#N)CCCC1] |
| SGI-067 | 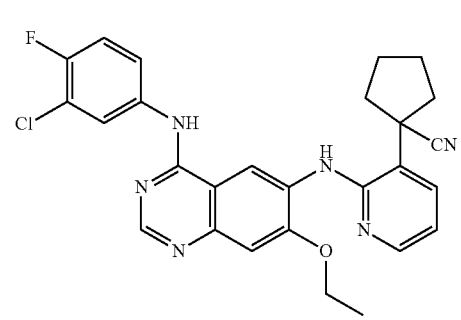 [SMILES: CCOc1cc2ncnc(Nc3ccc(F)c(Cl)c3)c2cc1Nc1ncccc1C1(C#N)CCCC1] |
| SGI-068 | 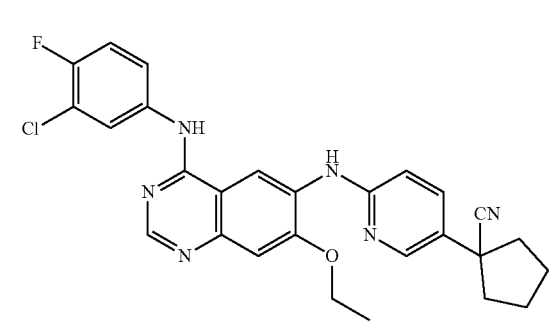 [SMILES: CCOc1cc2ncnc(Nc3ccc(F)c(Cl)c3)c2cc1Nc1ccc(C2(C#N)CCCC2)cn1] |

TABLE 1-continued
Compound List
| Cpd ID | Structure |
|---|---|
| SGI-069 | 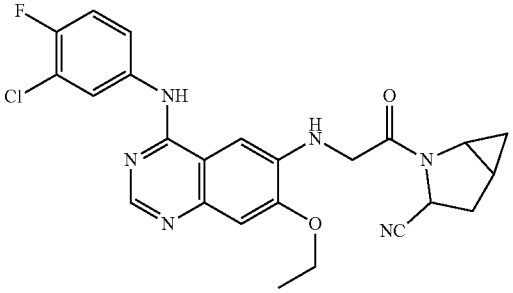 [SMILES: CCOc1cc2ncnc(Nc3ccc(F)c(Cl)c3)c2cc1NCC(=O)N1C(C#N)CC2CC21] |
| SGI-070 | 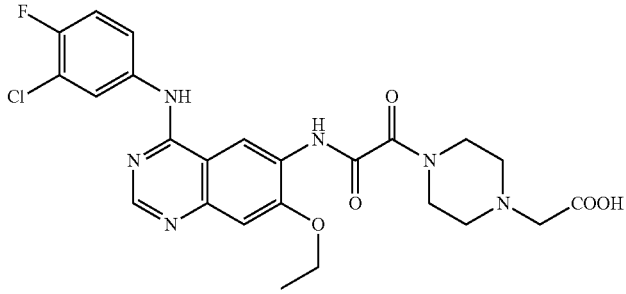 [SMILES: CCOc1cc2ncnc(Nc3ccc(F)c(Cl)c3)c2cc1NC(=O)C(=O)N1CCN(CC(=O)O)CC1] |
| SGI-071 | 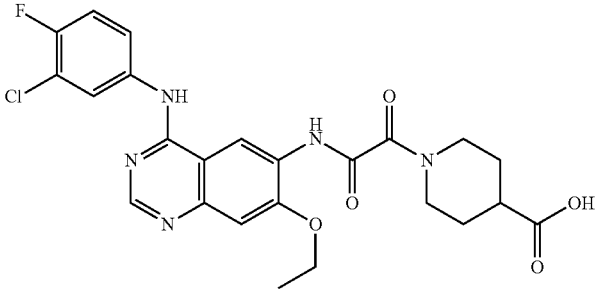 [SMILES: CCOc1cc2ncnc(Nc3ccc(F)c(Cl)c3)c2cc1NC(=O)C(=O)N1CCC(C(=O)O)CC1] |
| SGI-072 | 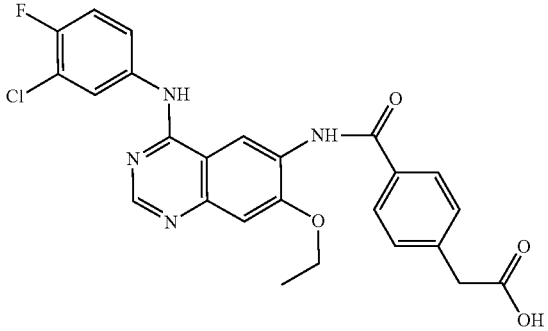 [SMILES: CCOc1cc2ncnc(Nc3ccc(F)c(Cl)c3)c2cc1NC(=O)c1ccc(CC(=O)O)cc1] |
| SGI-073 | 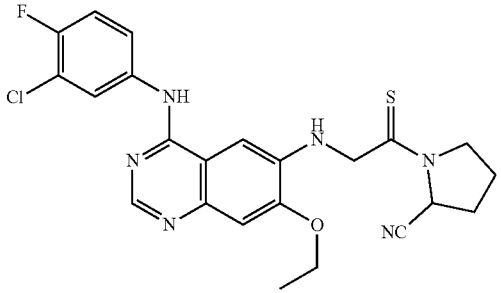 |

TABLE 1-continued
Compound List
| Cpd ID | Structure |
|---|---|
| SGI-074 | 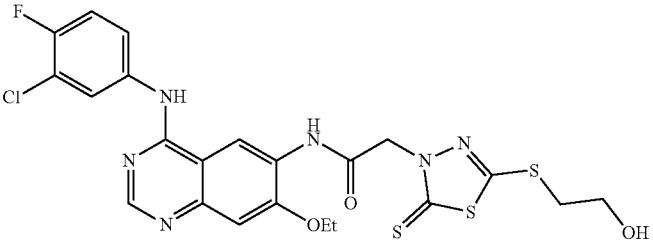 [SMILES: CCOc1cc2ncnc(Nc3ccc(F)c(Cl)c3)c2cc1NC(=O)Cn1nc(SCCO)sc1=S] |
| SGI-075 | 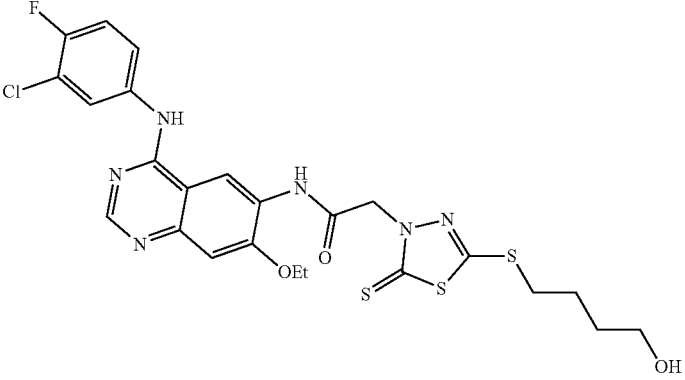 [SMILES: CCOc1cc2ncnc(Nc3ccc(F)c(Cl)c3)c2cc1NC(=O)Cn1nc(SCCCCO)sc1=S] |
| SGI-076 | 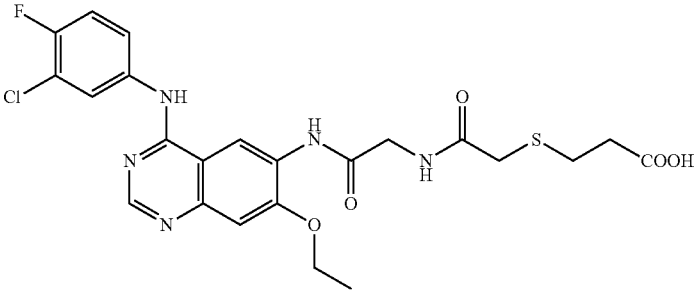 [SMILES: CCOc1cc2ncnc(Nc3ccc(F)c(Cl)c3)c2cc1NC(=O)CNC(=O)CSCCC(=O)O] |
| SGI-077 | 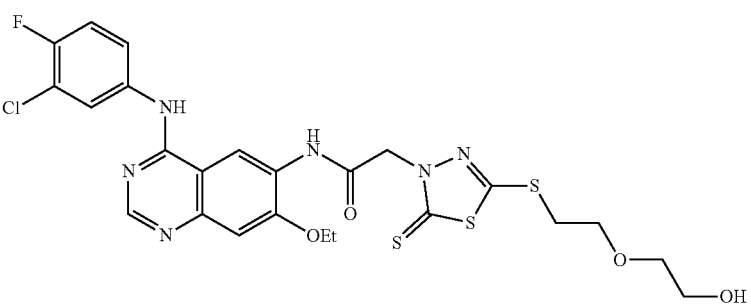 [SMILES: CCOc1cc2ncnc(Nc3ccc(F)c(Cl)c3)c2cc1NC(=O)Cn1nc(SCCOCCO)sc1=S] |
| SGI-078 | 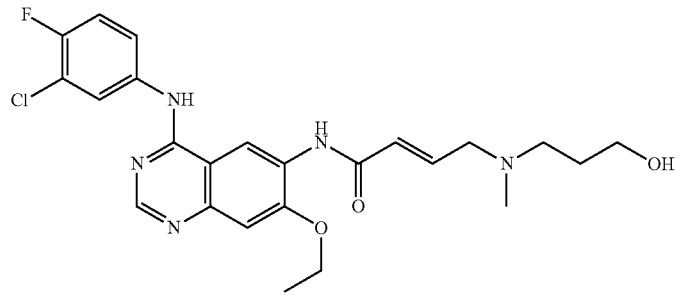 [SMILES: CCOc1cc2ncnc(Nc3ccc(F)c(Cl)c3)c2cc1NC(=O)/C=C/CN(C)CCCO] |

TABLE 1-continued
Compound List
| Cpd ID | Structure |
|---|---|
| SGI-079 | 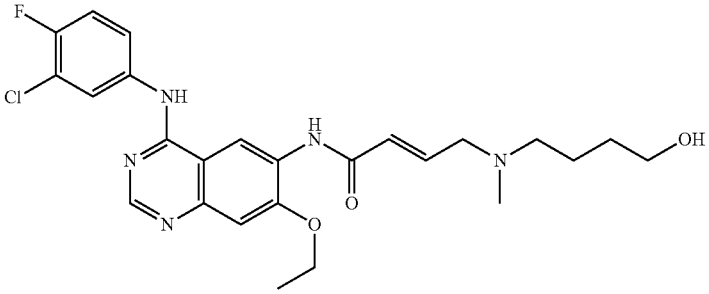 [SMILES: CCOc1cc2ncnc(Nc3ccc(F)c(Cl)c3)c2cc1NC(=O)/C=C/CN(C)CCCCO] |
| SGI-080 | 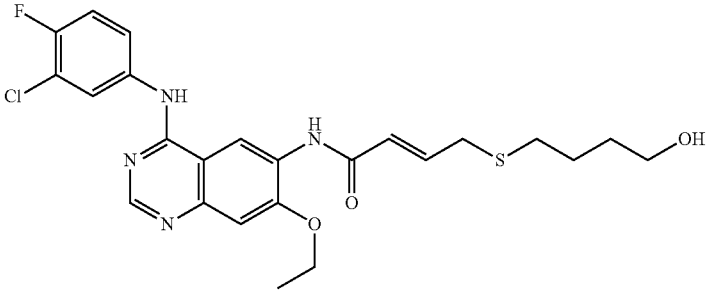 [SMILES: CCOc1cc2ncnc(Nc3ccc(F)c(Cl)c3)c2cc1NC(=O)/C=C/CSCCCCO] |
| SGI-081 | 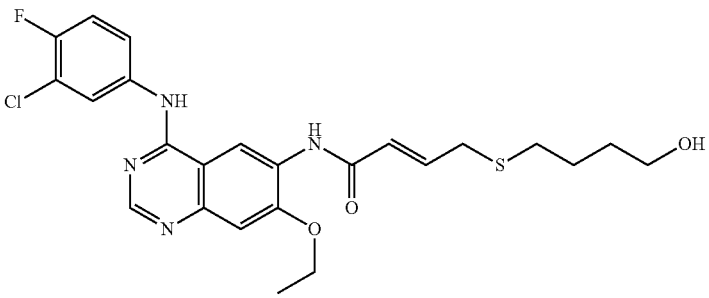 [SMILES: CCOc1cc2ncnc(Nc3ccc(F)c(Cl)c3)c2cc1NC(=O)/C=C/CSCCCCO] |
| SGI-082 | 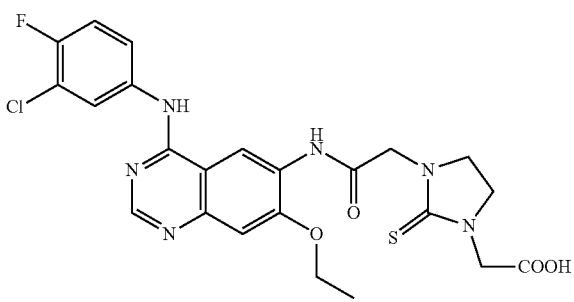 [SMILES: CCOc1cc2ncnc(Nc3ccc(F)c(Cl)c3)c2cc1NC(=O)CN1CCN(CC(=O)O)C1=S] |
| SGI-083 | 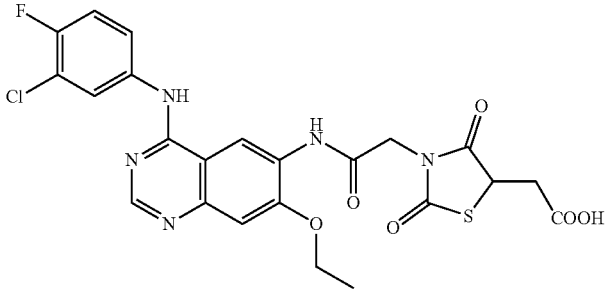 [SMILES: CCOc1cc2ncnc(Nc3ccc(F)c(Cl)c3)c2cc1NC(=O)CN1C(=O)SC(CC(=O)O)C1=O] |

TABLE 1-continued

Compound List

| Cpd ID | Structure |
|---|---|
| SGI-084 | 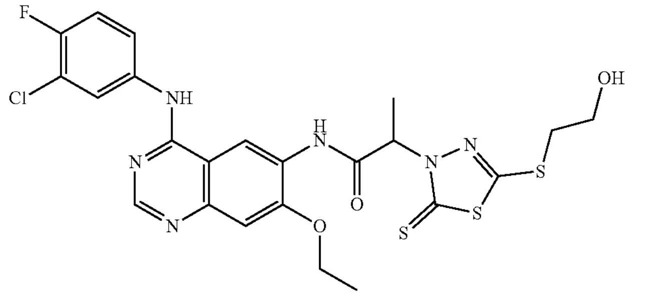 [SMILES: CCOc1cc2ncnc(Nc3ccc(F)c(Cl)c3)c2cc1NC(=O)C(C)n1nc(SCCO)sc1=S] |
| SGI-085 | 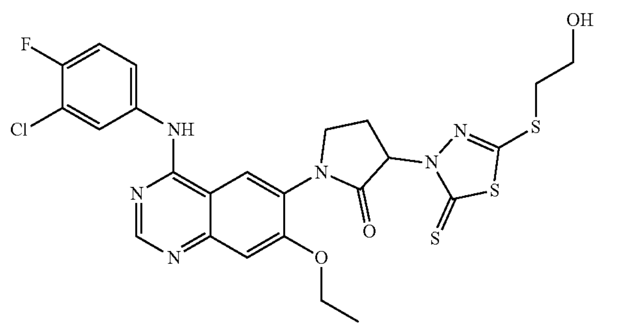 [SMILES: CCOc1cc2ncnc(Nc3ccc(F)c(Cl)c3)c2cc1N1CCC(n2nc(SCCO)sc2=S)C1=O] |
| SGI-086 | 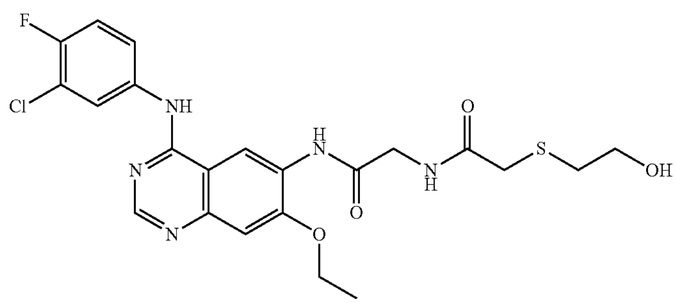 |
| SGI-087 | 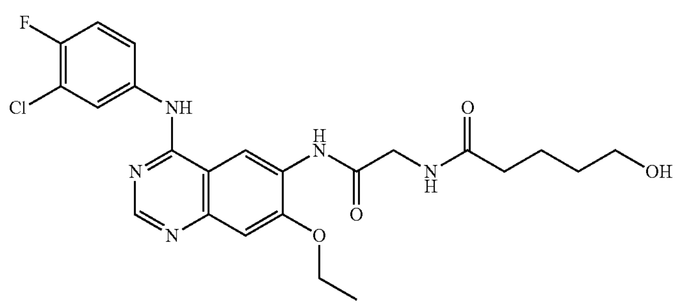 [SMILES: CCOc1cc2ncnc(Nc3ccc(F)c(Cl)c3)c2cc1NC(=O)CNC(=O)CCCCO] |
| SGI-088 | 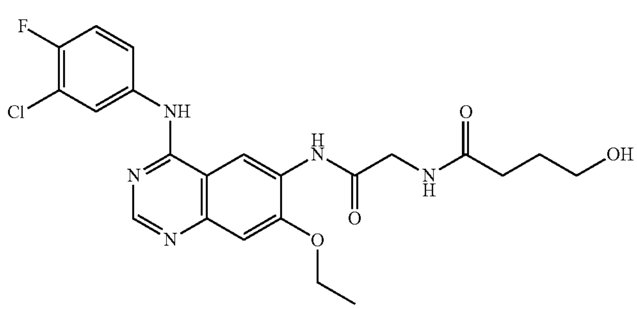 [SMILES: CCOc1cc2ncnc(Nc3ccc(F)c(Cl)c3)c2cc1NC(=O)CNC(=O)CCCO] |

TABLE 1-continued

Compound List

| Cpd ID | Structure |
|---|---|
| SGI-089 | 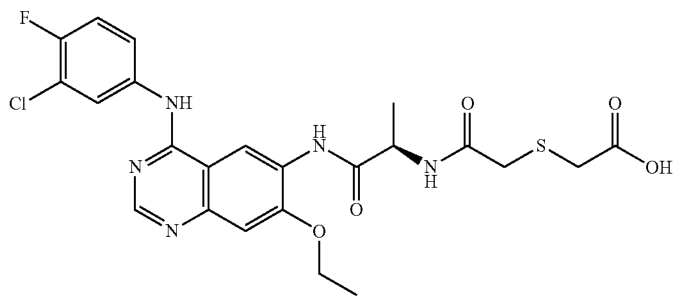 [SMILES: CCOc1cc2ncnc(Nc3ccc(F)c(Cl)c3)c2cc1NC(=O)[C@@H](C)NC(=O)CSCC(=O)O] |
| SGI-090 | 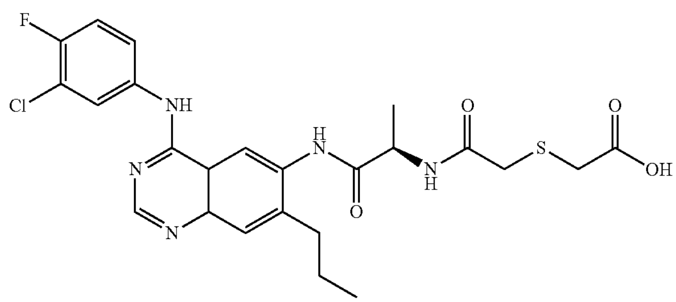 [SMILES: CCCC1=CC2N=CN=C(Nc3ccc(F)c(Cl)c3)C2C=C1NC(=O)[C@@H](C)NC(=O)CSCC(=O)O] |
| SGI-091 | 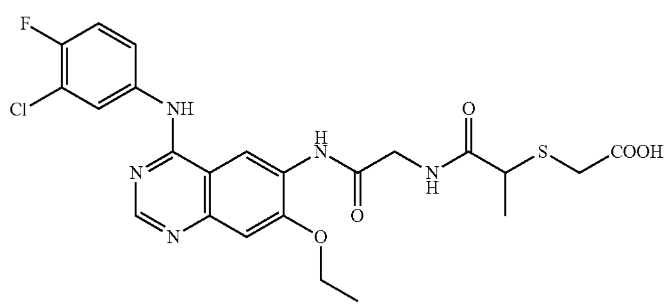 [SMILES: CCOc1cc2ncnc(Nc3ccc(F)c(Cl)c3)c2cc1NC(=O)CNC(=O)C(C)SCC(=O)O] |
| SGI-092 | 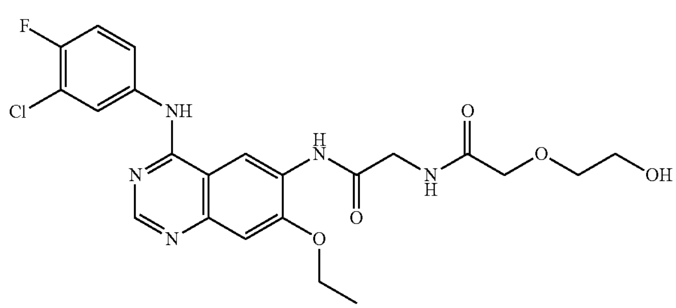 |
| SGI-093 | 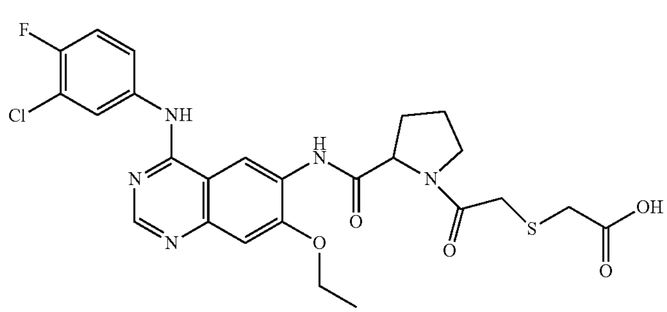 [SMILES: CCOc1cc2ncnc(Nc3ccc(F)c(Cl)c3)c2cc1NC(=O)C1CCCN1C(=O)CSCC(=O)O] |

TABLE 1-continued

Compound List

| Cpd ID | Structure |
|---|---|
| SGI-094 | 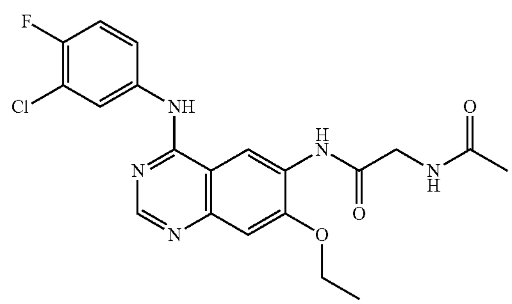 [SMILES: CCOc1cc2ncnc(Nc3ccc(F)c(Cl)c3)c2cc1NC(=O)CNC(C)=O] |
| SGI-095 | 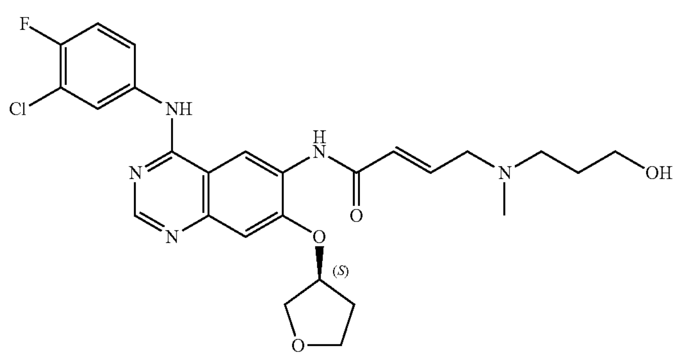 |
| SGI-096 | 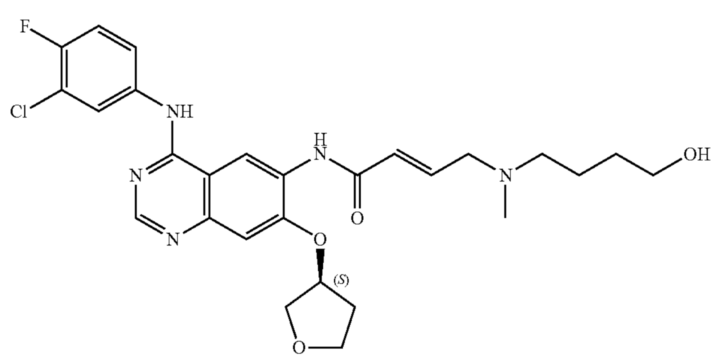 |
| SGI-097 | 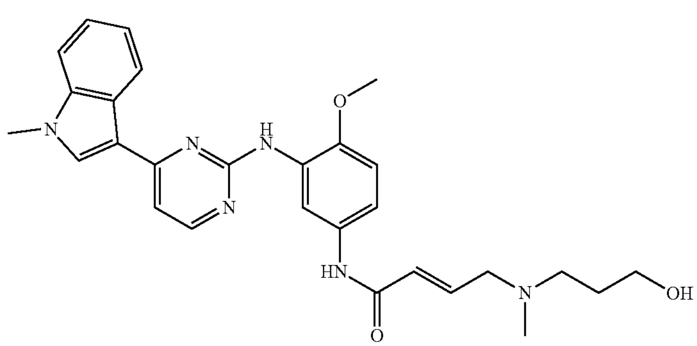 [SMILES: COc1ccc(NC(=O)/C=C/CN(C)CCCO)cc1Nc1nccc(-c2cn(C)c3ccccc23)n1] |

TABLE 1-continued
Compound List
| Cpd ID | Structure |
|---|---|
| SGI-098 | 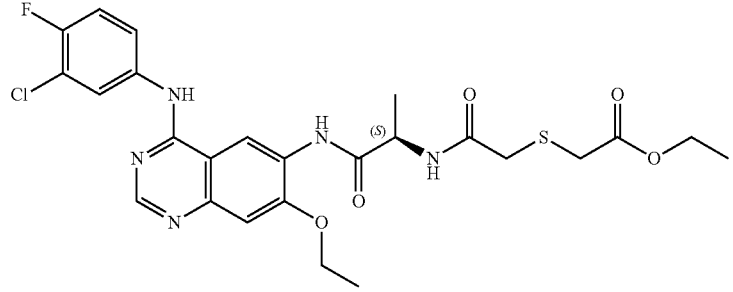 |
| SGI-099 | 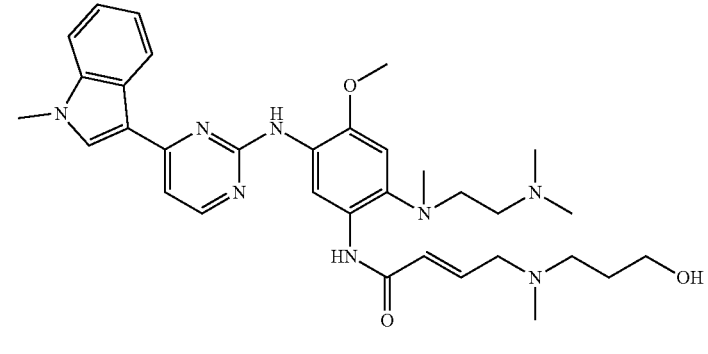 [SMILES: COc1cc(N(C)CCN(C)C)c(NC(=O)/C=C/CN(C)CCCO)cc1Nc1nccc(-c2cn(C)c3ccccc23)n1] |
| SGI-100 | 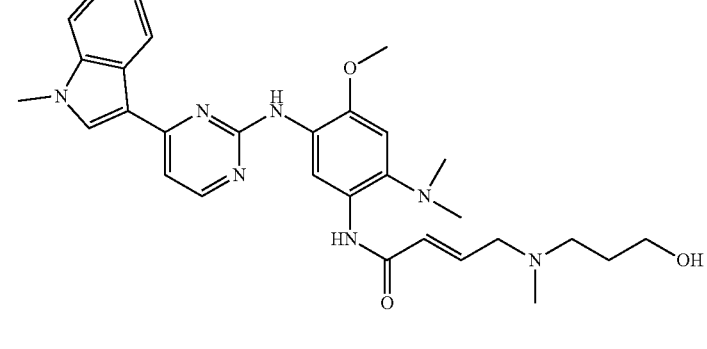 |
| SGI-101 | 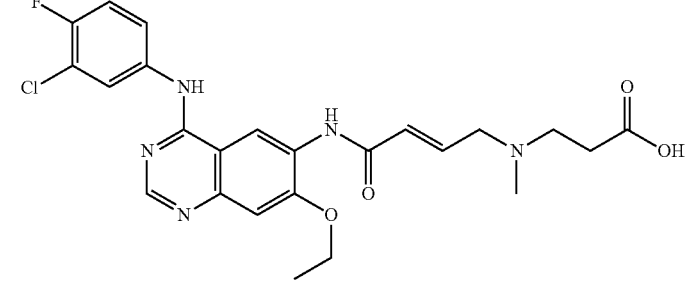 |

TABLE 1-continued

Compound List

| Cpd ID | Structure |
|---|---|
| SGI-102 | 4-((E)-4-((4-((3-chloro-4-fluorophenyl)amino)-7-ethoxyquinazolin-6-yl)amino)-N-methyl-4-oxobut-2-en-1-yl)(methyl)amino)butanoic acid |
| SGI-103 | ethyl 3-(((E)-4-((4-((3-chloro-4-fluorophenyl)amino)-7-ethoxyquinazolin-6-yl)amino)-4-oxobut-2-en-1-yl)(methyl)amino)propanoate |
| SGI-104 | ethyl 4-(((E)-4-((4-((3-chloro-4-fluorophenyl)amino)-7-ethoxyquinazolin-6-yl)amino)-4-oxobut-2-en-1-yl)(methyl)amino)butanoate |
| SGI-105 | (E)-N-(4-((3-chloro-4-fluorophenyl)amino)-7-ethoxyquinazolin-6-yl)-4-((3-methoxypropyl)(methyl)amino)but-2-enamide |
| SGI-106 | (E)-N-(8-((3-chloro-4-fluorophenyl)amino)-3-ethoxynaphthalen-2-yl)-4-((4-methoxybutyl)(methyl)amino)but-2-enamide |

TABLE 1-continued
Compound List
| Cpd ID | Structure |
|---|---|
| SGI-107 | 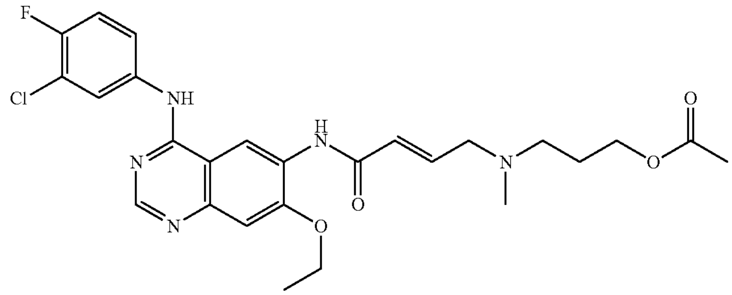 [SMILES: CCOc1cc2ncnc(Nc3ccc(F)c(Cl)c3)c2cc1NC(=O)/C=C/CN(C)CCCOC(C)=O] |
| SGI-108 | 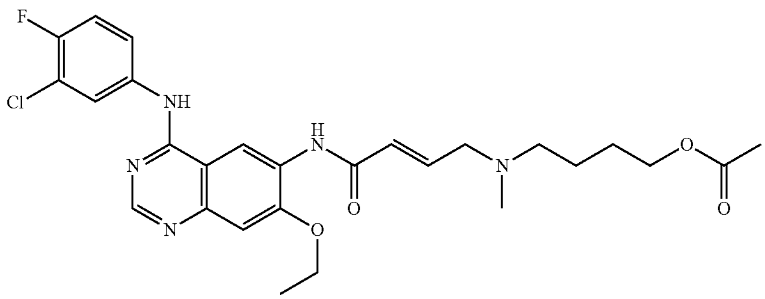 [SMILES: CCOc1cc2ncnc(Nc3ccc(F)c(Cl)c3)c2cc1NC(=O)/C=C/CN(C)CCCCOC(C)=O] |
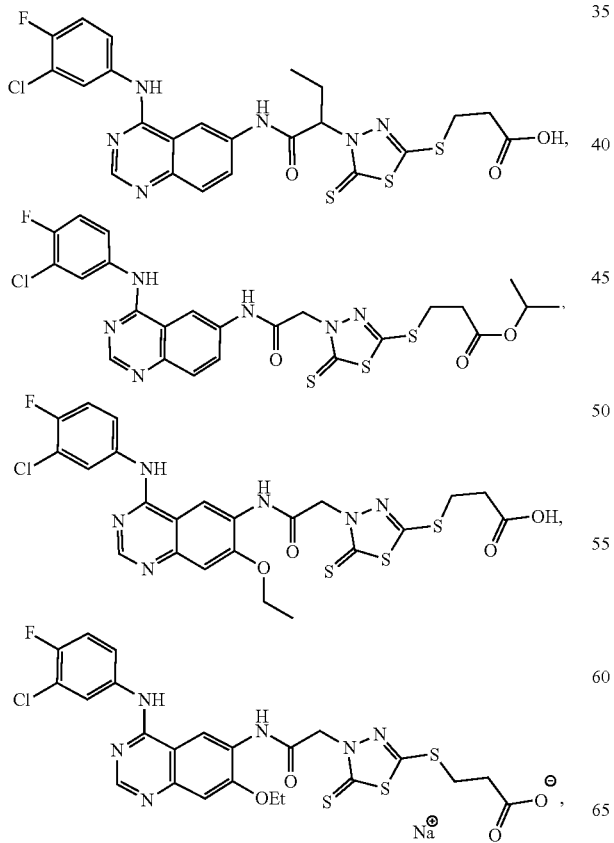
What is claimed is:
1. A compound having the following structure:
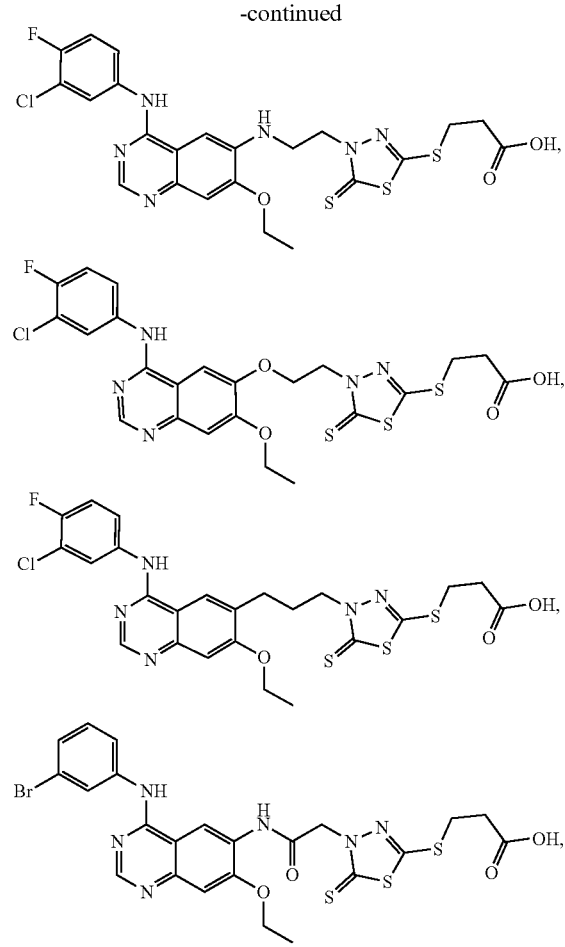

113
-continued
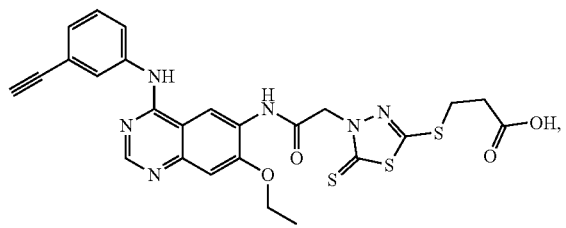
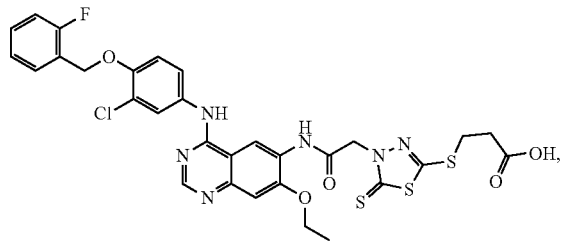
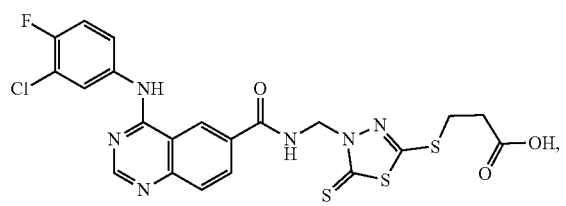
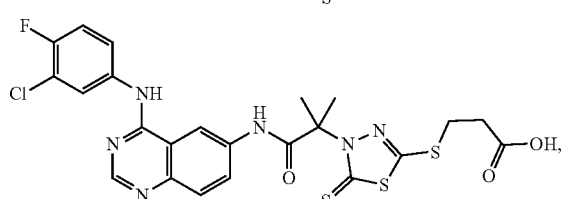
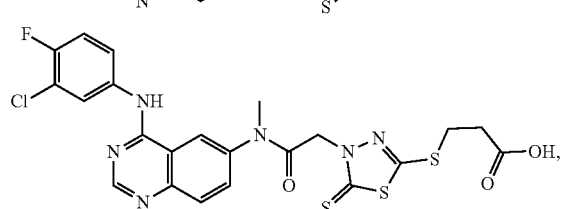
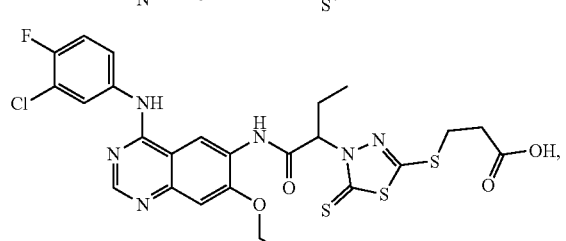
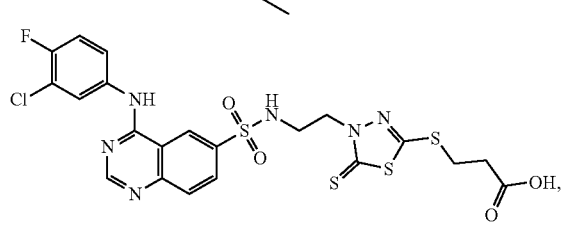
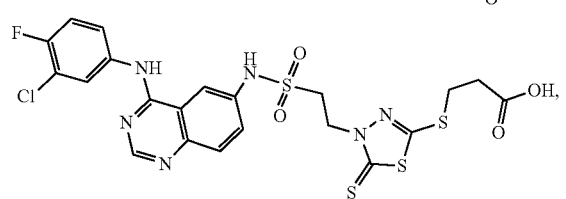
114
-continued
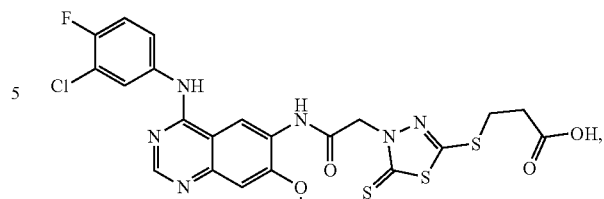
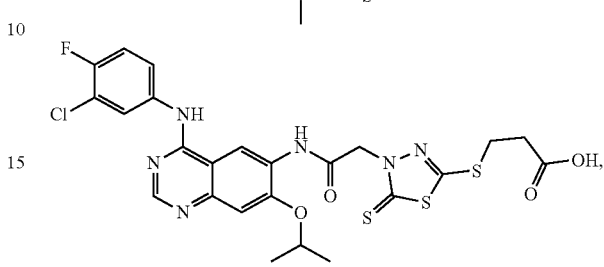
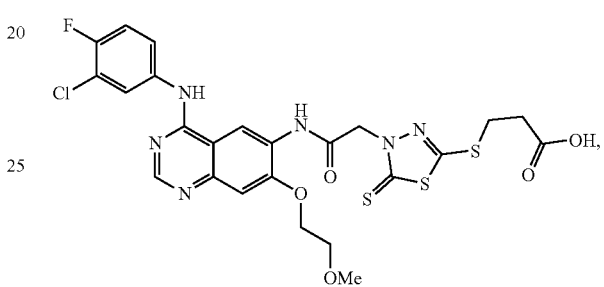
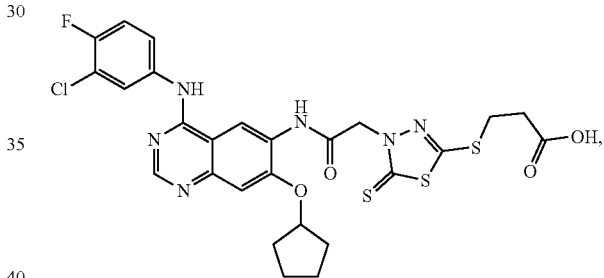
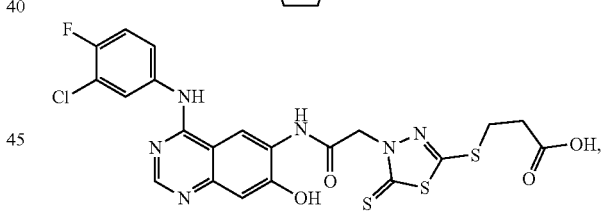
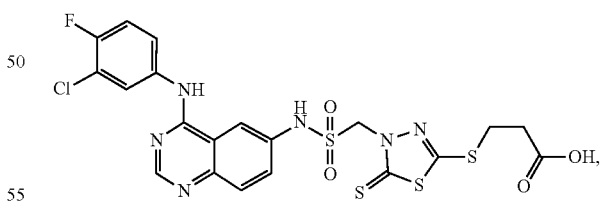
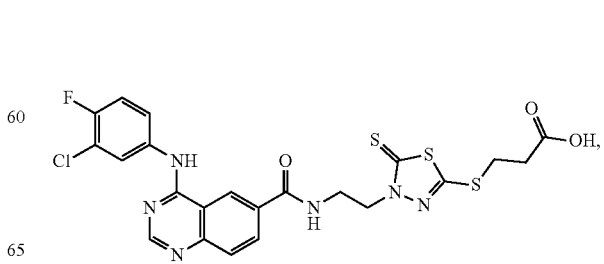

115
-continued
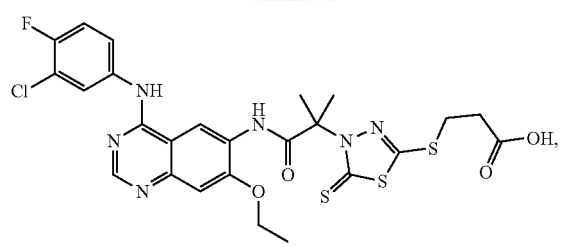
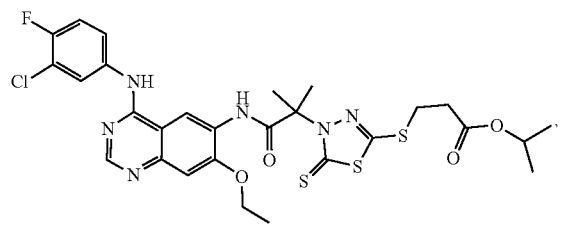
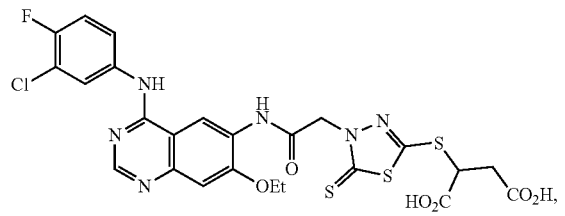
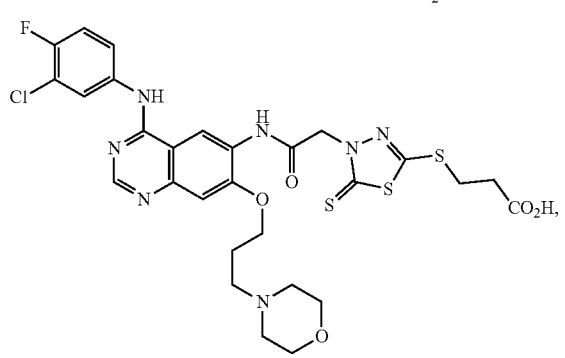
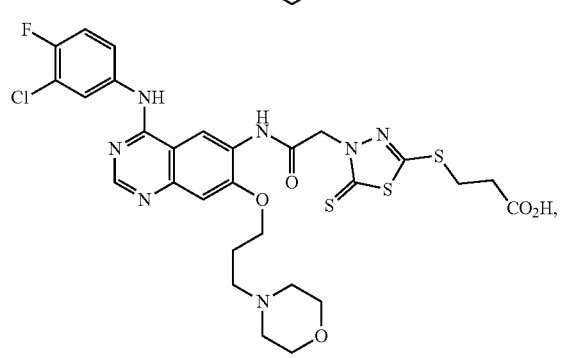
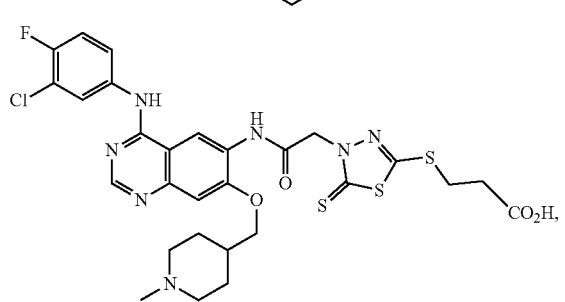
116
-continued
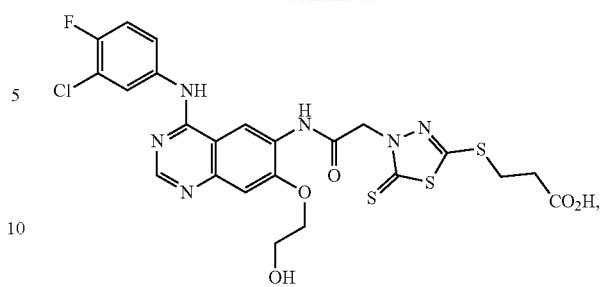
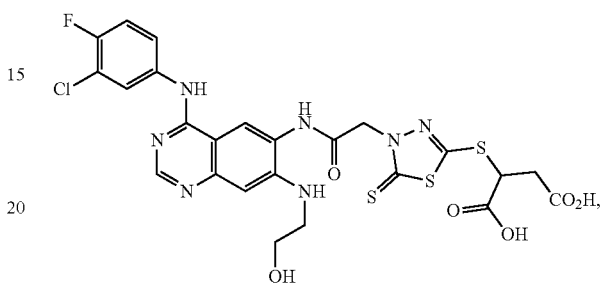
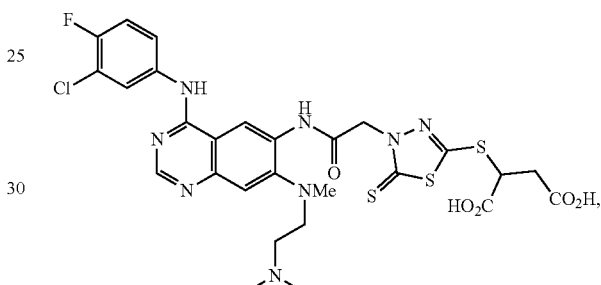
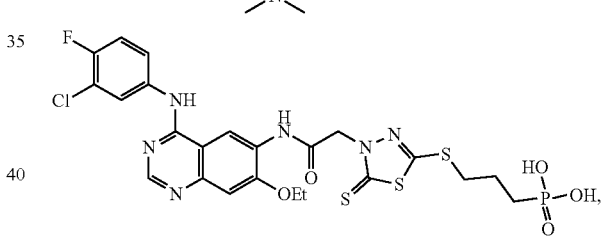
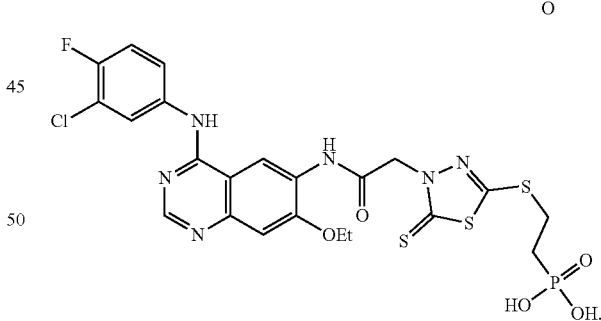
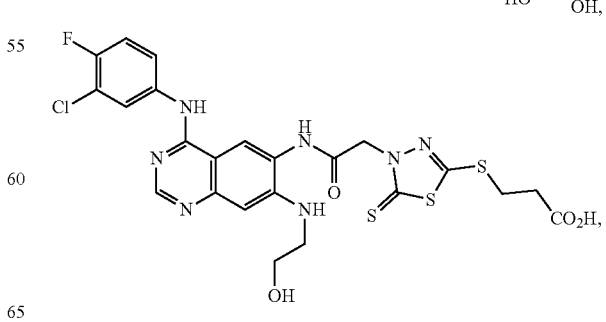

117
-continued
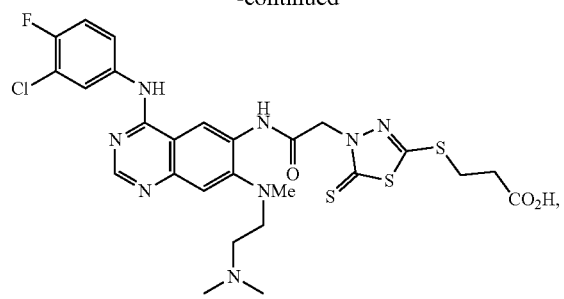
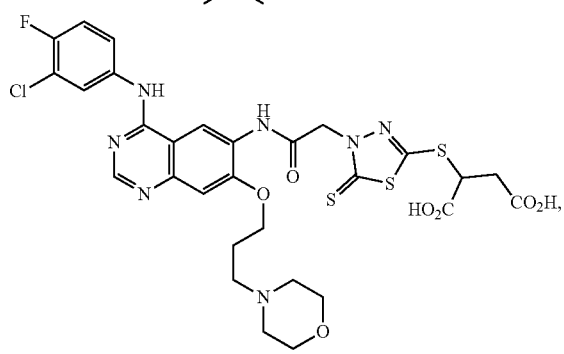
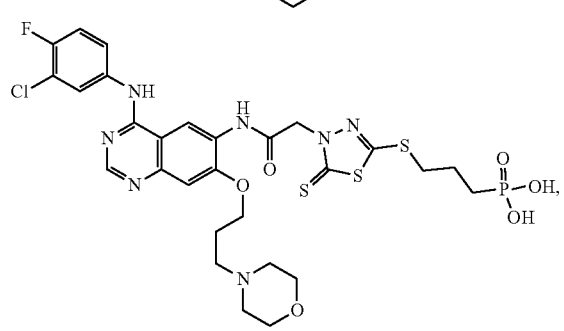
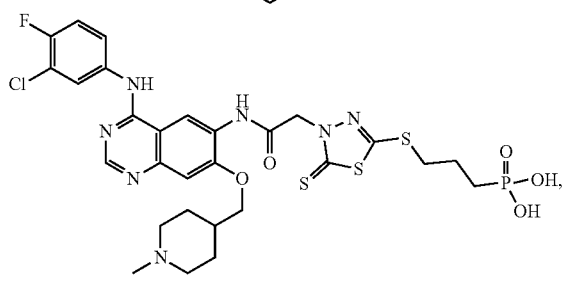
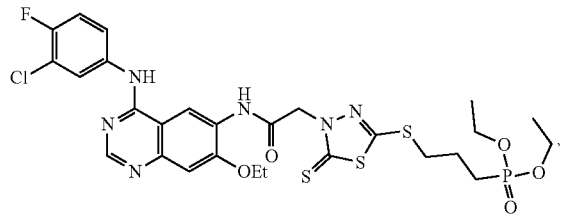
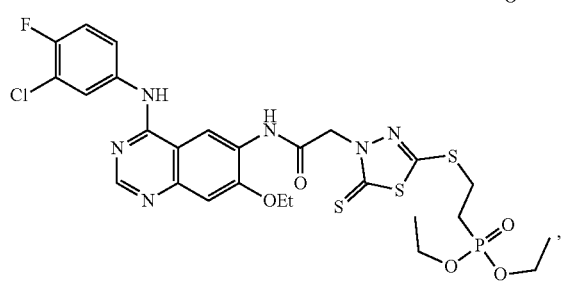
118
-continued
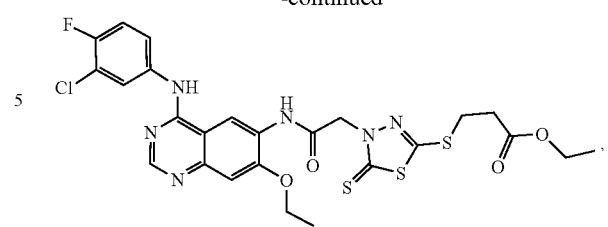
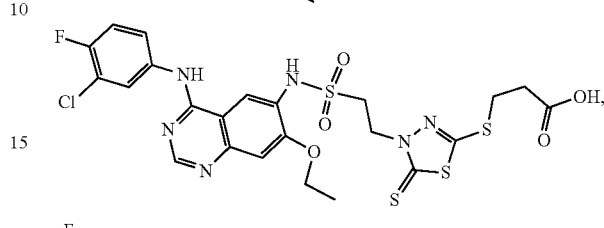
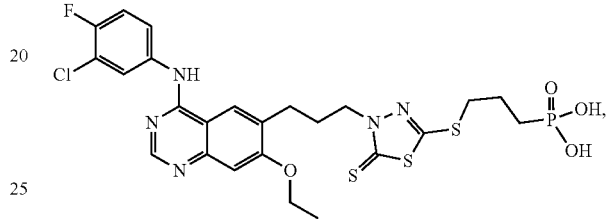
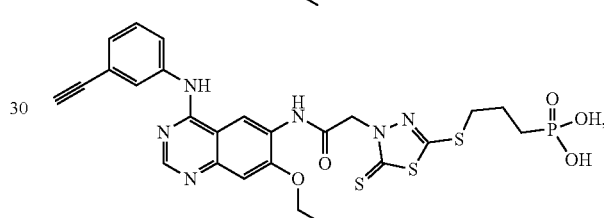
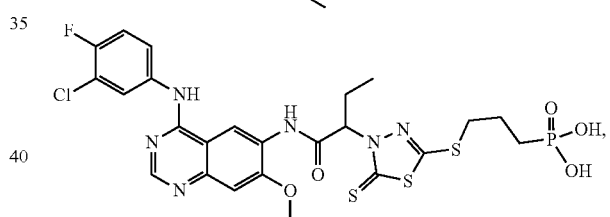
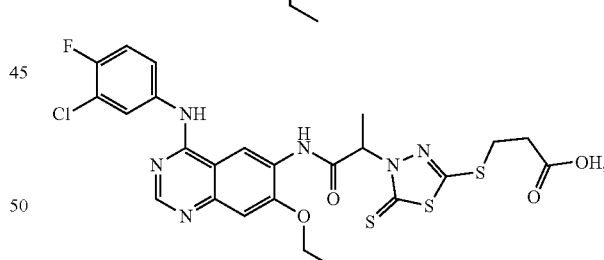
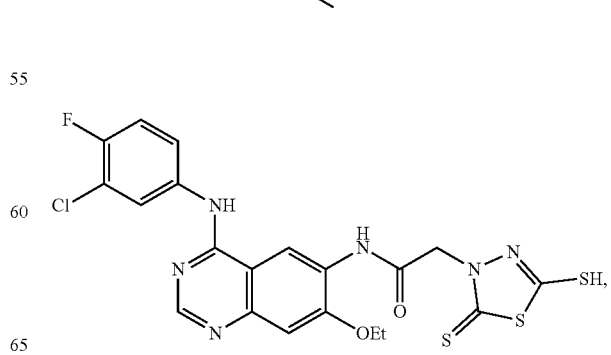

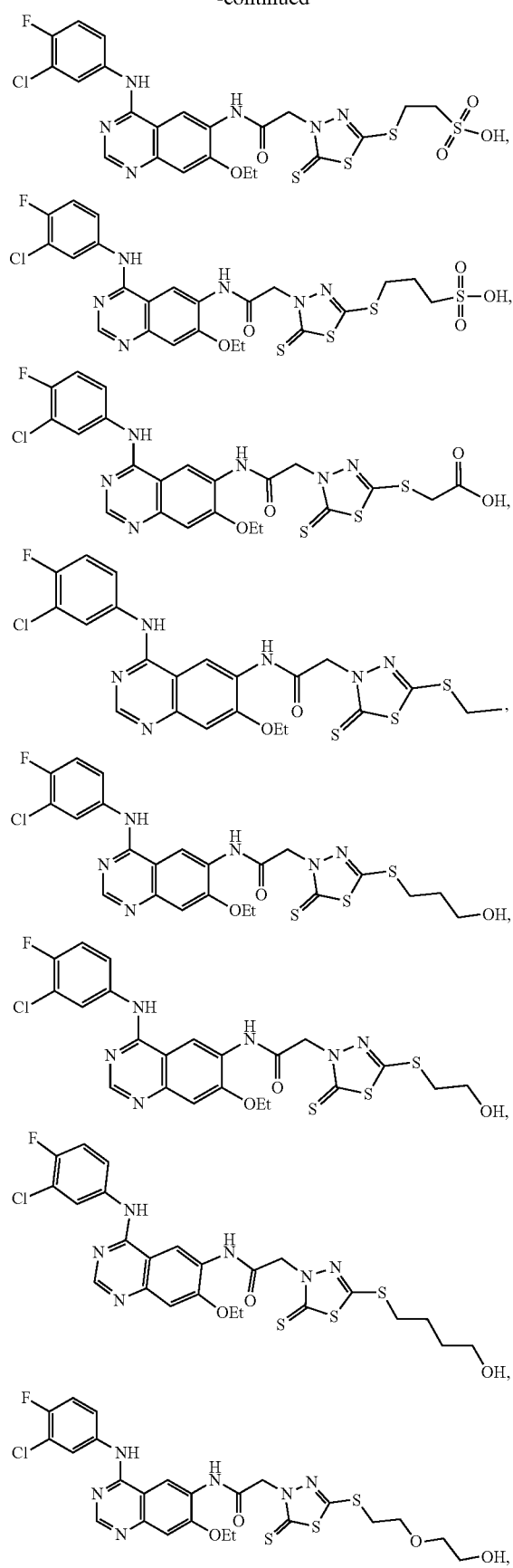
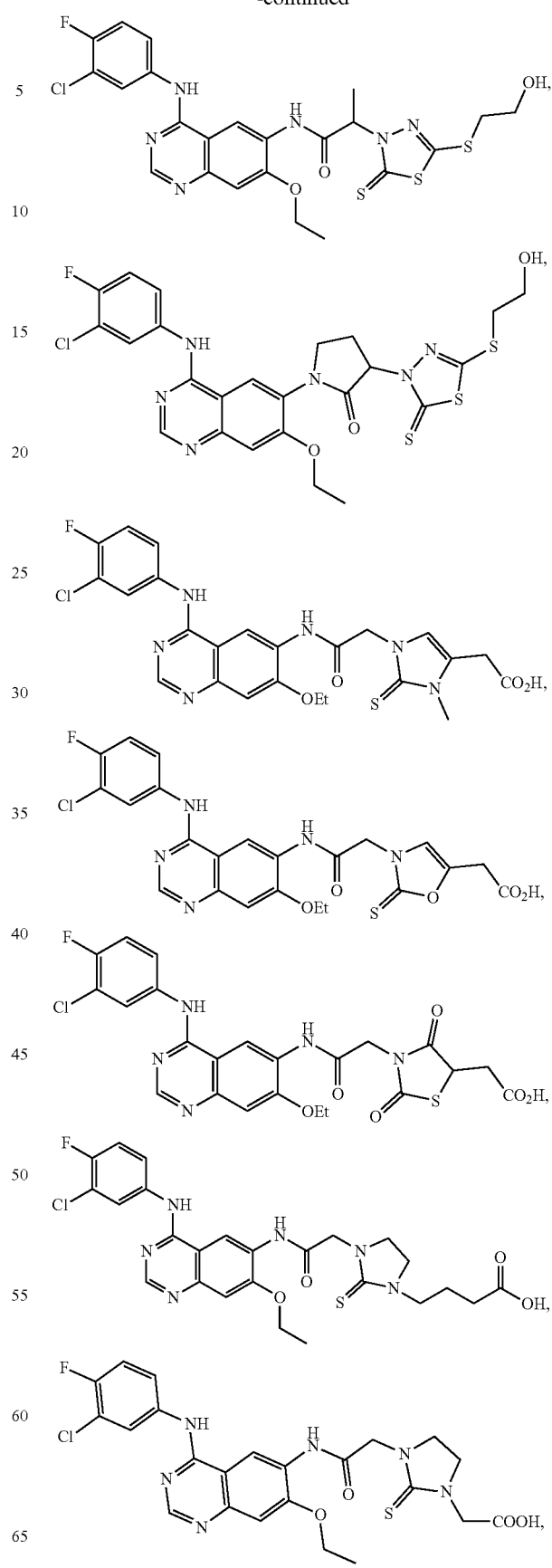

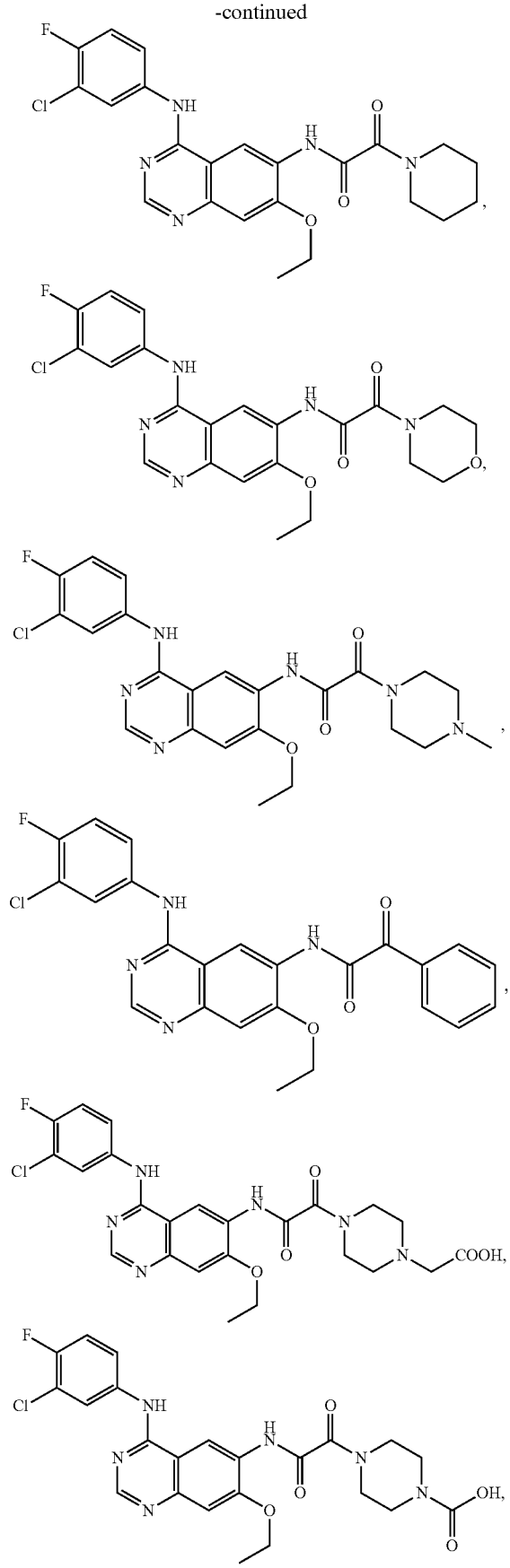

123
-continued
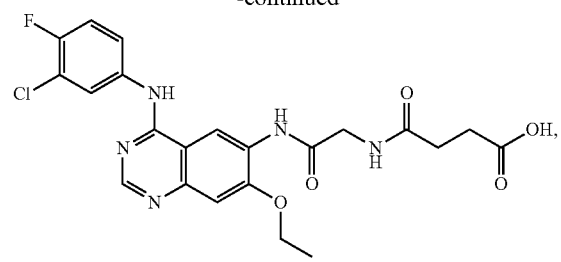
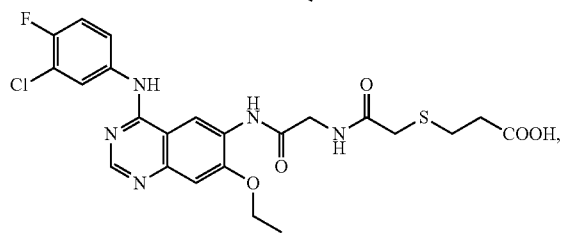
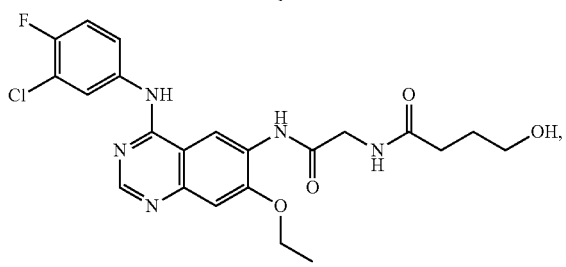
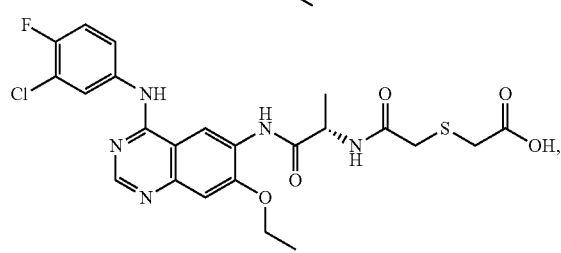
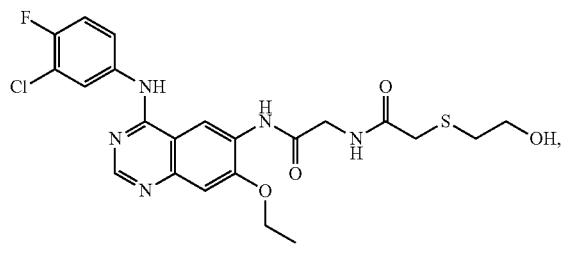
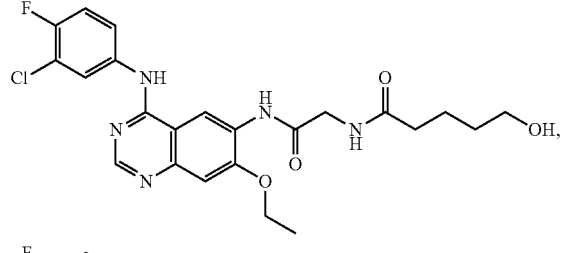
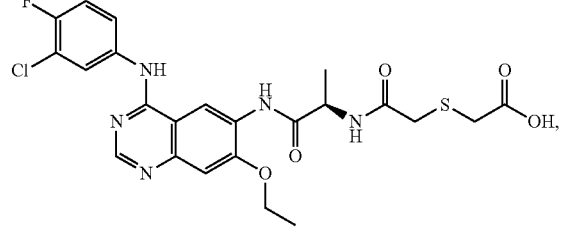
124
-continued
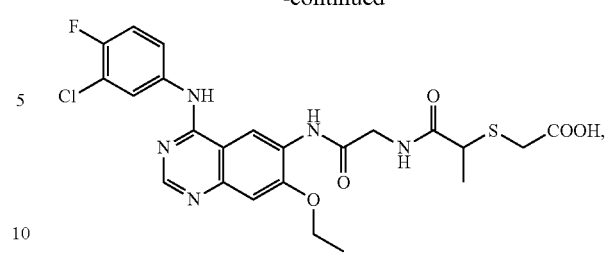
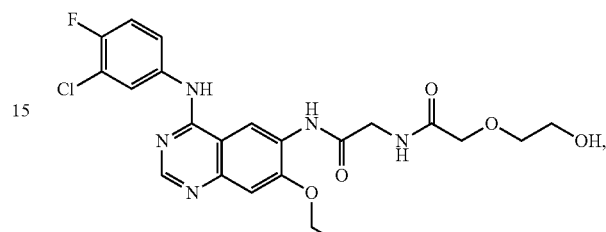
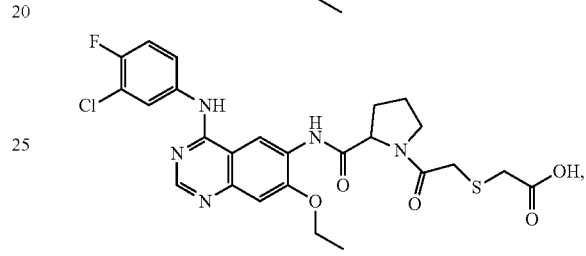
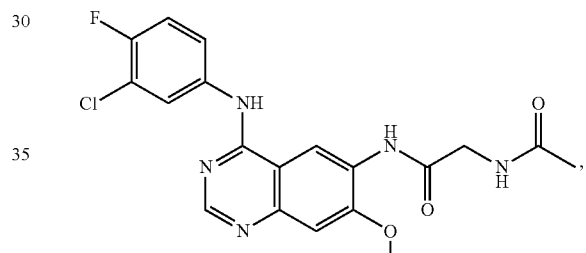
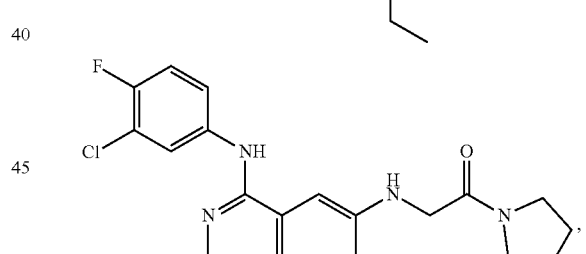
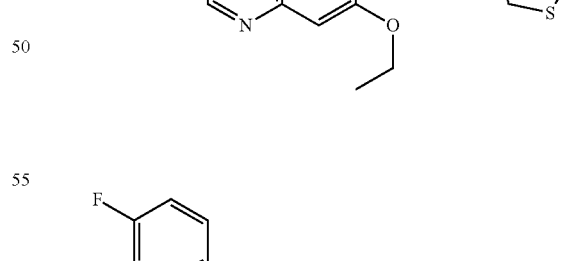
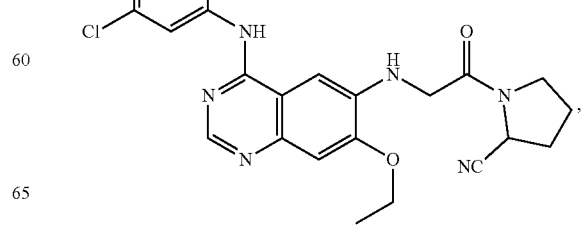

125
-continued
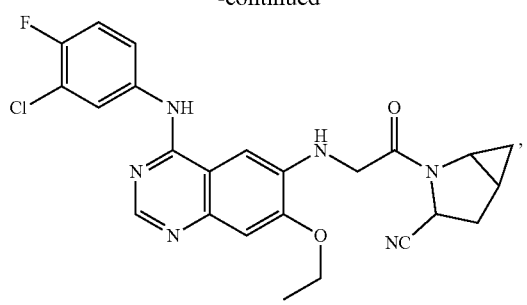
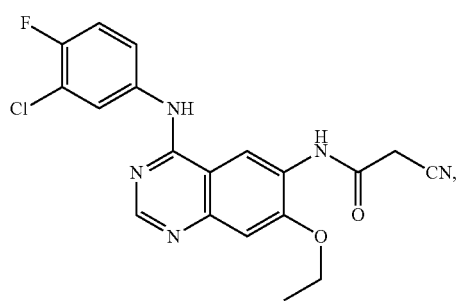
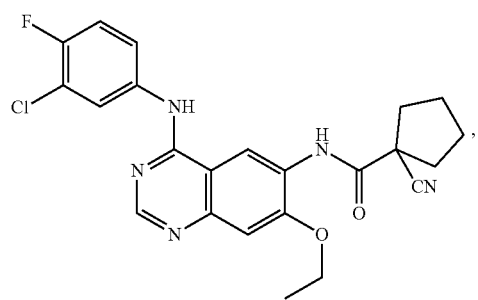
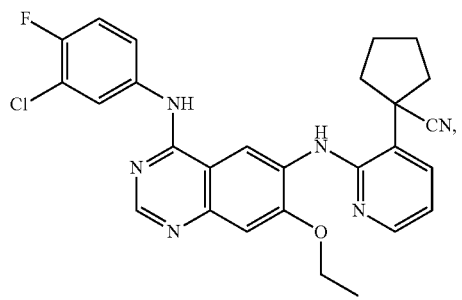
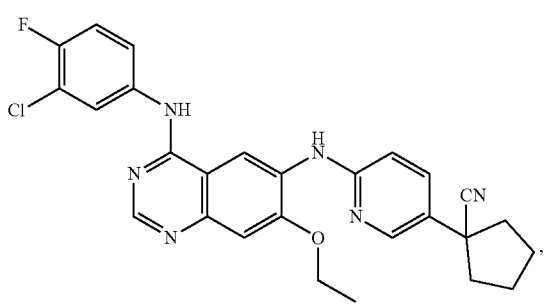
126
-continued
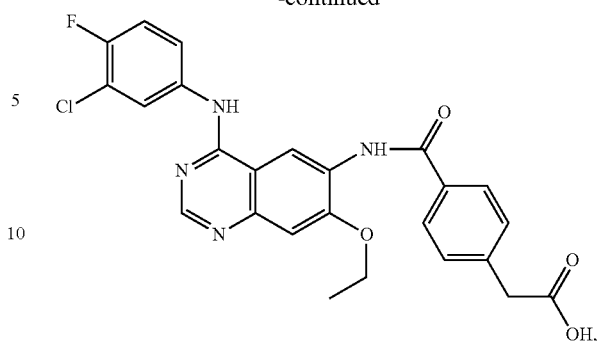
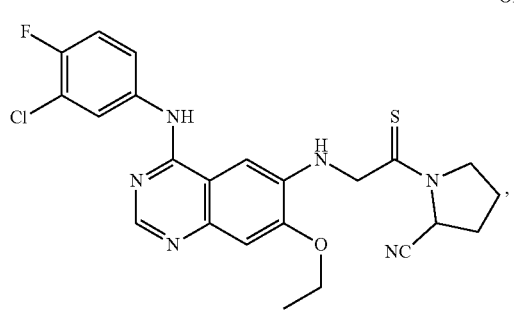
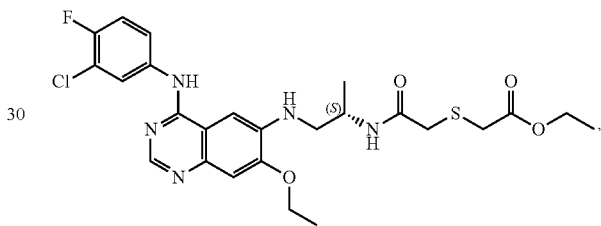
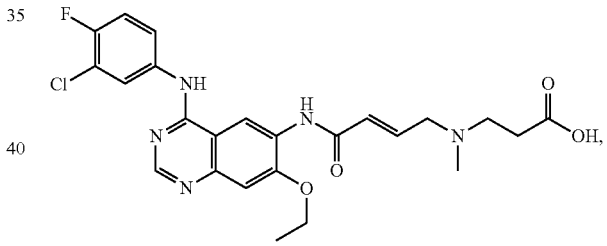
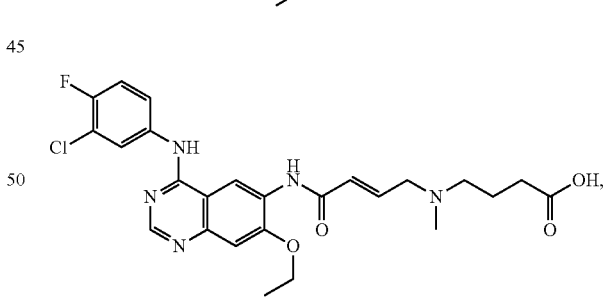
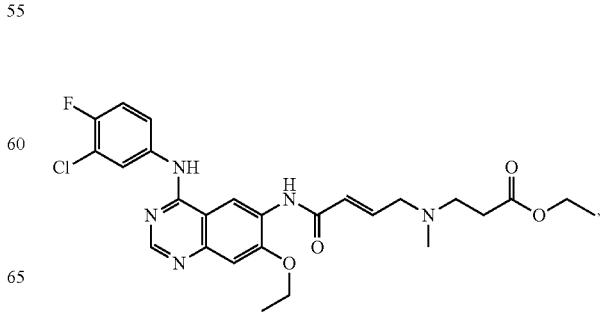

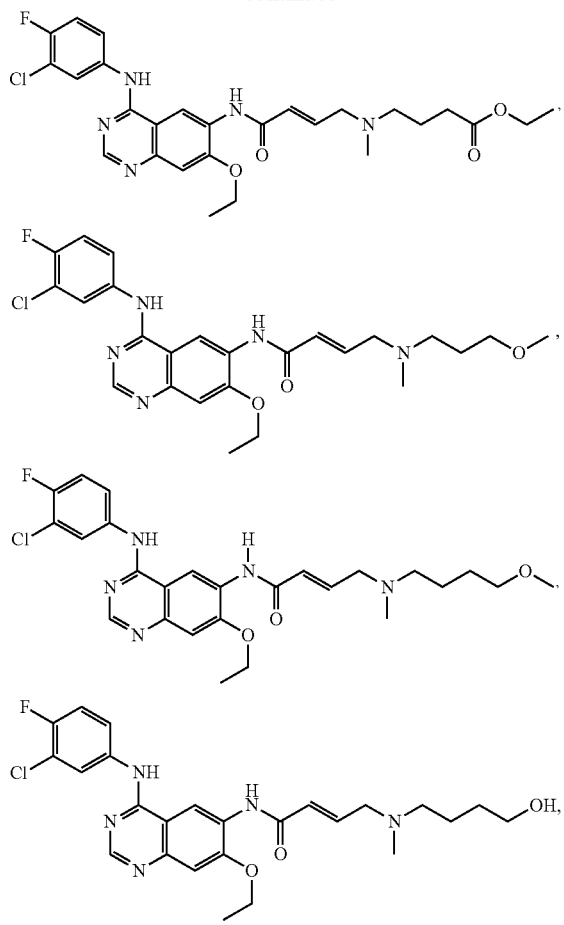

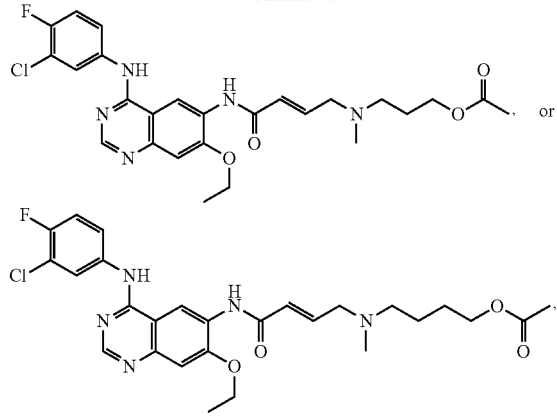

or a pharmaceutically acceptable salt thereof.

2. The compound according to claim 1, for use in the therapeutic treatment of cancer comprising at least one EGFR mutation selected from the group consisting of C797S, d746-750, T790M, or L858R.

3. The compound according to claim 2, wherein the cancer comprises a lung, head, neck, or pancreatic cancer.

4. A method of treating cancer, comprising administering to a subject having a cancer comprising at least one EGFR mutation selected from the group consisting of C797S, d746-750, T790M, or L858R in need thereof a therapeutically effective amount of a compound according to claim 1 or a pharmaceutically acceptable salt thereof.

5. The method according to claim 4, wherein the cancer comprises a lung, head, neck, or pancreatic cancer.

6. A pharmaceutical composition comprising a therapeutically effective amount of a compound according to claim 1 or a pharmaceutically acceptable salt thereof, and one or more pharmaceutically acceptable carriers.

* * * * *